United States Patent
Park et al.

(10) Patent No.: US 9,444,054 B2
(45) Date of Patent: Sep. 13, 2016

(54) COMPOUND FOR ORGANIC OPTOELECTRONIC DEVICE AND ORGANIC LIGHT EMITTING DIODE INCLUDING THE SAME

(71) Applicants: Moo-Jin Park, Uiwang-si (KR); Eun-Sun Yu, Uiwang-si (KR); Mi-Young Chae, Uiwang-si (KR)

(72) Inventors: Moo-Jin Park, Uiwang-si (KR); Eun-Sun Yu, Uiwang-si (KR); Mi-Young Chae, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 489 days.

(21) Appl. No.: 14/062,222

(22) Filed: Oct. 24, 2013

(65) Prior Publication Data

US 2014/0048789 A1  Feb. 20, 2014

Related U.S. Application Data

(63) Continuation of application No. PCT/KR2011/007384, filed on Oct. 6, 2011.

(30) Foreign Application Priority Data

Aug. 8, 2011 (KR) .......................... 10-2011-0078815

(51) Int. Cl.
H01L 51/50    (2006.01)
H01L 51/00    (2006.01)
(Continued)

(52) U.S. Cl.
CPC ......... *H01L 51/0067* (2013.01); *C07D 403/14* (2013.01); *C07D 409/14* (2013.01);
(Continued)

(58) Field of Classification Search
None
See application file for complete search history.

(56) References Cited

U.S. PATENT DOCUMENTS

2006/0147747 A1  7/2006  Yamamoto et al.
2007/0200490 A1  8/2007  Kawamura et al.
(Continued)

FOREIGN PATENT DOCUMENTS

CN    101104795 A    1/2008
JP    2000-095766 A    4/2000
(Continued)

OTHER PUBLICATIONS

Si et al., Synthesis, Structural Characterzation, and Electrophosphorescent Properties of Rhenium(I) Complexes Containing Carrier-Transporting Groups, 2007, Inorganic Chemistry, vol. 46, pp. 6155-6163.*

(Continued)

*Primary Examiner* — Gregory Clark
(74) *Attorney, Agent, or Firm* — Lee & Morse, P.C.

(57) ABSTRACT

A compound for an organic optoelectronic device is represented by the following Chemical Formula 1:

[Chemical Formula 1]

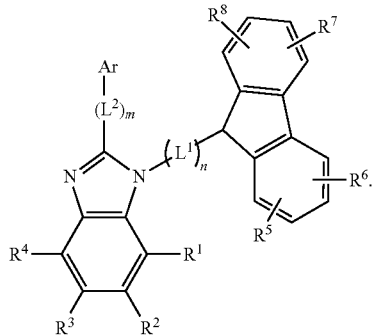

20 Claims, 3 Drawing Sheets

(51) Int. Cl.
    *C09K 11/06*     (2006.01)
    *H05B 33/14*     (2006.01)
    *C09B 57/00*     (2006.01)
    *C07D 403/14*     (2006.01)
    *C07D 409/14*     (2006.01)

(52) U.S. Cl.
CPC .............. *C09B 57/00* (2013.01); *C09K 11/06* (2013.01); *H01L 51/0072* (2013.01); *H01L 51/0074* (2013.01); *H05B 33/14* (2013.01); *C09K 2211/1029* (2013.01); *C09K 2211/1044* (2013.01); *H01L 51/0081* (2013.01); *H01L 51/0085* (2013.01); *H01L 51/5016* (2013.01); *Y02E 10/549* (2013.01)

(56) References Cited

U.S. PATENT DOCUMENTS

| | | |
|---|---|---|
| 2011/0198577 A1 | 8/2011 | Kambe et al. |
| 2013/0256641 A1 | 10/2013 | Jung et al. |

FOREIGN PATENT DOCUMENTS

| | | |
|---|---|---|
| JP | 2002-047274 A | 2/2002 |
| JP | 2010-092960 A | 4/2010 |
| KR | 10-2007-0023676 A | 2/2007 |
| KR | 10-0857655 B1 | 9/2008 |
| KR | 10-2009-0073852 A | 7/2009 |
| KR | 10-2010-0041690 A | 4/2010 |
| KR | 10-2010-0099459 A | 9/2010 |
| KR | 10-2011-0048840 A | 5/2011 |
| WO | WO 2004/080975 A1 | 9/2004 |

OTHER PUBLICATIONS

Junqiao Ding, et al., "Highly Efficient Green-Emitting Phosphorescent Iridium Dendrimers Based on Carbazole Dendrons", Adv. Funct. Mater. 2006, 16, pp. 575-581.

Junqiao Ding, et al., "Bifunctional Green Iridium Dendrimers with a "Self-Host" Feature for Highly Efficient Nondoped Electrophosphorescent Devices", Angew. Chem. Int. Ed. 2009, 48, pp. 6664-6666.

Lingcheng Chen, et al. "Bipolar Heteroleptic Green Iridium Dendrimers Containing Oligocarbazole and Oxadiazole Dendrons for Bright and Efficient Nondoped Electrophosphorescent Devices", Chem. Asian J. 2011, 6, pp. 1372-1380.

Dongfang Qiu, et al., "Synthesis, crystal structure, photophysical property and electropolymerization of Pt(II) complexes with carbazole-grafting 2-(2-pyridyl) benzimidazole", Inorganic Chemistry Communications 14 (2011) pp. 1520-1524.

Jing Wu, et al., Synthesis and Photoluminescent Properties of Series Ternary Lanthanide (Eu(III), Sm(III), Nd(III), Er(III), Yb(III)) complexes containing 4,4,4-trifluoro-1-(2-naphthyl)-1,3butanedionate and carbazole-functionalized ligand, Inorganica Chemica Acta 363 (2010) pp. 2394-2400.

Dansong Zhang, "Novel green-emitting copper(I) complexes with electron donors incorporated ligands: Synthesis, photophysical properties, and electroluminescence performances", Journal of Luminescence 130 (2010) pp. 1419-1424.

Bin Du, et al., "Novel chemosensory materials based on polyfluorenes with 2-(2'-pyridyl)- benzimidazole and 5-methyl-3-(pyridin-2-yl)-1,2,4-triazole groups in the side chain", Polymer 48 (2007) pp. 1245-1254.

Search Report mailed Aug. 19, 2014 in corresponding Chinese Patent Application No. 201180071548.X.

Search Report mailed Jan. 7, 2015 in corresponding European Patent Application No. 11870589.6.

Takizawa, et al.; "Phenylbenzimidazole-Based New Bipolar Host Materials for Efficient Phosphorescent Organic Light-Emitting Diodes," Chem. Mater.; 2009; pp. 2452-2458; 21; American Chemical Society; USA.

Chen, et al. "Versatile, Benzimidazole/Amine-Based Ambipolar Compounds for Electroluminescent Applications: Single-Layer, Blue, Fluorescent OLEDs, Hosts for Single-Layer, Phosphorescent OLEDs" Advanced Functional Materials.; 2009; pp. 2661-2670; 19; WILEY-VCH Verlag GmbH & Co. KGaA, Weinheim; Federal Republic of Germany.

International Search Report in PCT/KR2011/007384, dated Aug. 24, 2012 (Park, et al.).

* cited by examiner

COMPOUND FOR ORGANIC OPTOELECTRONIC DEVICE AND ORGANIC LIGHT EMITTING DIODE INCLUDING THE SAME

CROSS-REFERENCE TO RELATED APPLICATIONS

This application is a continuation of pending International Application No. PCT/KR2011/007384, entitled "Compound for Organic Optoelectronic Device and Organic Light Emitting Diode Including the Same," which was filed on Oct. 6, 2011, the entire contents of which are hereby incorporated by reference.

Korean Patent Application No. 10-2011-0078815, filed on Aug. 8, 2011, in the Korean Intellectual Property Office, and entitled: "Compound For Organic Optoelectronic Device and Organic Light Emitting Diode Including The Same," is incorporated by reference herein in its entirety.

BACKGROUND

1. Field

Embodiments relate to a compound for an organic optoelectronic device and an organic light emitting diode including the same.

2. Description of the Related Art

An organic optoelectronic device is a device using a charge exchange between an electrode and an organic material by using holes or electrons.

An organic optoelectronic device may be classified as follows in accordance with its driving principles. A first organic optoelectronic device is an electronic device driven as follows: excitons are generated in an organic material layer by photons from an external light source; the excitons are separated into electrons and holes; and the electrons and holes are transferred to different electrodes as a current source (voltage source).

A second organic optoelectronic device is an electronic device driven as follows: a voltage or a current is applied to at least two electrodes to inject holes and/or electrons into an organic material semiconductor positioned at an interface of the electrodes, and the device is driven by the injected electrons and holes.

Examples of an organic optoelectronic device include an organic photoelectric device, an organic light emitting diode, an organic solar cell, an organic photo conductor drum, an organic transistor, or the like, which use a hole injecting or transport material, an electron injecting or transport material, or a light emitting material.

For example, an organic light emitting diode (OLED) has recently drawn attention due to an increase in demand for flat panel displays. In general, organic light emission refers to conversion of electrical energy into photo-energy.

Such an organic light emitting diode converts electrical energy into light by applying current to an organic light emitting material. It has a structure in which a functional organic material layer is interposed between an anode and a cathode. The organic material layer may include a multilayer including different materials, for example a hole injection layer, a hole transport layer, an emission layer, an electron transport layer, and an electron injection layer, in order to improve efficiency and stability of an organic optoelectronic device.

In such an organic light emitting diode, when a voltage is applied between an anode and a cathode, holes from the anode and electrons from the cathode are injected to an organic material layer and recombined to generate excitons having high energy. The generated excitons generate light having certain wavelengths while shifting to a ground state.

A phosphorescent light emitting material may be used for a light emitting material of an organic optoelectronic device in addition to the fluorescent light emitting material. Such a phosphorescent material emits lights by transporting the electrons from a ground state to an exited state, non-radiance transiting of a singlet exciton to a triplet exciton through intersystem crossing, and transiting a triplet exciton to a ground state to emit light.

As described above, in an organic light emitting diode, an organic material layer includes a light emitting material and a charge transport material, for example a hole injection material, a hole transport material, an electron transport material, an electron injection material, or the like.

The light emitting material is classified as blue, green, and red light emitting materials according to emitted colors, and yellow and orange light emitting materials to emit colors approaching natural colors.

When one material is used as a light emitting material, a maximum light emitting wavelength may be shifted to a long wavelength or color purity may decrease because of interactions between molecules, or device efficiency may decrease because of a light emitting quenching effect. Therefore, a host/dopant system may be included as a light emitting material in order to improve color purity and increase luminous efficiency and stability through energy transfer.

A material constituting an organic material layer, for example a hole injection material, a hole transport material, a light emitting material, an electron transport material, an electron injection material, and a light emitting material such as a host and/or a dopant, that is stable and has good efficiency may enhance performance of an organic light emitting diode.

A low molecular weight organic light emitting diode may be manufactured as a thin film in a vacuum deposition method, and may have good efficiency and life-span performance. A polymer organic light emitting diode may be manufactured in an inkjet or spin coating method, and may have an advantage of low initial cost and being large-sized.

Both low molecular weight organic light emitting and polymer organic light emitting diodes may have an advantage of self-light emitting, high speed response, wide viewing angle, ultra-thin form, high image quality, durability, large driving temperature range, or the like. They may have good visibility due to self-light emitting characteristics compared with a LCD (liquid crystal display), and may have an advantage of decreasing thickness and weight of LCD up to a third, because they do not need a backlight.

In addition, they have a response speed 1000 times faster in microsecond units than an LCD. Thus, they may realize a motion picture without after-image. Based on these advantages, they have been remarkably developed to have 80 times efficiency and more than 100 times life-span since they come out for the first time in the late 1980's. They keep being made larger, such as a 40-inch organic light emitting diode panel.

SUMMARY

Embodiments are directed to a compound for an organic optoelectronic device represented by the following Chemical Formula 1:

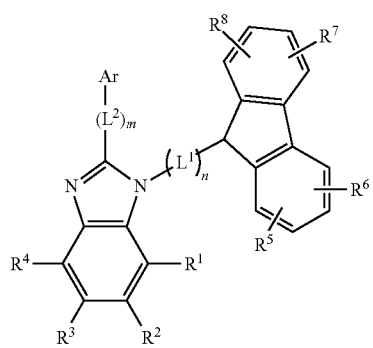

[Chemical Formula 1]

In the above Chemical Formula 1, $L^1$ and $L^2$ may each independently be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m may each independently be integers ranging from 0 to 3, Ar may be a substituted or unsubstituted C6 to C30 aryl group, a substituted or unsubstituted C3 to C30 heteroaryl group, or a combination thereof, $R^1$ to $R^8$ may each independently be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and at least one of $R^5$ to $R^8$ may be a substituted or unsubstituted C3 to C30 heteroaryl group having hole characteristics, a substituted or unsubstituted C6 to C30 aryl group having hole characteristics, a substituted or unsubstituted arylamine group having hole characteristics, or a combination thereof.

At least one of the $R^5$ to $R^8$ may be the substituted or unsubstituted C6 to C30 aryl group having hole characteristics, the substituted or unsubstituted C6 to C30 aryl group having hole characteristics being a substituted or unsubstituted triphenylenyl group.

The compound for an organic optoelectronic device may be represented by the following Chemical Formula 2:

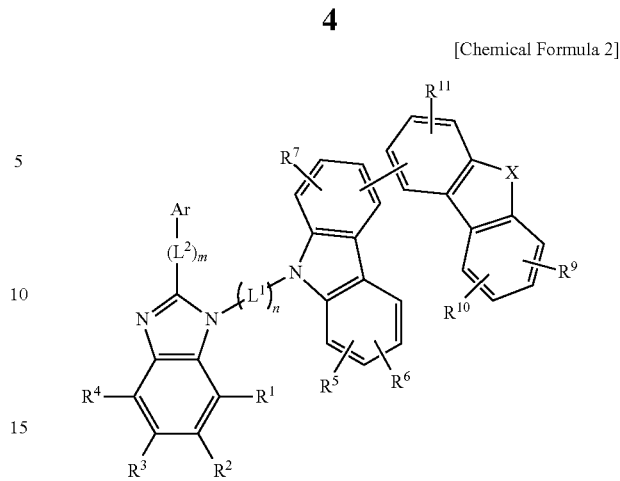

[Chemical Formula 2]

In the above Chemical Formula 2, $L^1$ and $L^2$ may each independently be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m may each independently be integers ranging from 0 to 3, Ar may be a substituted or unsubstituted C6 to C30 aryl group, a substituted or unsubstituted C3 to C30 heteroaryl group, or a combination thereof, $R^1$ to $R^7$ and $R^9$ to $R^{11}$ may each independently be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X may be NR', O, or S, wherein the R' may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The compound for an organic optoelectronic device may be represented by the following Chemical Formula 3:

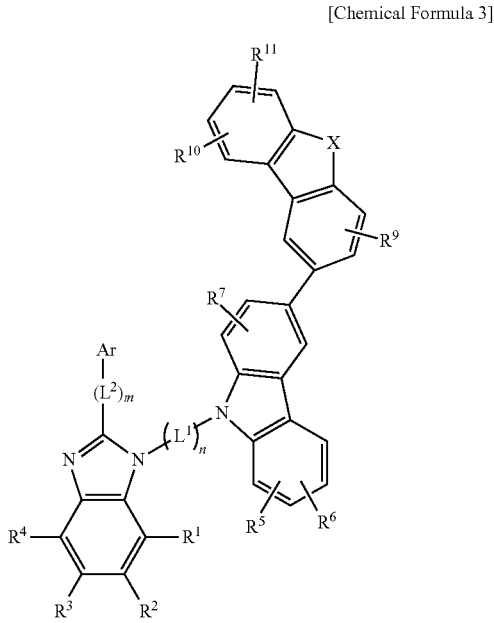

[Chemical Formula 3]

In the above Chemical Formula 3, $L^1$ and $L^2$ may each independently be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m may each independently be integers ranging from 0 to 3, Ar may be a substituted or unsubstituted C6 to C30 aryl group, a substituted or unsubstituted C3 to C30 heteroaryl group, or a combination thereof, $R^1$ to $R^7$ and $R^9$ to $R^{11}$ may each independently be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X may be NR', O, or S, wherein the R' may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The compound for an organic optoelectronic device may be represented by the following Chemical Formula 4:

[Chemical Formula 4]

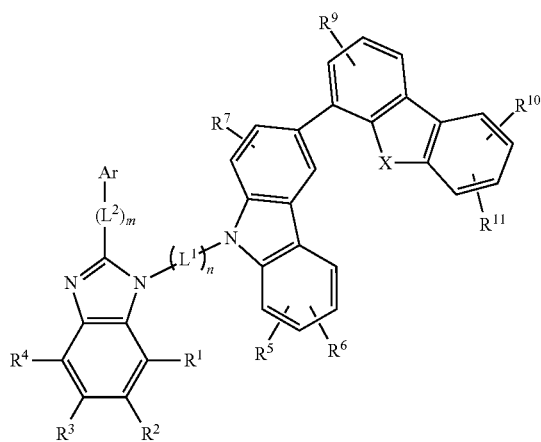

In the above Chemical Formula 4, $L^1$ and $L^2$ may each independently be a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m may each independently be integers ranging from 0 to 3, Ar may be a substituted or unsubstituted C6 to C30 aryl group, a substituted or unsubstituted C3 to C30 heteroaryl group, or a combination thereof, $R^1$ to $R^7$ and $R^9$ to $R^{11}$ may each independently be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X may be NR', O, or S, wherein the R' may be hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The Ar may be a substituted or unsubstituted biphenyl group, a substituted or unsubstituted pyridinyl group, a substituted or unsubstituted pyrimidinyl group, a substituted or unsubstituted triazinyl group, or a combination thereof.

The $L^1$ may be a substituted or unsubstituted phenylene group.

The n may be 1, and the m may be 0 or 1.

The substituted or unsubstituted C3 to C30 heteroaryl group having hole characteristics may be a substituted or unsubstituted carbazolyl-based derivative, a substituted or unsubstituted dibenzofuranyl-based derivative, a substituted or unsubstituted dibenzothiophenyl-based derivative, or a combination thereof.

The substituted or unsubstituted C6 to C30 aryl group having hole characteristics may be a substituted or unsubstituted fluorenyl group, a substituted or unsubstituted spiro-fluorenyl group, or a combination thereof.

The substituted or unsubstituted arylamine group having hole characteristics may include a single aryl group or a plurality of aryl groups, and the single aryl group or a plurality of aryl groups may independently be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, or a combination thereof.

Embodiments are also directed to a compound for an organic optoelectronic device represented by one of the following Chemical Formulae A1 to A21:

[Chemical Formula A1]

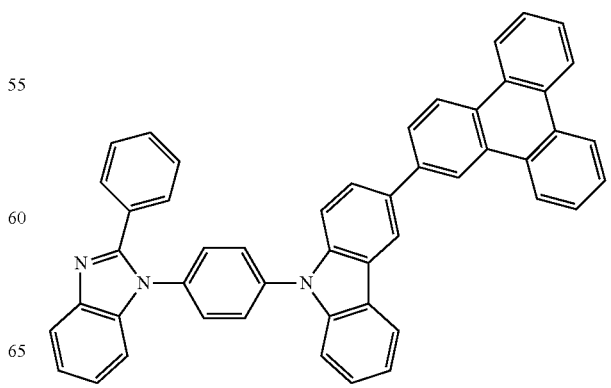

[Chemical Formula A2]
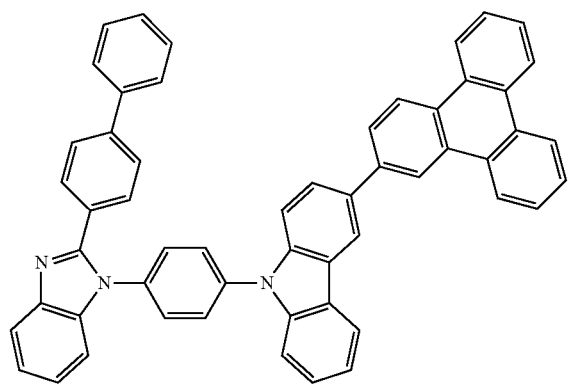
[Chemical Formula A6]
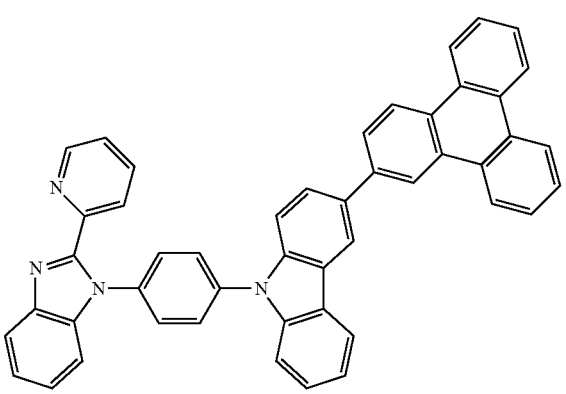
[Chemical Formula A3]
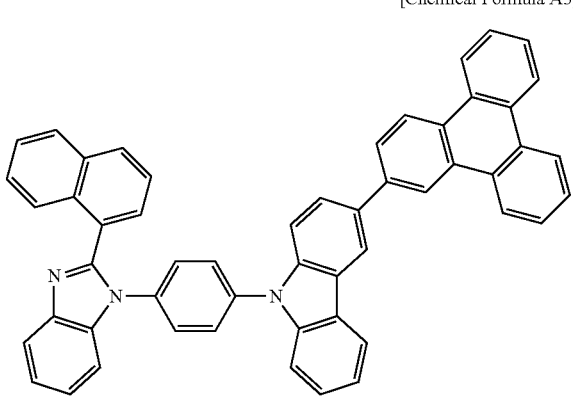
[Chemical Formula A7]
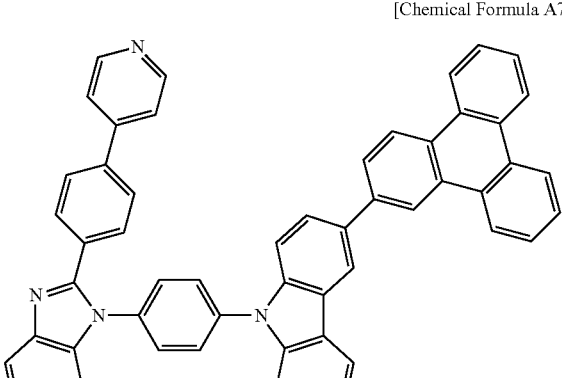
[Chemical Formula A4]
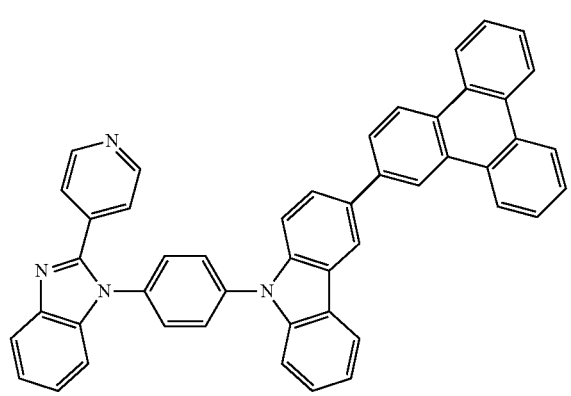
[Chemical Formula A8]
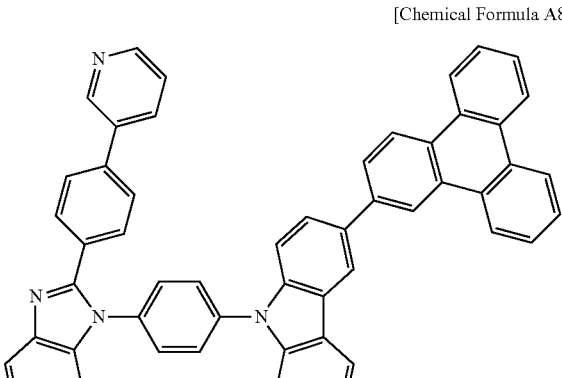
[Chemical Formula A5]
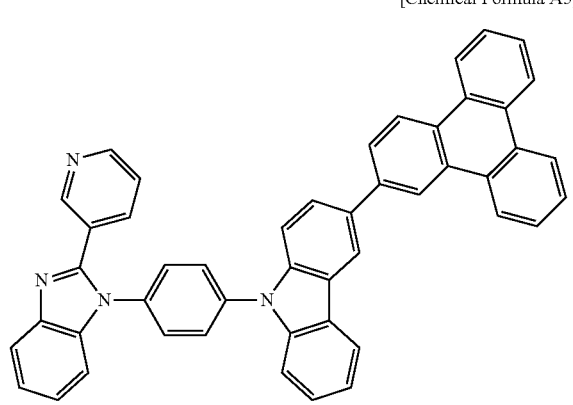
[Chemical Formula A9]
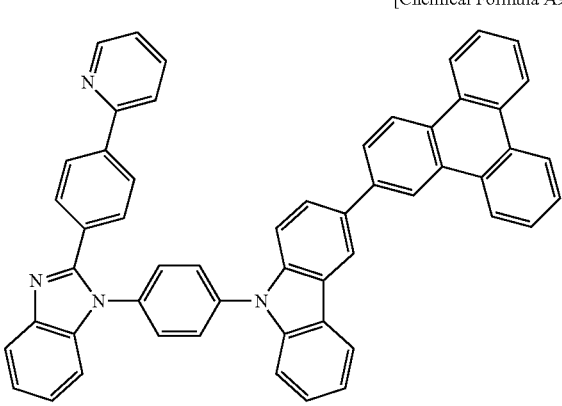

[Chemical Formula A10]
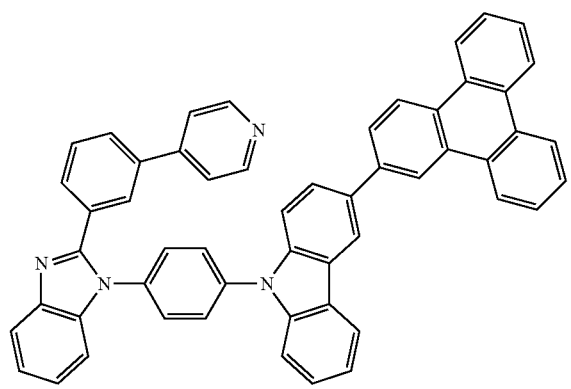
[Chemical Formula A11]
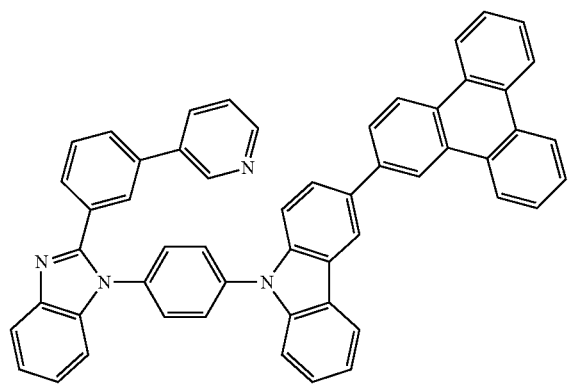
[Chemical Formula A12]
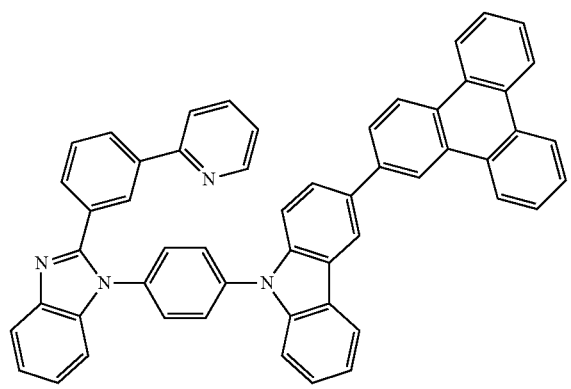
[Chemical Formula A13]
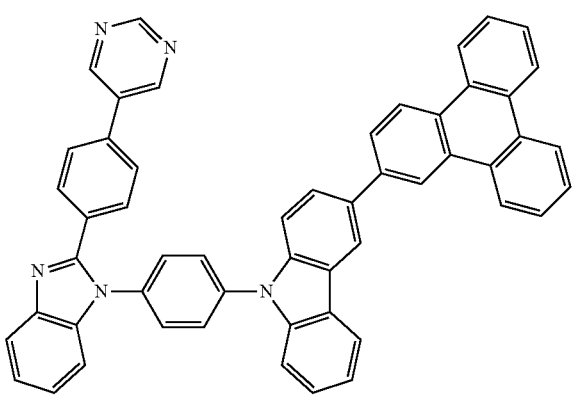
[Chemical Formula A14]
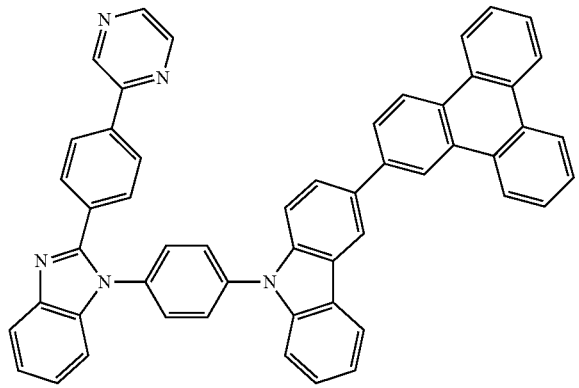
[Chemical Formula A15]
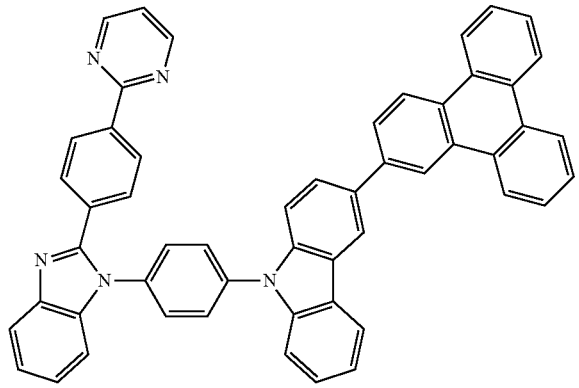
[Chemical Formula A16]
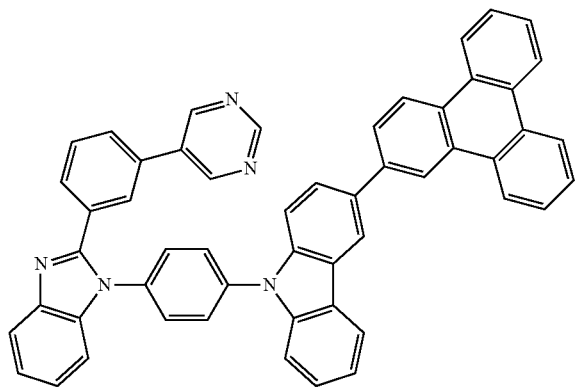
[Chemical Formula A17]
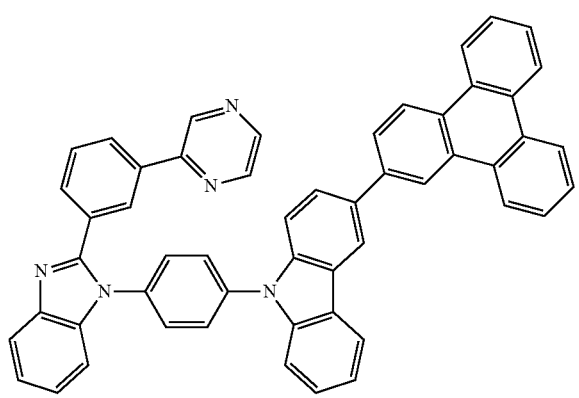

-continued
[Chemical Formula A18]
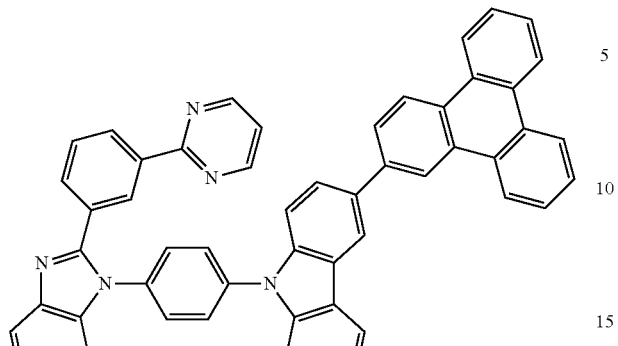
[Chemical Formula A19]
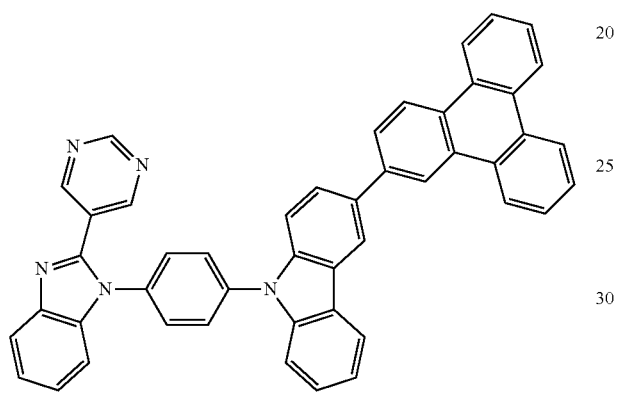
[Chemical Formula A20]
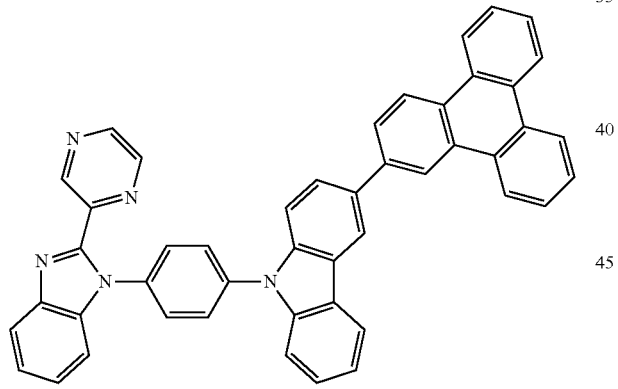
[Chemical Formula A21]
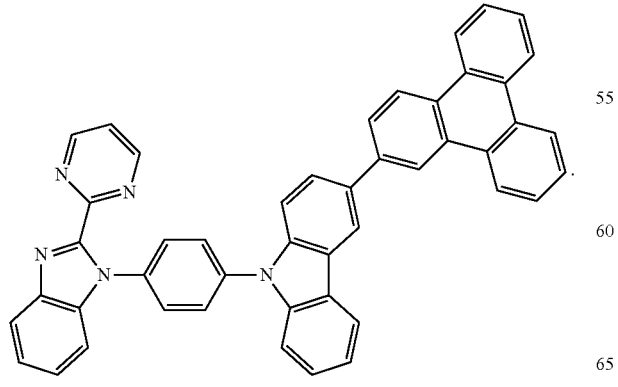
Embodiments are also directed to a compound for an organic optoelectronic device represented by one of the following Chemical Formulae B1 to B42:
[Chemical Formula B1]
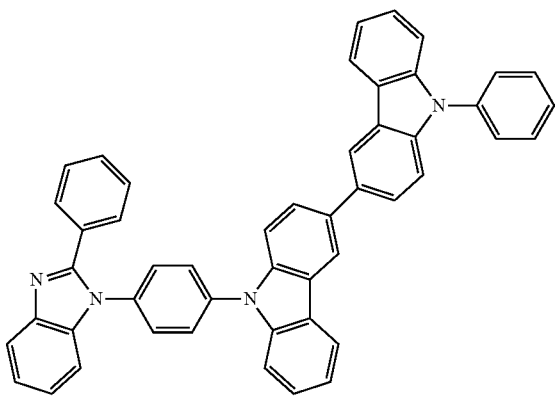
[Chemical Formula B2]
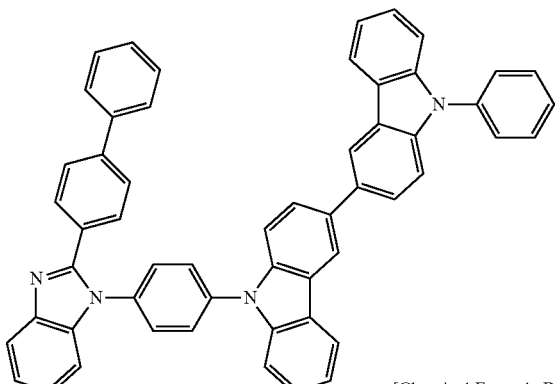
[Chemical Formula B3]
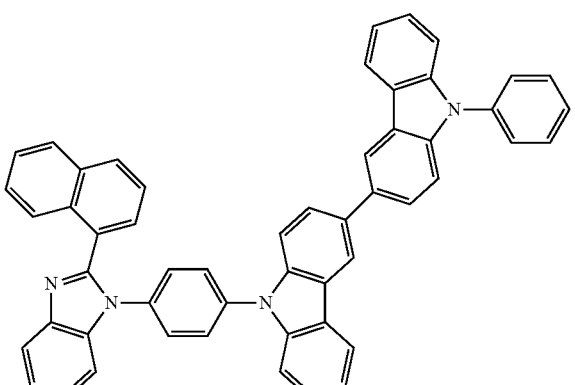
[Chemical Formula B4]
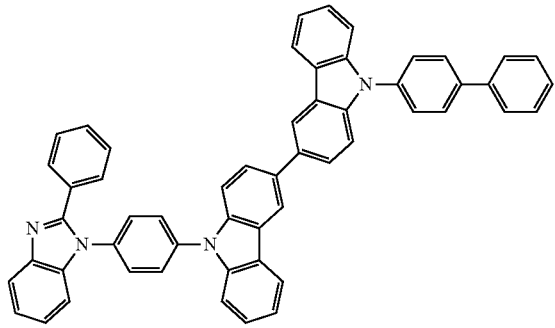

[Chemical Formula B5]
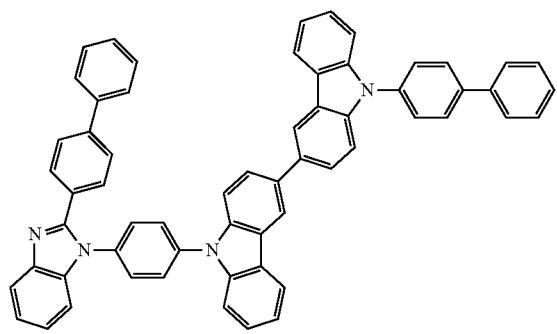
[Chemical Formula B6]
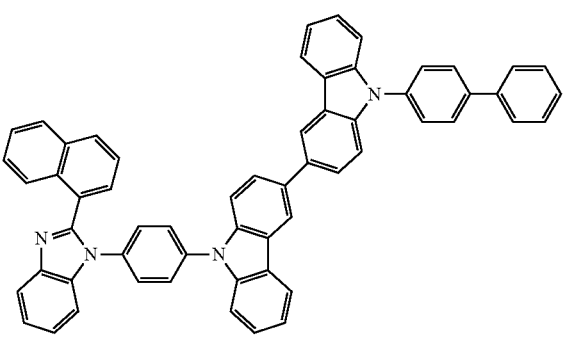
[Chemical Formula B7]
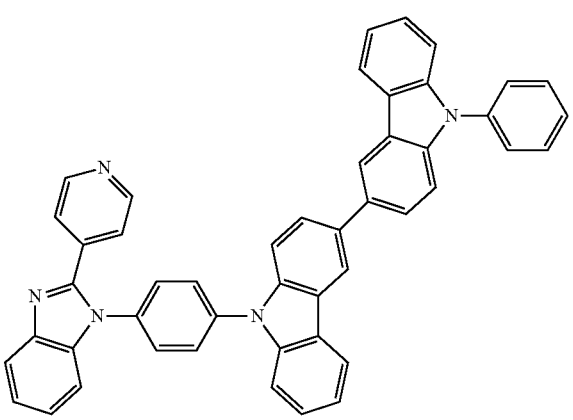
[Chemical Formula B8]
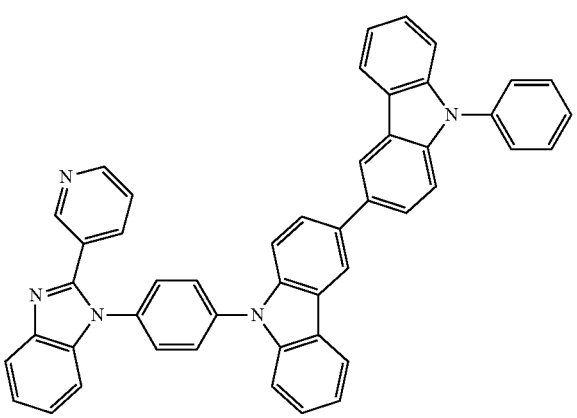
[Chemical Formula B9]
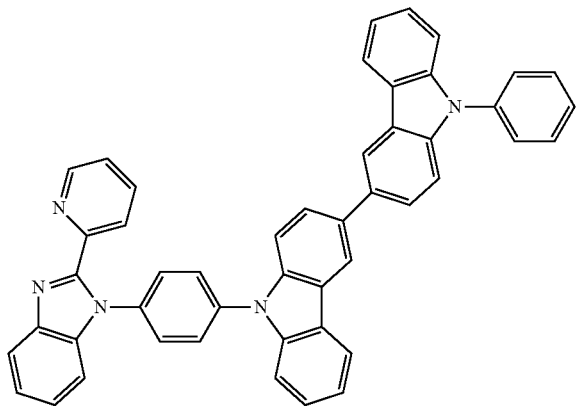
[Chemical Formula B10]
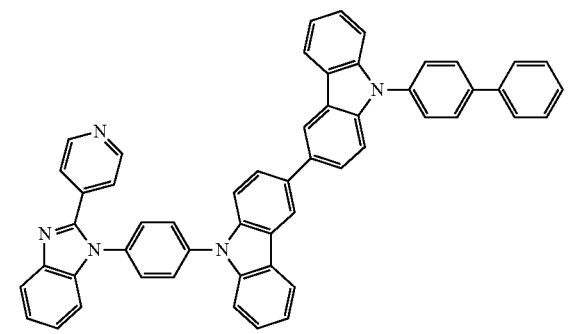
[Chemical Formula B11]
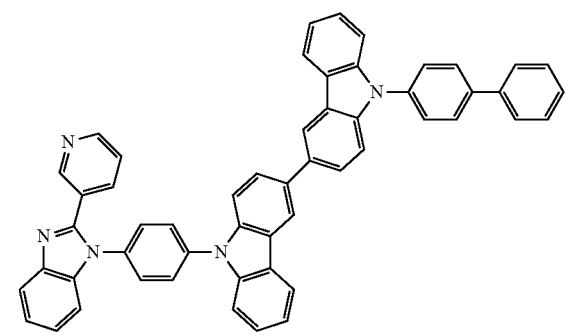
[Chemical Formula B12]
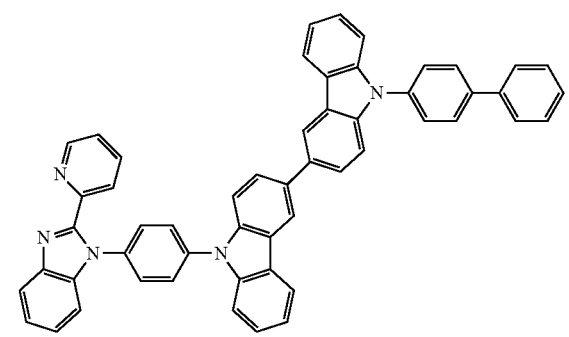

[Chemical Formula B13]
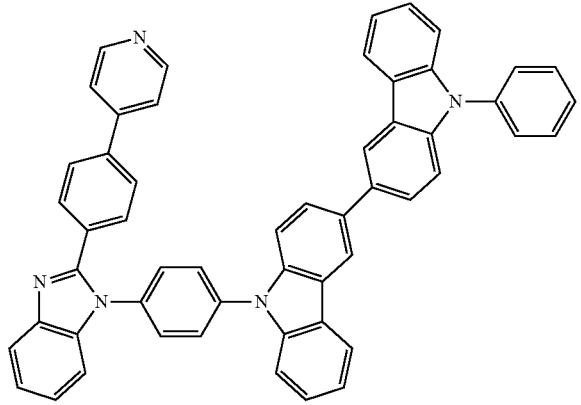
[Chemical Formula B14]
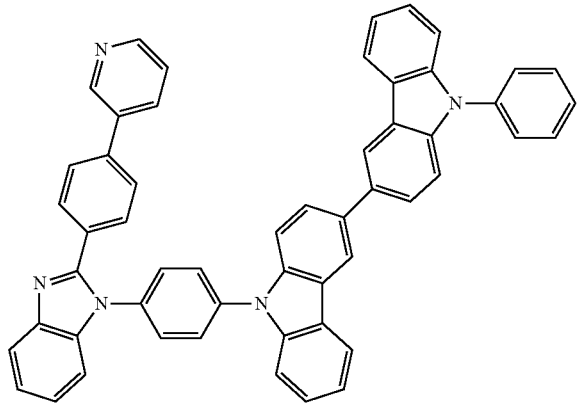
[Chemical Formula B15]
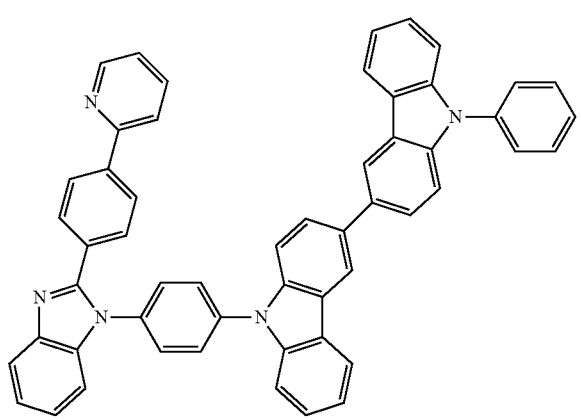
[Chemical Formula B16]
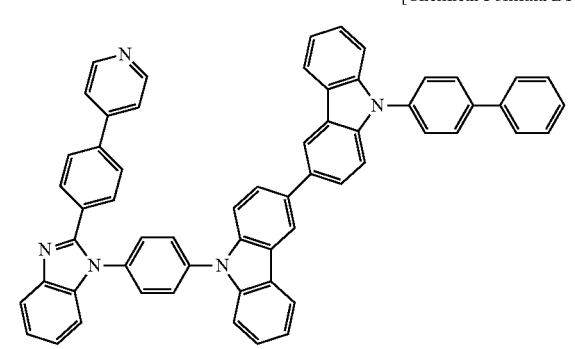
[Chemical Formula B17]
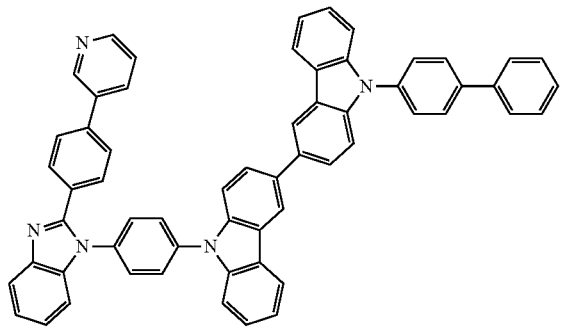
[Chemical Formula B18]
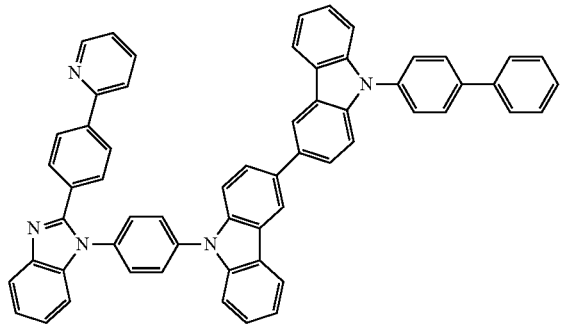
[Chemical Formula B19]
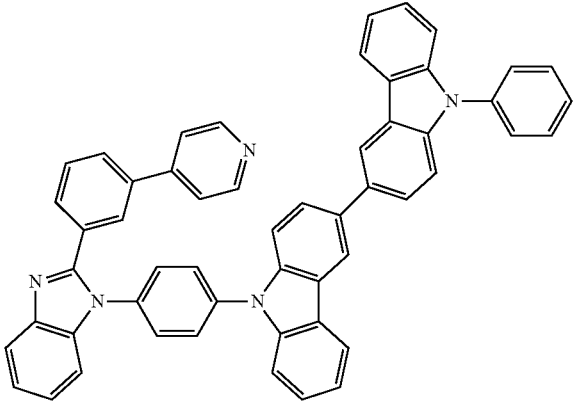
[Chemical Formula B20]
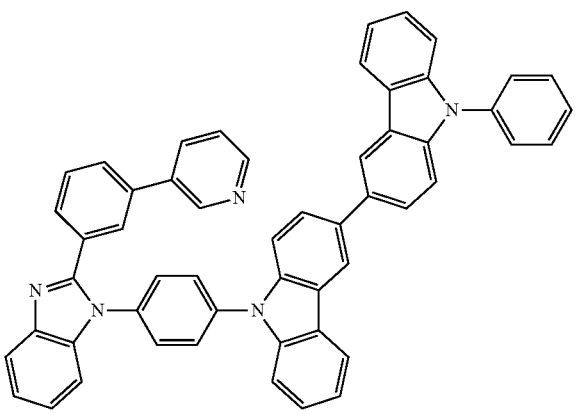

[Chemical Formula B21]
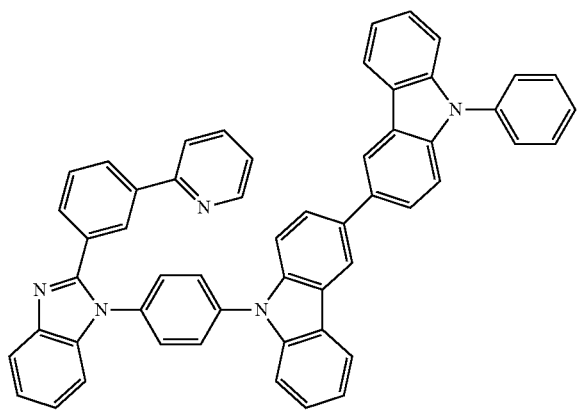
[Chemical Formula B22]
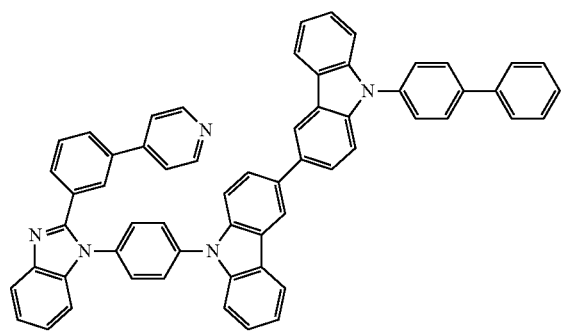
[Chemical Formula B23]
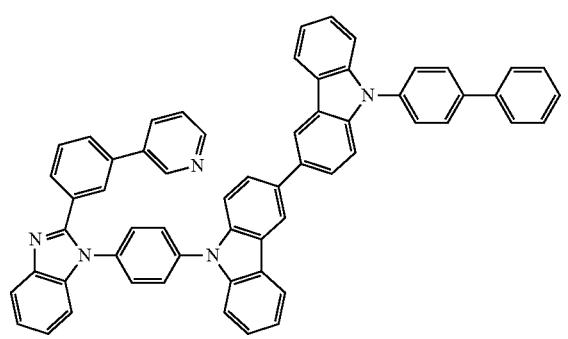
[Chemical Formula B24]
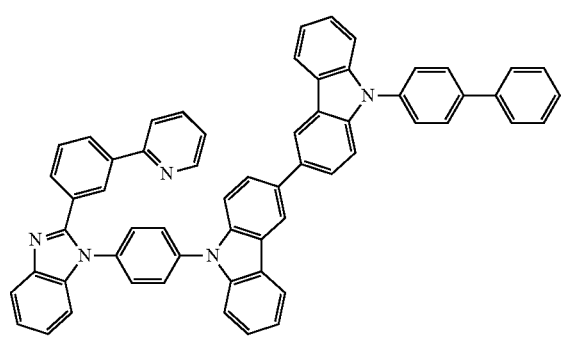
[Chemical Formula B25]
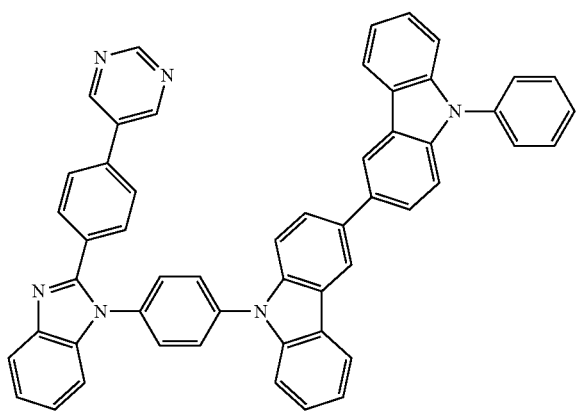
[Chemical Formula B26]
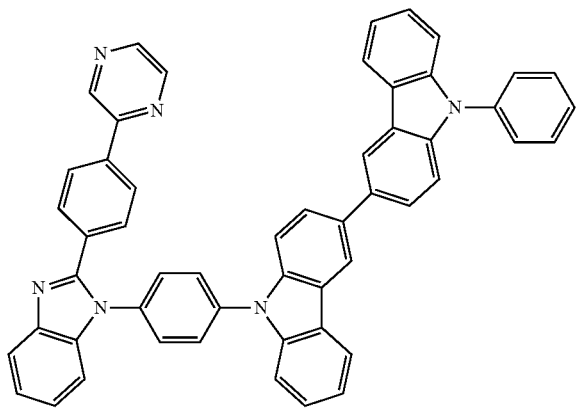
[Chemical Formula B27]
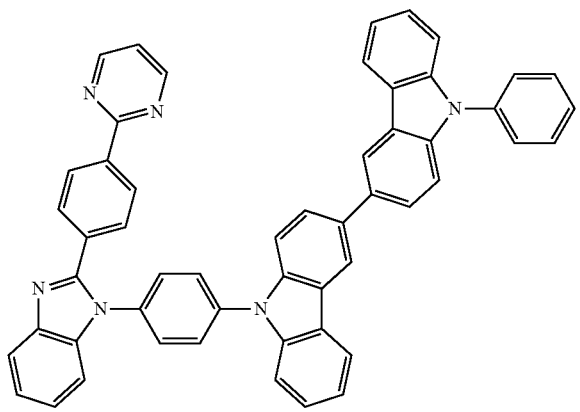
[Chemical Formula B28]
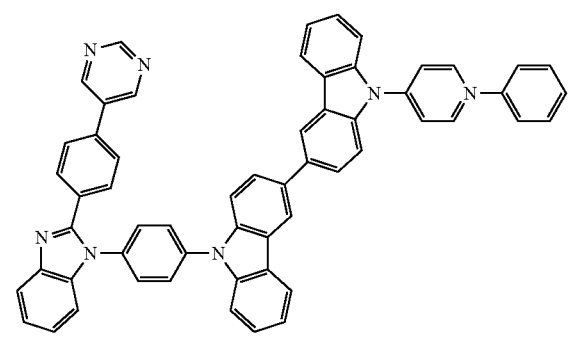

[Chemical Formula B29]
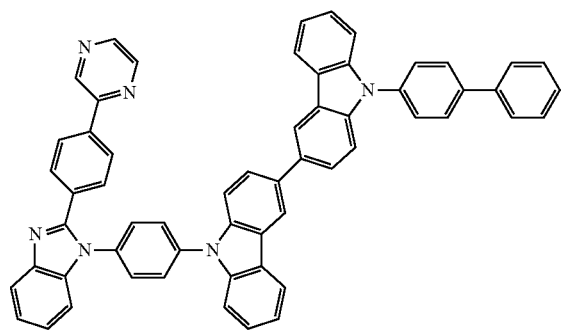
[Chemical Formula B30]
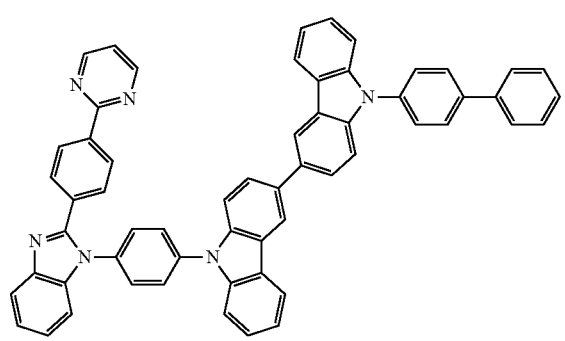
[Chemical Formula B31]
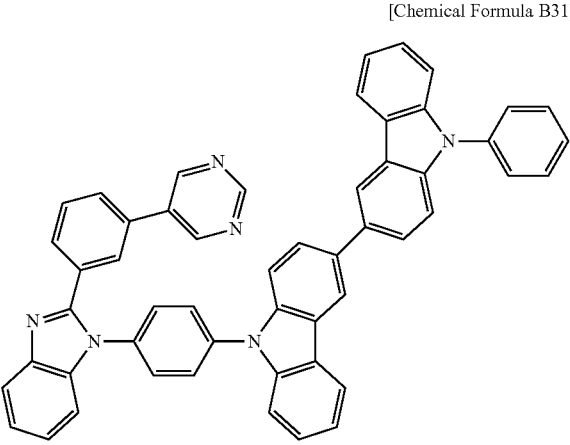
[Chemical Formula B32]
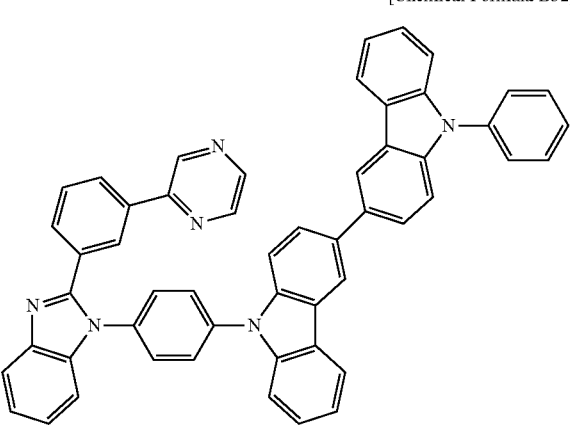
[Chemical Formula B33]
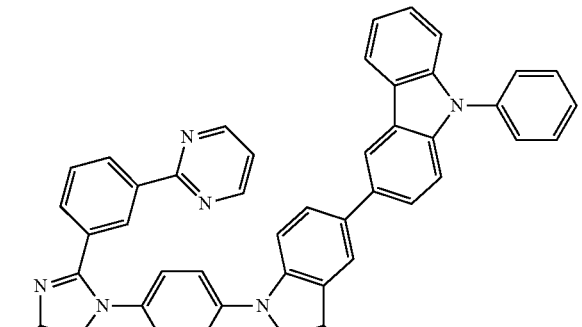
[Chemical Formula B34]
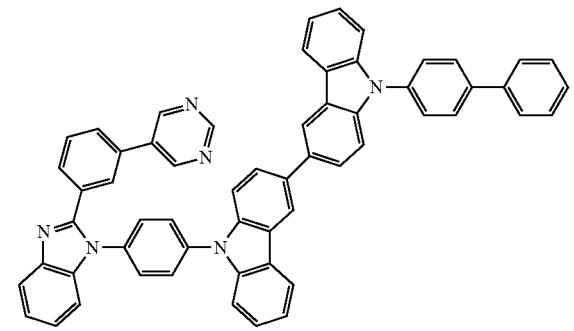
[Chemical Formula B35]
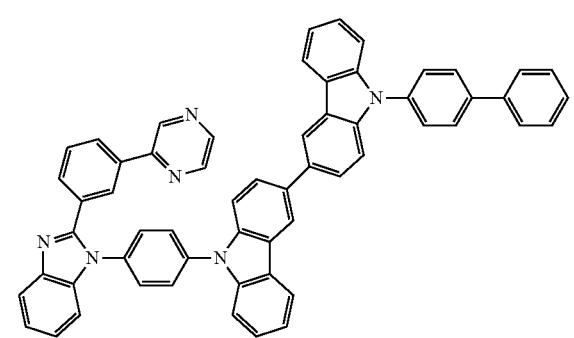
[Chemical Formula B36]

[Chemical Formula B37]
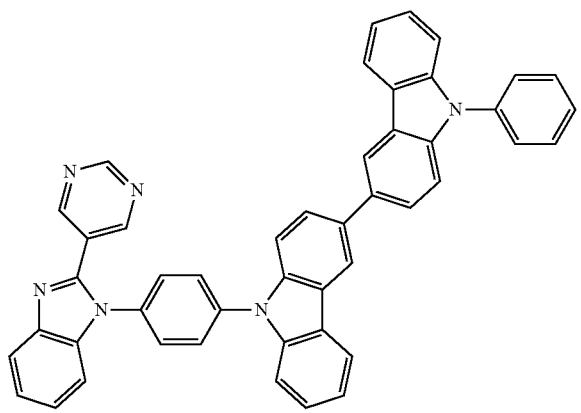
[Chemical Formula B38]
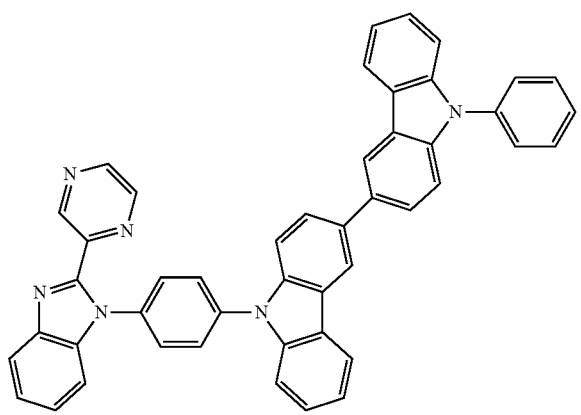
[Chemical Formula B39]
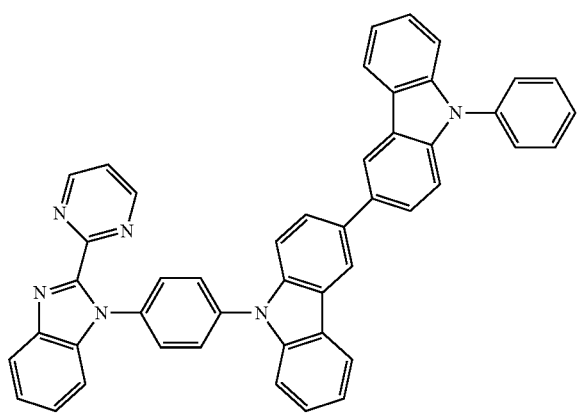
[Chemical Formula B40]
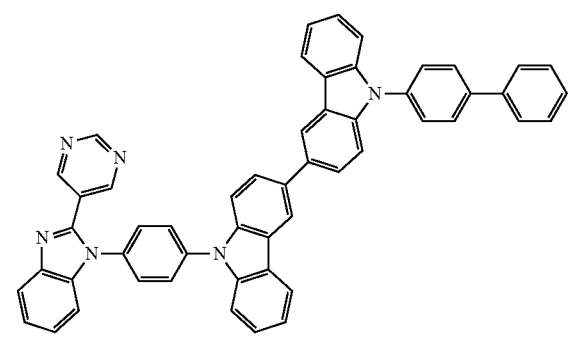
[Chemical Formula B41]
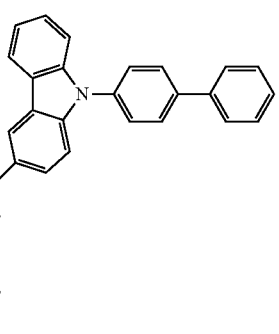
[Chemical Formula B42]
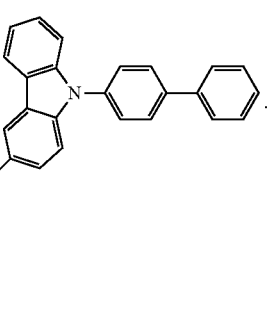
Embodiments are also directed to a compound for an organic optoelectronic device represented by one of the following Chemical Formulae C1 to C42:
[Chemical Formula C1]
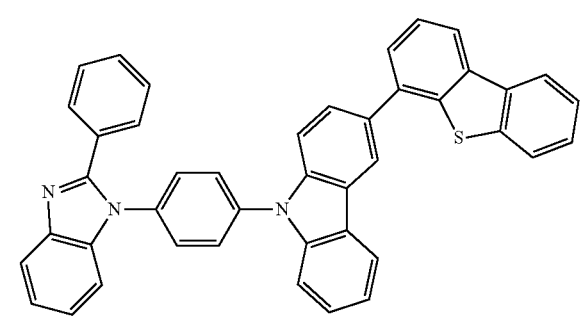
[Chemical Formula C2]
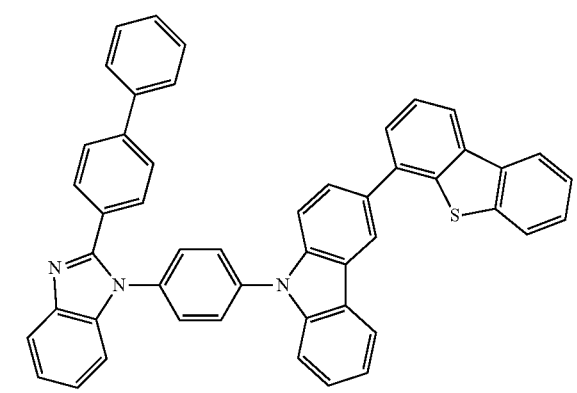

[Chemical Formula C3]
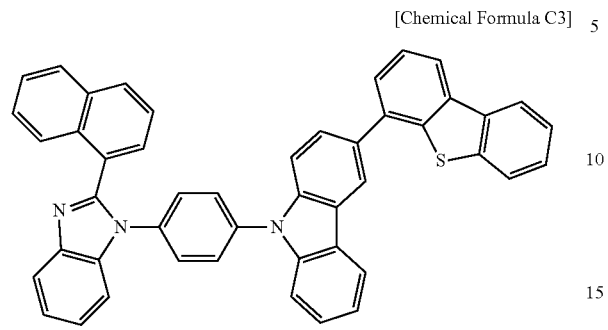
[Chemical Formula C4]
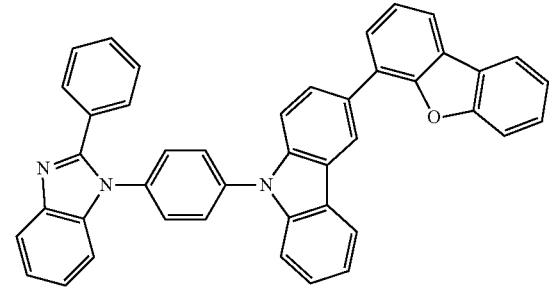
[Chemical Formula C5]
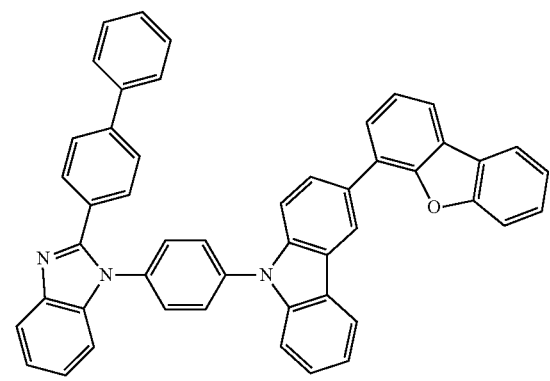
[Chemical Formula C6]
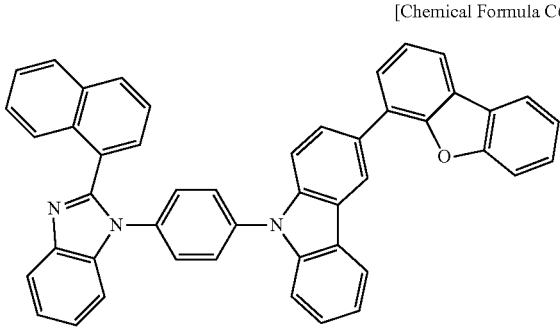
[Chemical Formula C7]
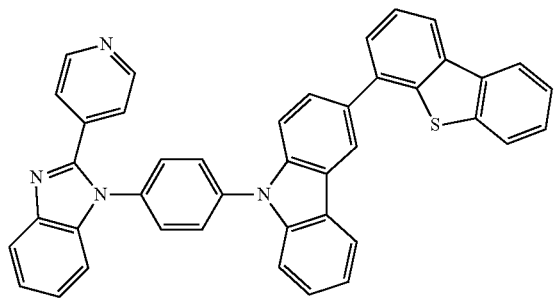
[Chemical Formula C8]
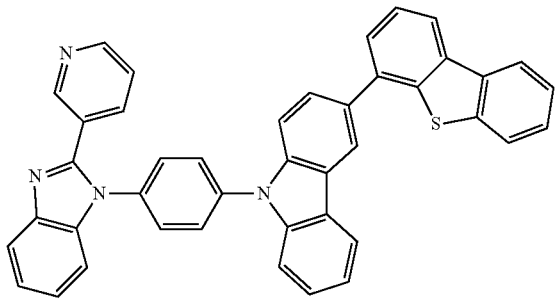
[Chemical Formula C9]
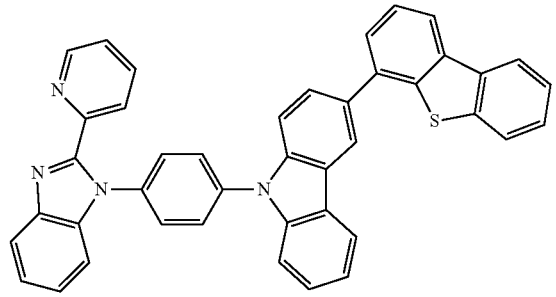
[Chemical Formula C10]
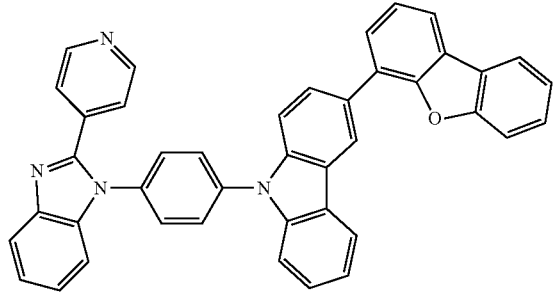
[Chemical Formula [11]
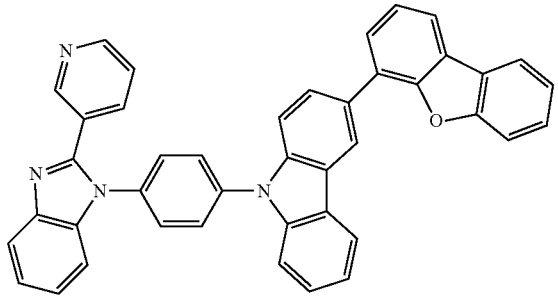

[Chemical Formula C12]
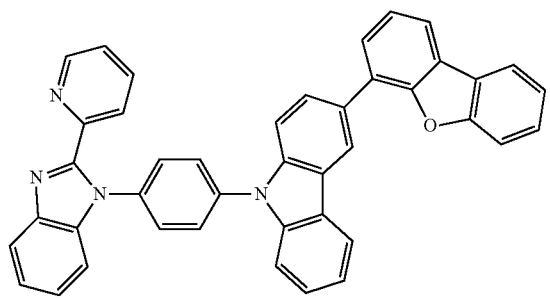
[Chemical Formula C13]
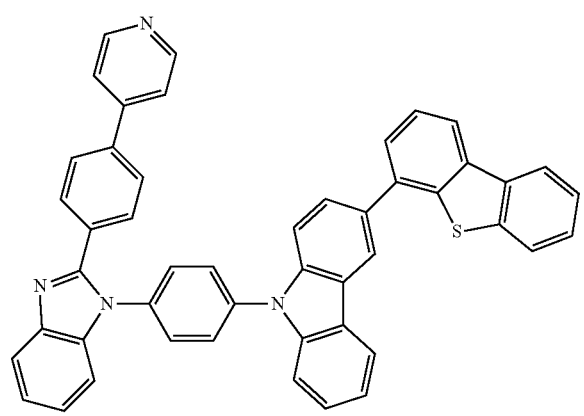
[Chemical Formula C14]
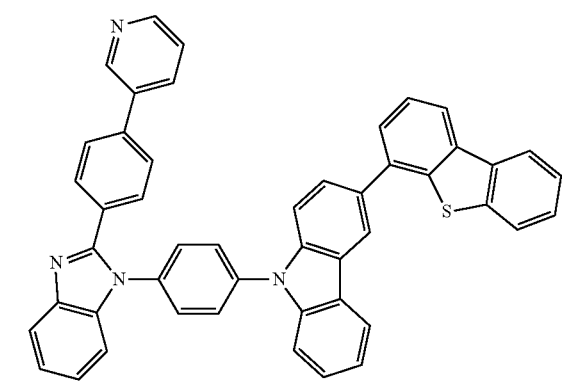
[Chemical Formula C15]
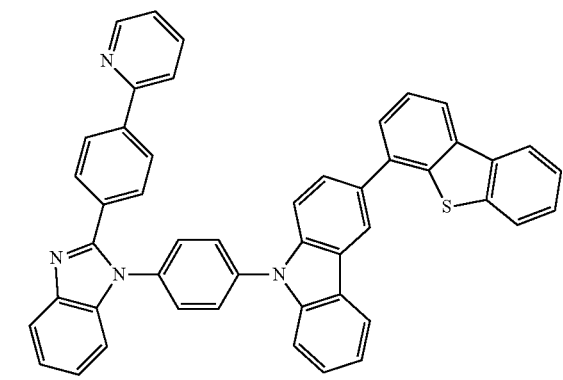
[Chemical Formula C16]
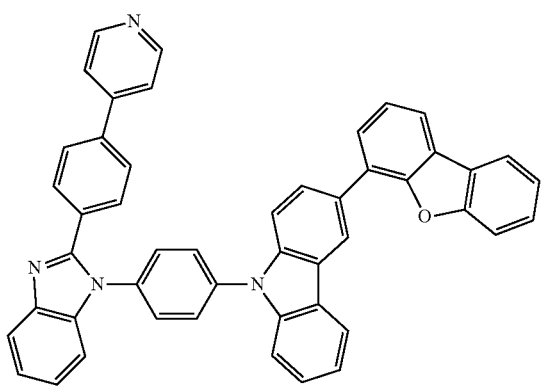
[Chemical Formula C17]
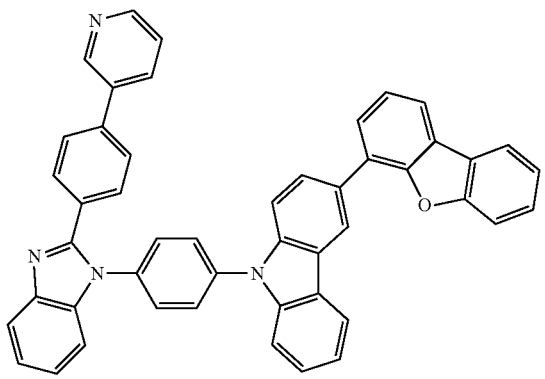
[Chemical Formula C18]
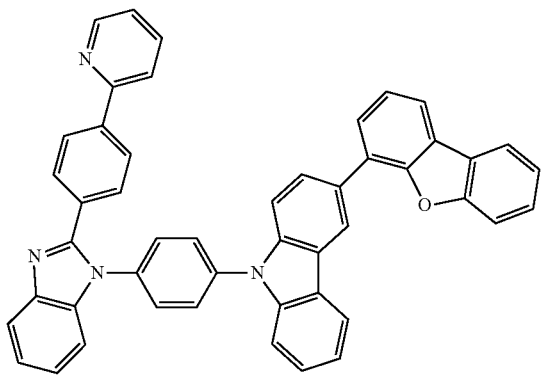
[Chemical Formula C19]
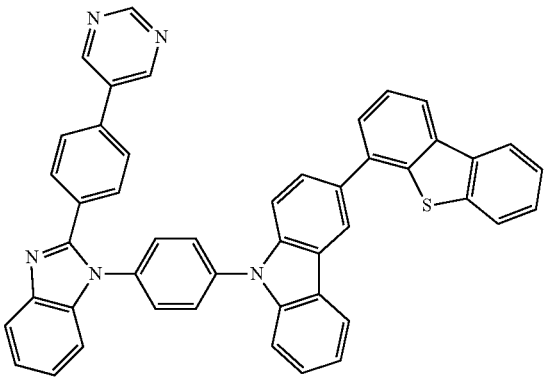

[Chemical Formula C20]
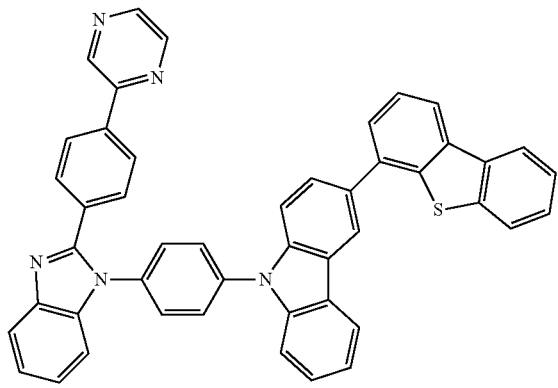
[Chemical Formula C21]
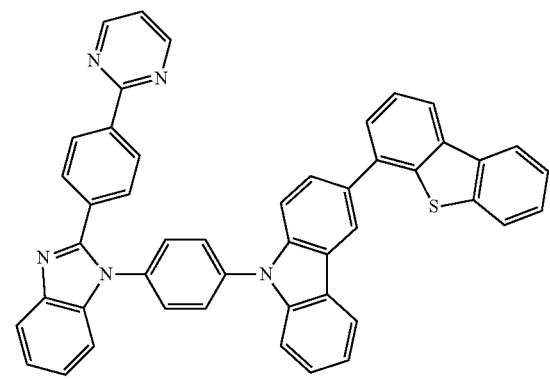
[Chemical Formula C22]
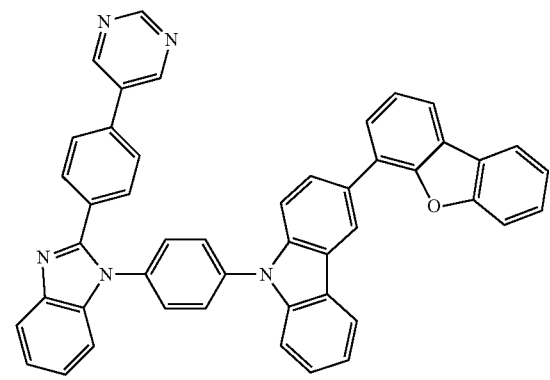
[Chemcial Formula C23]
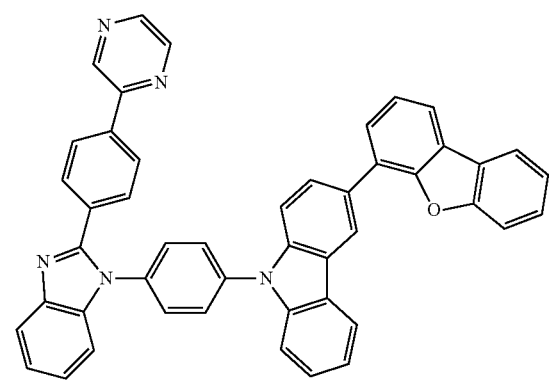
[Chemical Formula C24]
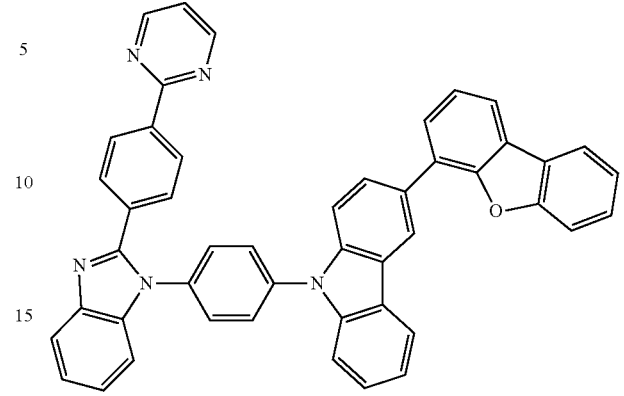
[Chemical Formula C25]
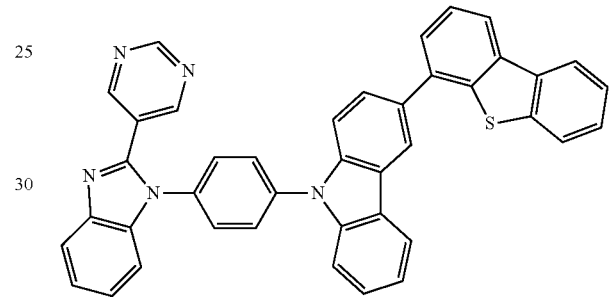
[Chemical Formula C26]
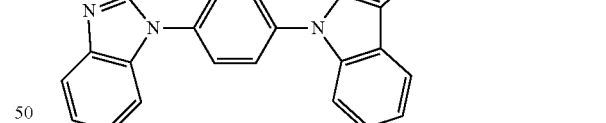
[Chemical Formula C27]
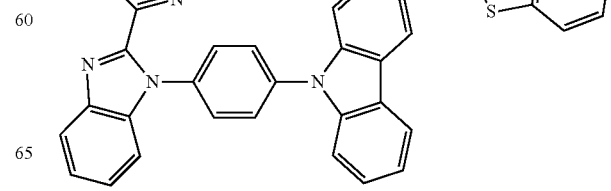

[Chemical Formula C28]
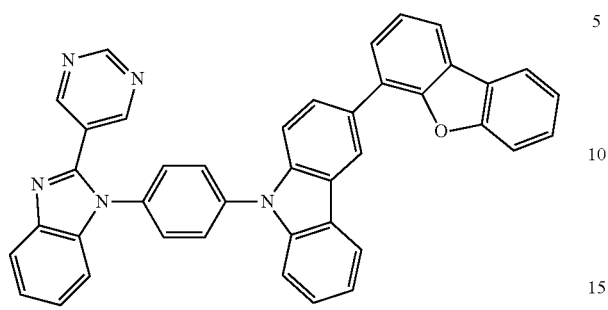
[Chemical Formula C29]
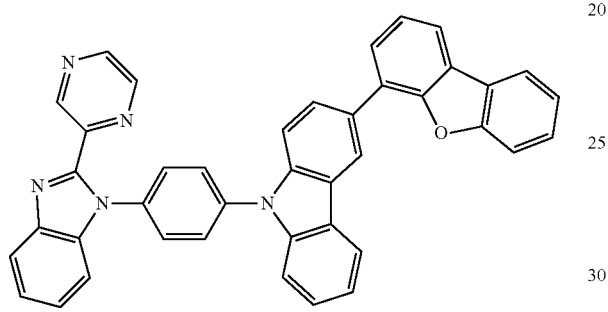
[Chemical Formula C30]
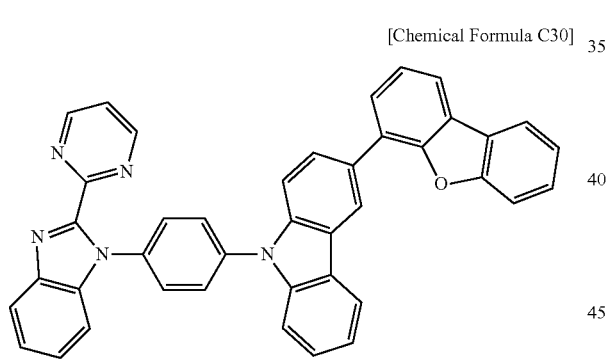
[Chemical Formula C31]
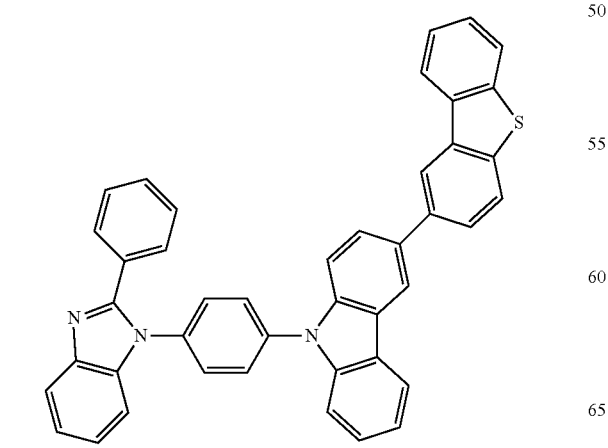
[Chemical Formula C32]
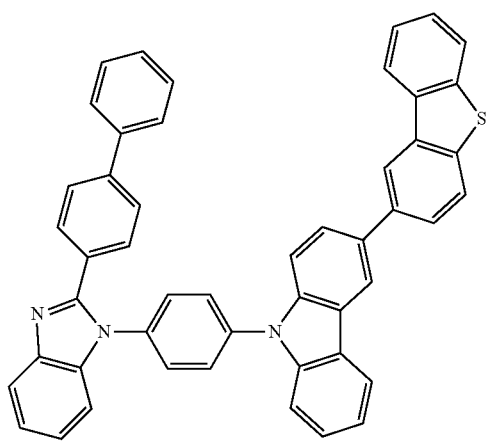
[Chemical Formula C33]
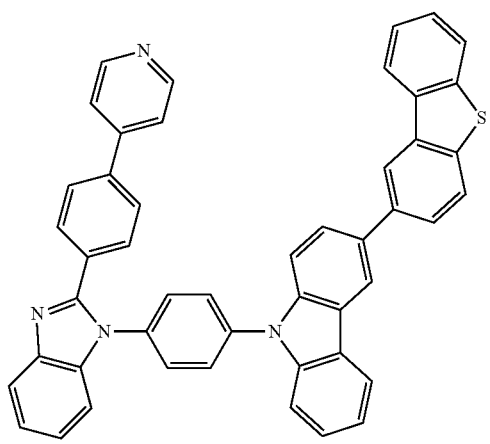
[Chemical Formula C34]
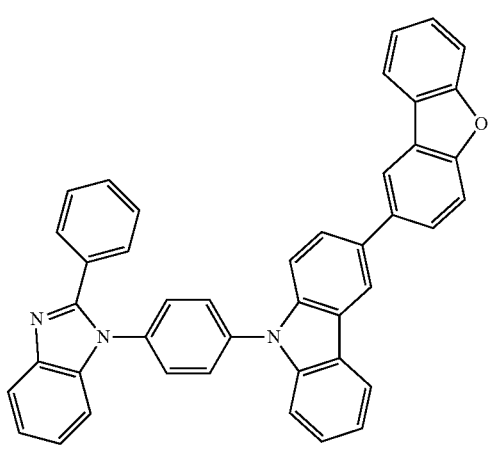

[Chemical Formula C35]
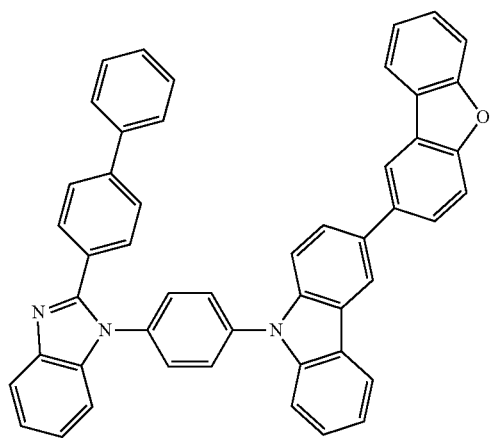
[Chemical Formula C36]
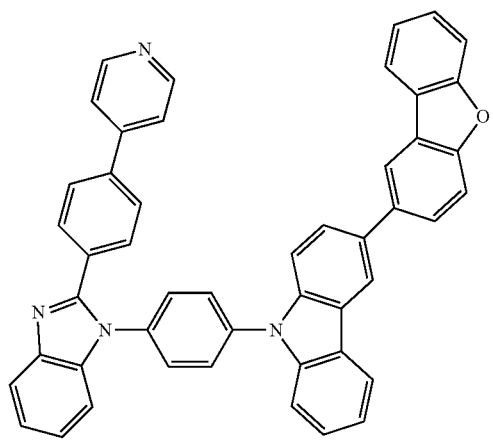
[Chemical Formula C37]
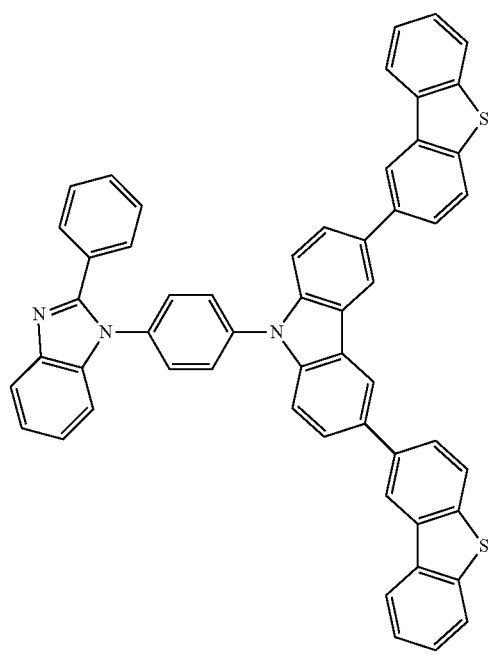
[Chemical Formula C38]
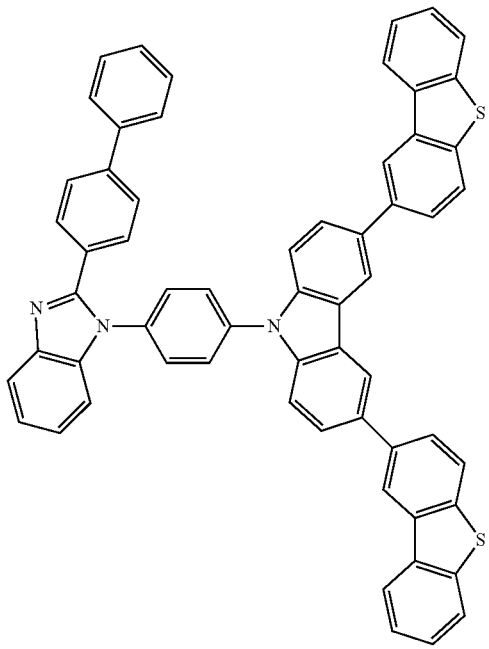
[Chemical Formula C39]
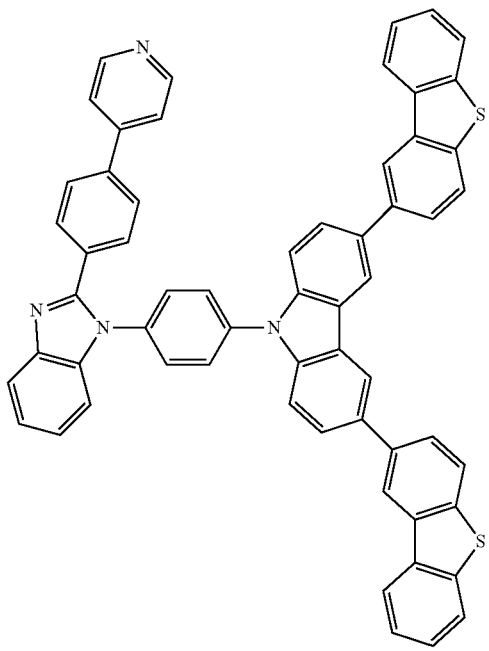

[Chemical Formula C40]

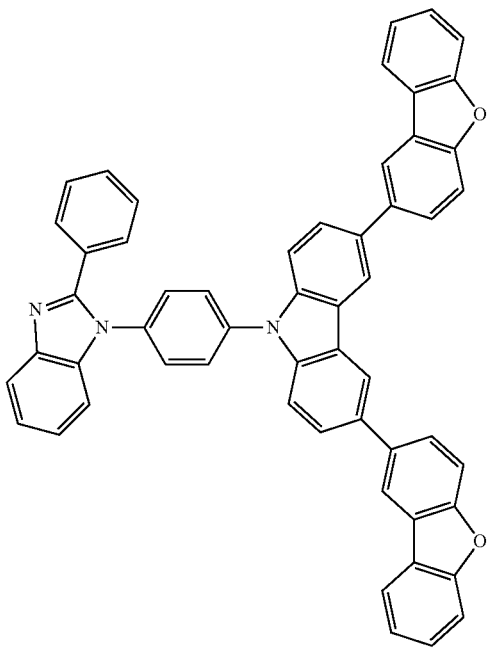

[Chemical Formula C41]

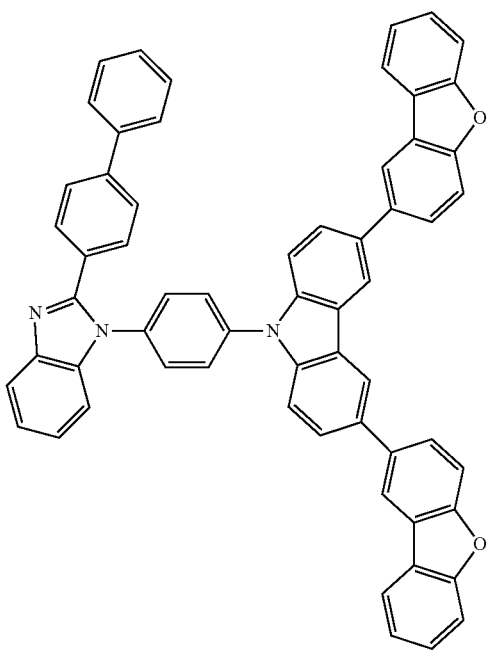

[Chemical Formula C42]

The organic optoelectronic device may be selected from an organic photoelectric device, an organic light emitting diode, organic solar cell, an organic transistor, an organic photo conductor drum, and an organic memory device.

Embodiments are also directed to an organic light emitting diode, including an anode, a cathode, and one or more organic thin layers between the anode and the cathode. At least one of the organic thin layers may include a compound for an organic optoelectronic device according to an embodiment.

The organic thin layer may be an emission layer, a hole transport layer, a hole injection layer, an electron transport layer, an electron injection layer, a hole blocking layer, or a combination thereof.

The compound for an organic optoelectronic device may be included in an emission layer.

The compound for an organic optoelectronic device may be a phosphorescent or fluorescent host material in an emission layer.

The compound for an organic optoelectronic device may be a material of a hole transport layer, a hole injection layer, an electron transport layer, an electron injection layer, or a hole blocking layer.

BRIEF DESCRIPTION OF THE DRAWINGS

Features will become apparent to those of skill in the art by describing in detail example embodiments with reference to the attached drawings in which.

DETAILED DESCRIPTION

Figure 1:
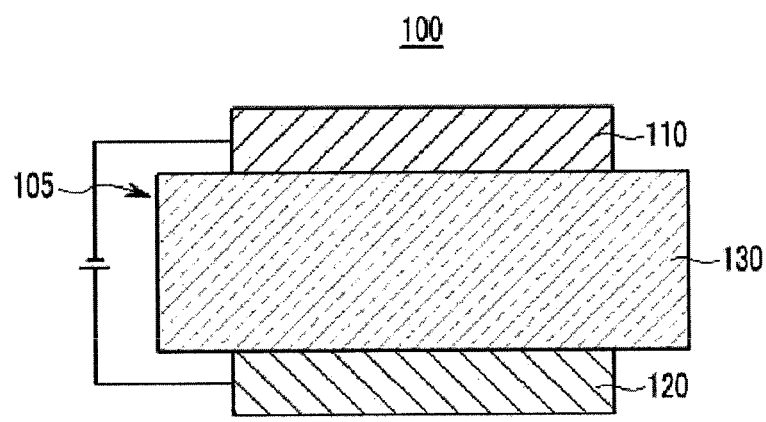
FIGS. 1 to 5 illustrate cross-sectional views showing organic light emitting diodes according to example embodiments including a compound for an organic optoelectronic device according to an embodiment.

Example embodiments will now be described more fully hereinafter with reference to the accompanying drawings;

however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

In the present specification, when specific definition is not otherwise provided, "substituted" refers to one substituted with a C1 to C30 alkyl group, a C1 to C10 alkylsilyl group, a C3 to C30 cycloalkyl group, a C6 to C30 aryl group, a C1 to C10 alkoxy group, a fluoro group, a C1 to C10 trifluoroalkyl group such as a trifluoromethyl group and the like, or a cyano group.

In the present specification, when specific definition is not otherwise provided, "hetero" refers to one including 1 to 3 hetero atoms selected from N, O, S, and P, and remaining carbons in one compound or substituent.

In the present specification, when a definition is not otherwise provided, "combination thereof" refers to at least two substituents bound to each other by a linker, or at least two substituents condensed to each other.

In the present specification, when a definition is not otherwise provided, "alkyl group" refers to an aliphatic hydrocarbon group. The alkyl group may be "a saturated alkyl group" that does not any alkene group or alkyne group. The alkyl group may be "an unsaturated alkyl group" that includes at least one alkene group or alkyne group. The "alkene group" refers to a functional group of at least one carbon-carbon double bond of at least two carbons, and the "alkyne group" refers to a functional group of at least one carbon-carbon triple bond of at least two carbons. Regardless of being saturated or unsaturated, the alkyl group may be branched, linear or cyclic.

The alkyl group may be a C1 to C20 alkyl group. The alkyl group may be a C1 to C10 medium-sized alkyl group. The alkyl group may be a C1 to C6 lower alkyl group.

For example, a C1 to C4 alkyl group may have 1 to 4 carbon atoms in an alkyl chain which may be selected from methyl, ethyl, propyl, iso-propyl, n-butyl, iso-butyl, sec-butyl, and t-butyl.

Typical examples of alkyl group may be individually and independently a functional group substituted with one or more selected from a methyl group, an ethyl group, a propyl group, an isopropyl group, a butyl group, an isobutyl group, a t-butyl group, a pentyl group, a hexyl group, an ethenyl group, a propenyl group, a butenyl group, a cyclopropyl group, a cyclobutyl group, a cyclopentyl group, a cyclohexyl group, or the like.

"Aromatic group" refers to a cyclic functional group where all elements have p-orbitals, and these p-orbitals forms conjugation. Specific examples are aryl group and a heteroaryl group.

"Aryl group" includes monocyclic or fused ring polycyclic (i.e., rings sharing adjacent pairs of carbon atoms) groups.

"Heteroaryl group" refers to aryl group including 1 to 3 hetero atoms selected from N, O, S, and P, and remaining carbons.

"Spiro structure" refers to a plurality of cyclic structures having a contact point of one carbon. The spiro structure may include a compound having a spiro structure or a substituent having a spiro structure.

According to embodiments, an organic optoelectronic device may include an organic compound and a device to convert light into electricity and/or a device to convert electricity into light.

A compound for an organic optoelectronic device according to an example embodiment has a structure where a core includes a substituted or unsubstituted imidazole group and a substituted or unsubstituted carbazolyl group, and a substituent having hole characteristics is bonded with the core.

According to the present example embodiment, the compound including the core structure may have excellent electron characteristics selectively reinforced by hole characteristics, and thus may be satisfactory for use in an emission layer. For example, the compound may be used as a host material of an emission layer.

The compound for an organic optoelectronic device may include a core part and various substituents for a substituent for substituting the core part, and thus may have various energy bandgaps. The compound may be used in a hole transport layer, a hole injection layer, an electron transport layer, an electron injection layer, or a hole blocking layer.

The compound may have an appropriate energy level depending on the substituents, and thus may fortify electron transfer capability of an organic optoelectronic device and bring about excellent effects on efficiency and driving voltage and also, have excellent electrochemical and thermal stability, and thus improve life-span characteristics during the operation of the organic optoelectronic device.

According to an example embodiment, a compound for an organic optoelectronic device represented by the following Chemical Formula 1 is provided.

[Chemical Formula 1]

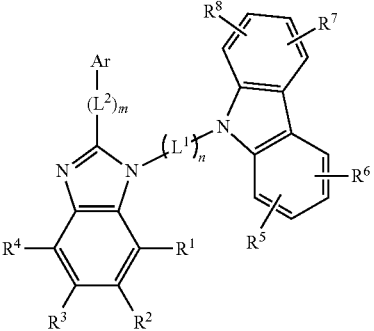

According to the present example embodiment, in the above Chemical Formula 1, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^8$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and at least one of $R^5$ to $R^8$ is a substituted or unsubstituted C3 to C30 heteroaryl group having hole characteristics, a substituted or unsubstituted C6 to C30 aryl group having hole characteristics, a substituted or unsubstituted arylamine group having hole characteristics, or a combination thereof.

The hole characteristics refer to characteristics that a hole formed in the anode is easily injected into the emission layer and transported in the emission layer due to conductive characteristics according to HOMO level.

Electron characteristics, as compared to the hole characteristics, refer to characteristics that an electron formed in the cathode is easily injected into the emission layer and transported in the emission layer due to conductive characteristics according to LUMO level.

As an example of the substituted or unsubstituted C6 to C30 aryl group having hole characteristics, at least one of the $R^5$ to $R^8$ may be a substituted or unsubstituted triphenylenyl group.

The triphenylenyl group of the compound has a bulky structure and may cause a resonance effect, and thus may suppress a side reaction possibly occurring in a solid state and improve performance of an organic light emitting diode.

In addition, the triphenylenyl group may make the compound bulky, and thus may have an effect on lowering crystallinity and increasing life-span.

The triphenylenyl group may have a wider band gap and high triplet excitation energy that other substituents, and thus when bonded with carbazole may does not decrease the band gap or triplet excitation energy of the compound.

According to an example embodiment, the compound for an organic optoelectronic device may be represented by the following Chemical Formula 2.

[Chemical Formula 2]

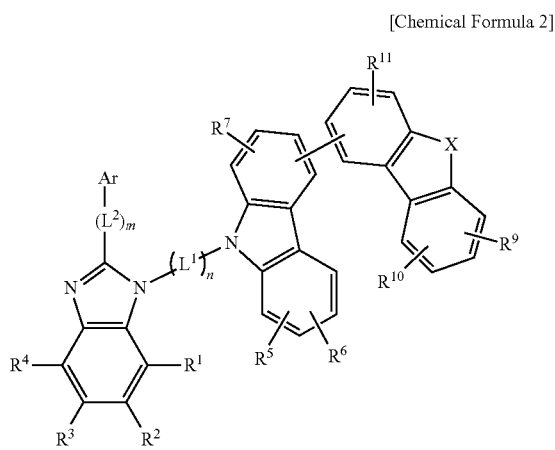

According to the present example embodiment, in the above Chemical Formula 2, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^7$ and $R^9$ to $R^{11}$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X is NR', O, or S, wherein the R' is hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The compound represented by the above Chemical Formula 2 may be a structure including a substituted or unsubstituted carbazole-based derivative, a substituted or unsubstituted dibenzofuranyl-based derivative, or a substituted or unsubstituted dibenzothiophenyl-based derivative.

In the present example embodiment, the carbazolyl-based derivative may include more than two substituents bonded with a carbazolyl group and forming a fused ring, as may the dibenzofuranyl-based derivative and the dibenzothiophenyl-based derivative.

When the carbazolyl-based derivative, dibenzofuranyl-based derivative, or dibenzothiophenyl-based derivative is included in a compound, bi-polar characteristics of the entire compound may be improved.

The compound represented by the above Chemical Formula 2 may include the carbazole-based derivative, which may help provide hole characteristics when used for an organic optoelectronic device.

In an example embodiment, the $L^1$ and $L^2$ may independently be a substituted or unsubstituted ethenylene, a substituted or unsubstituted ethynylene, a substituted or unsubstituted phenylene, a substituted or unsubstituted biphenylene, a substituted or unsubstituted naphthalene, a substituted or unsubstituted pyridinylene, a substituted or unsubstituted pyrimidinylene, a substituted or unsubstituted triazinylene, or the like.

A substituent having a pi-bond of the substituents may increase a triplet energy bandgap by controlling the total π-conjugation length of compound, which may enable use for the emission layer of organic optoelectronic device as a phosphorescent host. Where the n and m are independently 0, the linking groups such as the $L^1$ and $L^2$ may not be present.

The n may be 1, and the m may be 0 or 1. When such a combination of n and m satisfy the above, the compound for an organic optoelectronic device according to an example embodiment may have various energy levels.

According to an example embodiment, the $L^1$ and $L^2$ may be a substituted or unsubstituted carbazolyl-based derivative, a substituted or unsubstituted dibenzothiophenyl-based derivative, a substituted or unsubstituted dibenzofuranyl-based derivative, or the like. A linking group itself may have hole characteristics, and the substituent may further reinforce the hole characteristics of the entire compound. In addition, a pi bond may be selectively adjusted depending on bonding position of the carbazolyl-based derivative, and an energy bandgap of the entire compound may be adjusted.

According to an example embodiment, the $L^1$ may be a substituted or unsubstituted phenylene group. When the $L^1$ is a substituted or unsubstituted phenylene group, the compound for an organic optoelectronic device according to an example embodiment may be easily synthesized.

According to an example embodiment, the compound for an organic optoelectronic device may be represented by the following Chemical Formula 3 or 4.

[Chemical Formula 3]

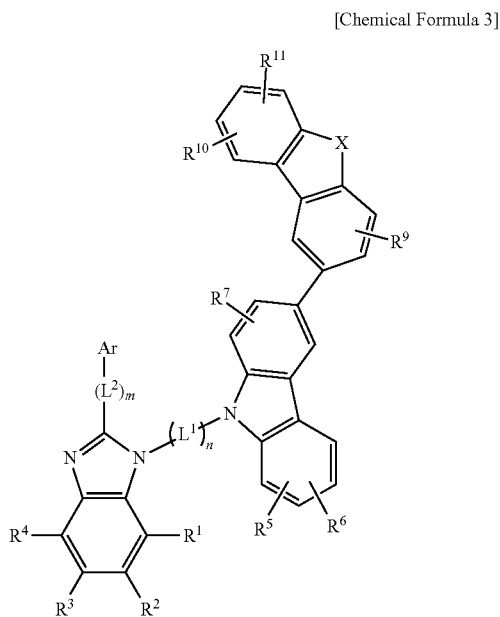

According to the present example embodiment, in the above Chemical Formula 3, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^7$ and $R^9$ to $R^{11}$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X is NR', O, or S, wherein the R' is hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

[Chemical Formula 4]

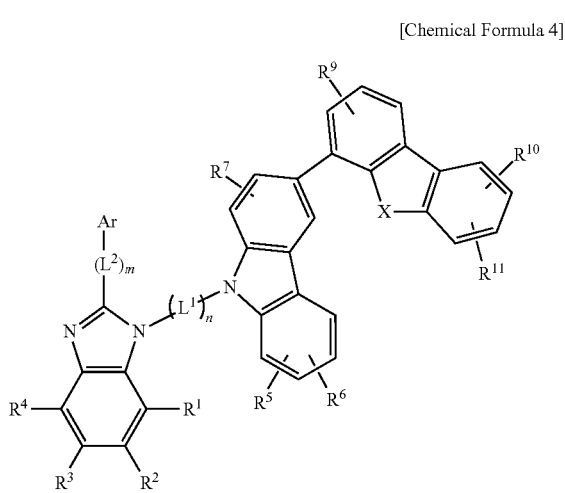

According to the present example embodiment, in the above Chemical Formula 4, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^7$ and $R^9$ to $R^{11}$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X is NR', O, or S, wherein the R' is hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

The Ar may be a substituted or unsubstituted C6 to C30 aryl group, a substituted or unsubstituted C3 to C30 heteroaryl group, or a combination thereof.

For example, the Ar may be a substituted or unsubstituted phenyl group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted biphenyl group, a substituted or unsubstituted pyridinyl group, a substituted or unsubstituted pyridinyl group, a substituted or unsubstituted triazinyl group, or a combination thereof.

For example, the Ar may be a substituted or unsubstituted biphenyl group, a substituted or unsubstituted pyridinyl group, a substituted or unsubstituted pyrimidinyl group, a substituted or unsubstituted triazinyl group, or a combination thereof.

For example, when the Ar is a substituted or unsubstituted biphenyl group, the compound for an organic optoelectronic device may have an appropriate energy level and thermal stability.

For example, when the Ar is a substituted or unsubstituted pyridinyl group, electron mobility of the compound may be controlled according to a substitution position of the pyridinyl group, and a device including the compound including the pyridinyl group may have improved efficiency characteristics.

For example, when the Ar is a substituted or unsubstituted triazinyl group, the compound for an organic optoelectronic device may have improved electron mobility characteristics.

The substituted or unsubstituted C3 to C30 heteroaryl group having hole characteristics may be a substituted or unsubstituted carbazolyl-based derivative, a substituted or unsubstituted dibenzofuranyl-based derivative, a substituted or unsubstituted dibenzothiophenyl-based derivative, or a combination thereof.

The substituted or unsubstituted C6 to C30 aryl group having hole characteristics may be a substituted or unsubstituted fluorenyl group, a substituted or unsubstituted spiro-fluorenyl group, or a combination thereof.

The substituted or unsubstituted arylamine group having hole characteristics may include a single aryl group or a plurality of aryl groups. In an implementation, the substituted or unsubstituted arylamine group having hole characteristics may be an amine that includes a single aryl group or a plurality of aryl groups. The single aryl group or a plurality of aryl groups may be the same or different, and may independently be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, or a combination thereof. Such arylamine group may provide enhanced hole characteristics. In an implementation, the arylamine group having hole characteristics may be a triphenylamino group.

Through control of the substituent, energy bandgap of a compound may be controlled. For example, a compound having appropriate characteristics for an emission layer of an organic light emitting diode may be prepared.

In addition, an appropriate combination of the substituents may provide a compound having excellent thermal stability or resistance against oxidation.

An appropriate combination of the substituents may provide a compound having asymmetric bipolar characteristics. The asymmetric bipolar characteristics may improve hole and electron transport capability, and thus luminous efficiency and performance of a device.

In addition, the substituents may be adjusted to make the structure of a compound bulky, and thus decrease crystallinity of the compound. A compound having low crystallinity may improve life-span of a device.

According to an example embodiment, a compound for an organic optoelectronic device may be represented by, e.g., the following Chemical Formulae A1 to A21.

[Chemical Formula A1]

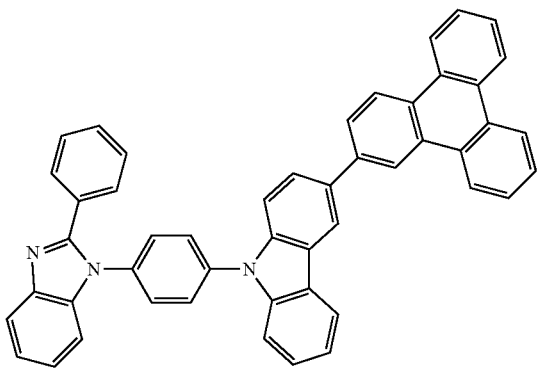

[Chemical Formula A2]

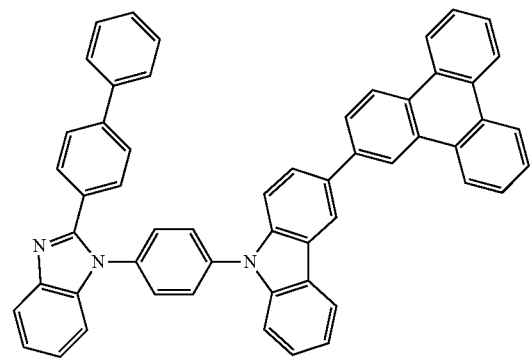

[Chemical Formula A3]

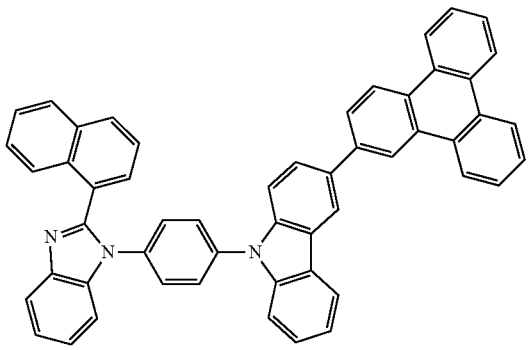

[Chemical Formula A4]

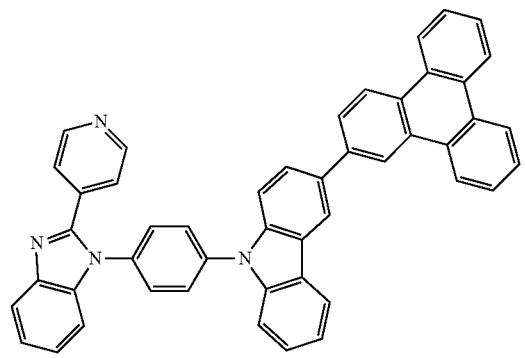

[Chemical Formula A5]

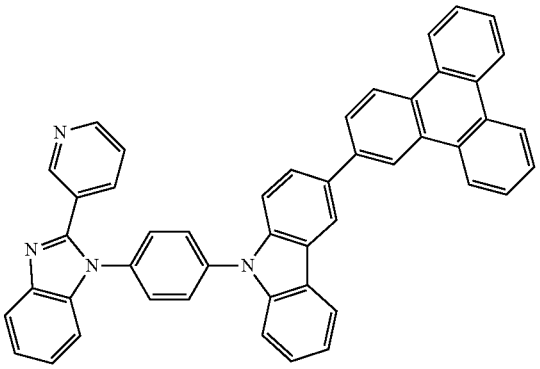

[Chemical Formula A6]

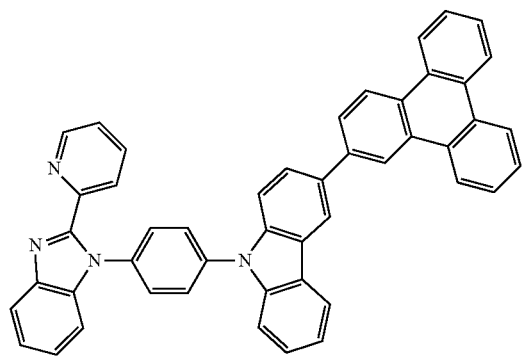

[Chemical Formula A7]

[Chemical Formula A8]

[Chemical Formula A9]

[Chemical Formula A10]

[Chemical Formula A11]

[Chemical Formula A12]

[Chemical Formula A13]

[Chemical Formula A14]

[Chemical Formula A15]
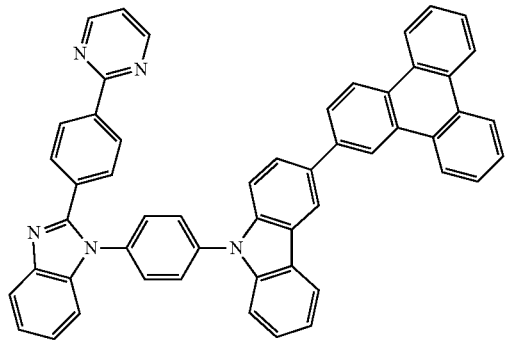
[Chemical Formula A16]
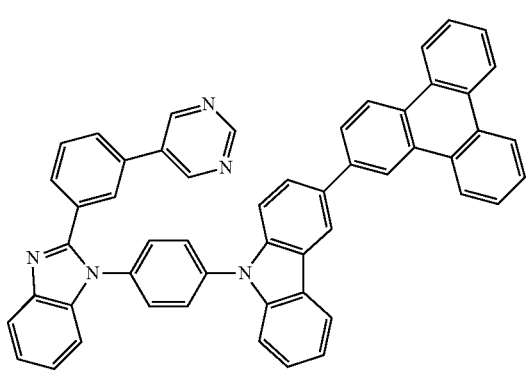
[Chemical Formula A17]
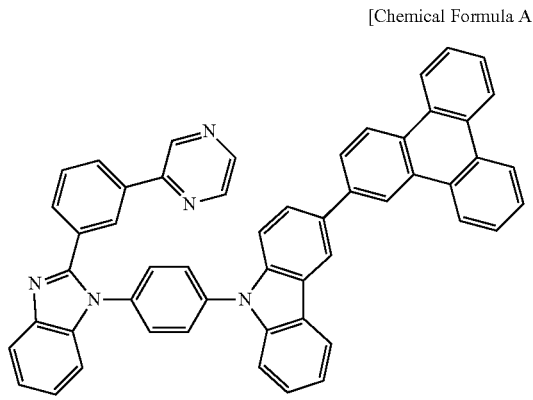
[Chemical Formula A18]
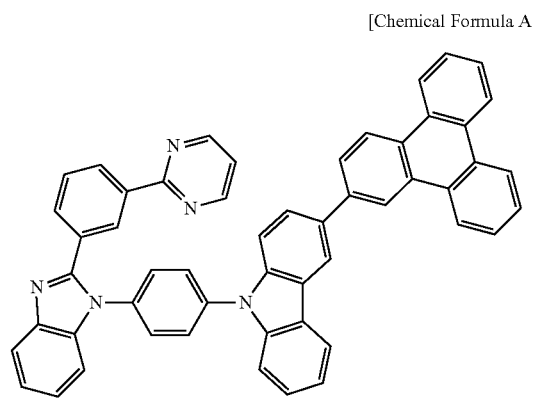
[Chemical Formula A19]
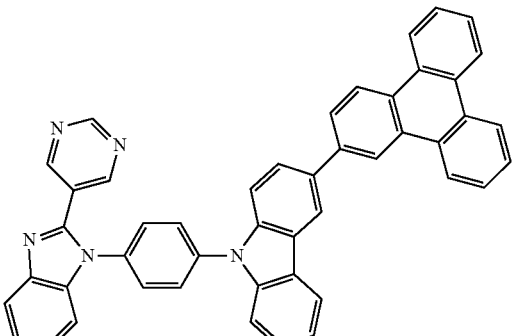
[Chemical Formula A20]
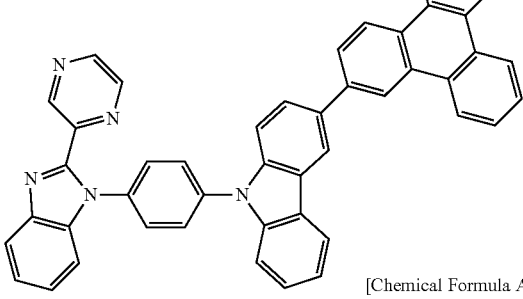
[Chemical Formula A21]
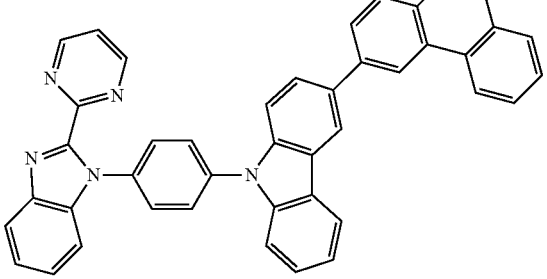
According to an example embodiment, a compound for an organic optoelectronic device may be represented by, e.g., the following Chemical Formulae B1 to B42.
[Chemical Formula B1]
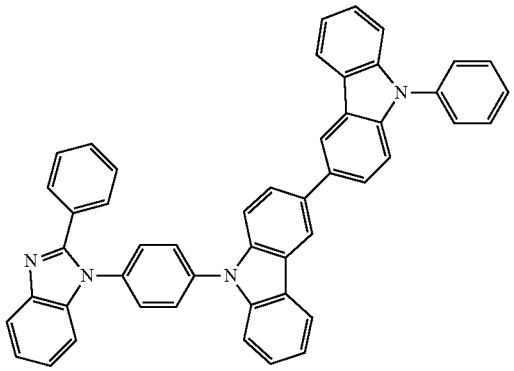

[Chemical Formula B2]
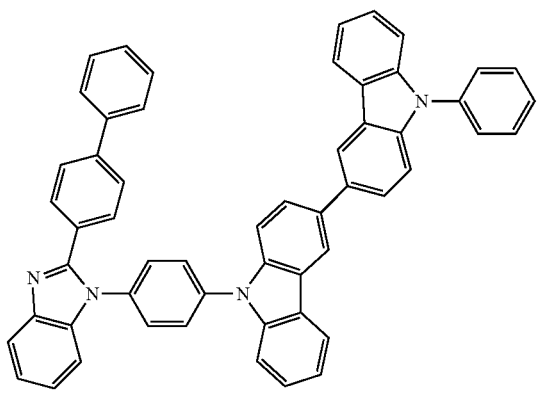
[Chemical Formula B3]
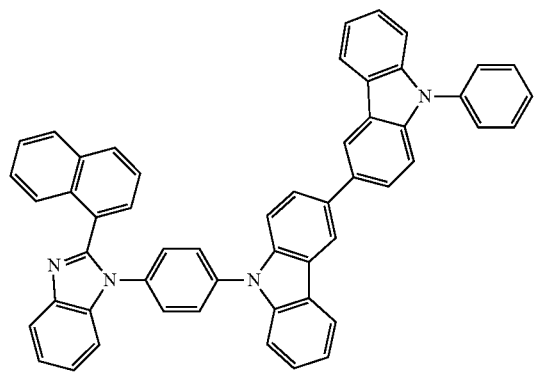
[Chemical Formul B4]
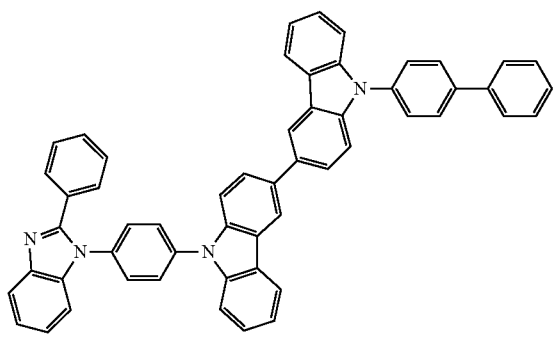
[Chemical Formula B5]
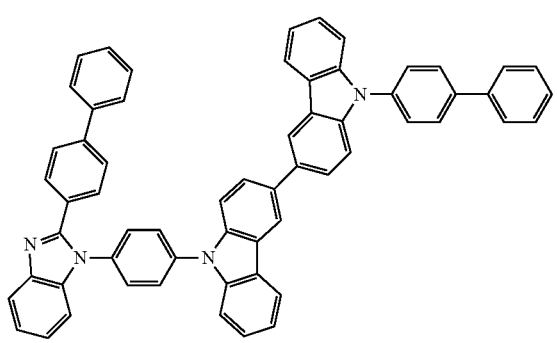
[Chemical Formula B6]
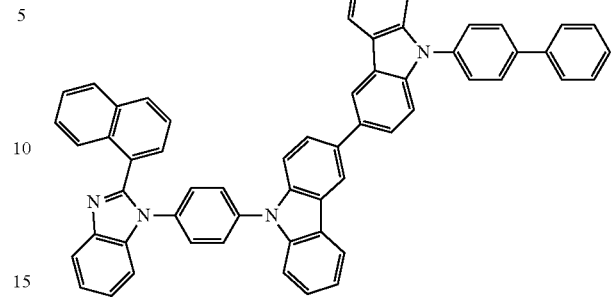
[Chemical Formula B7]
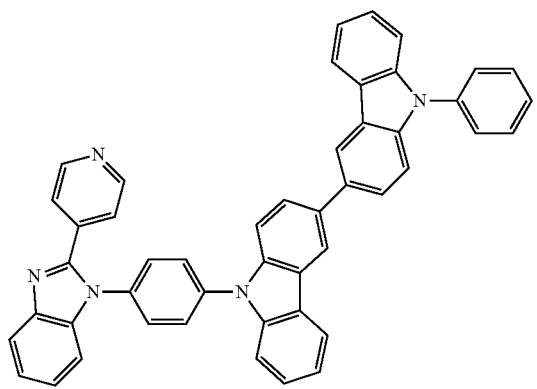
[Chemical Formula B8]
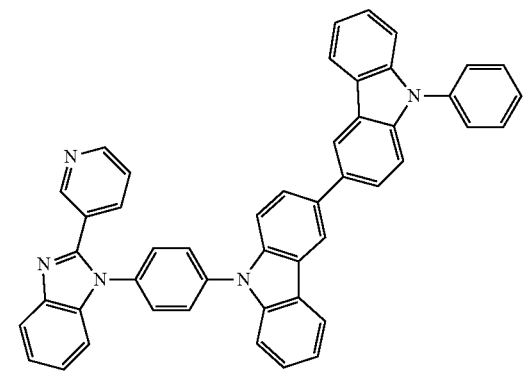
[Chemical Formula B9]
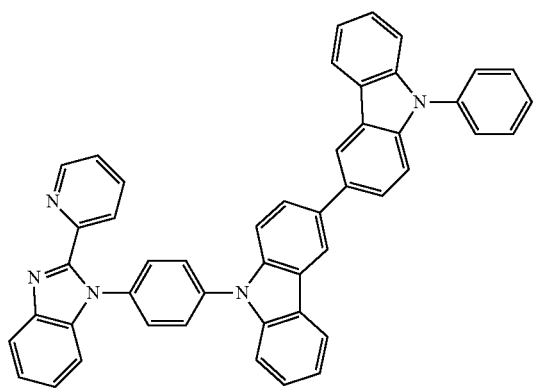

[Chemical Formula B10]
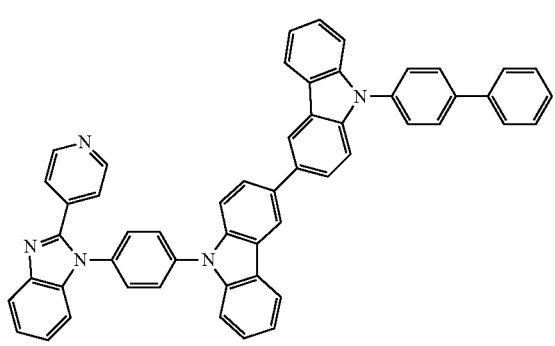
[Chemical Formula B11]
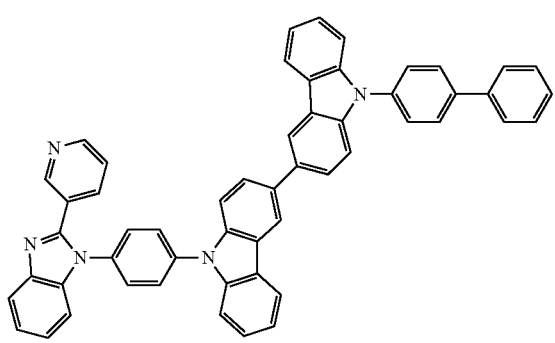
[Chemical Formula B12]
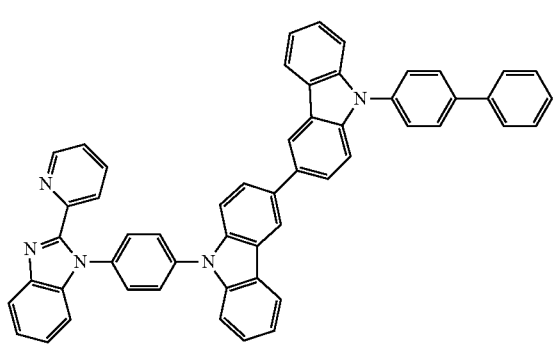
[Chemical Formula B13]
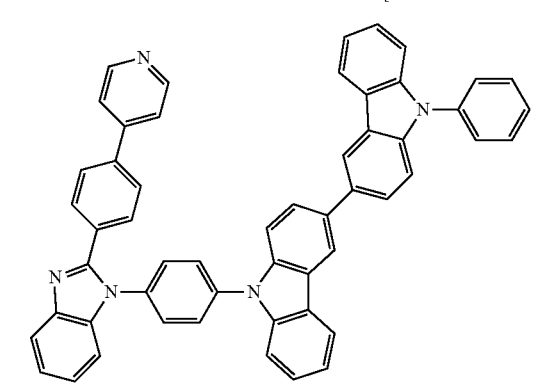
[Chemical Formula B14]
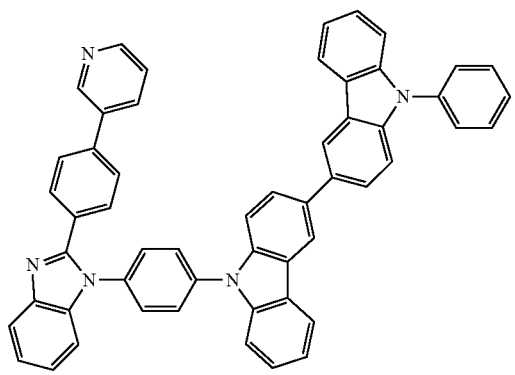
[Chemial Formula B15]
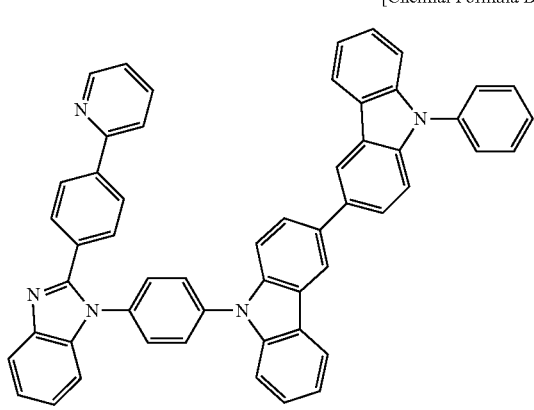
[Chemical Formula B16]
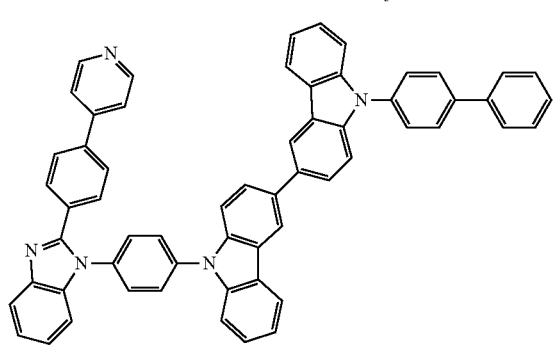
[Chemical Formula B17]
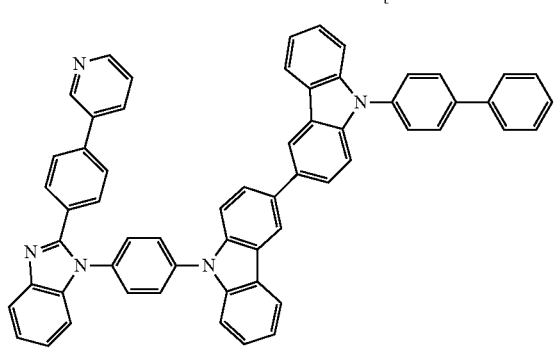

-continued
[Chemical Formula B18]
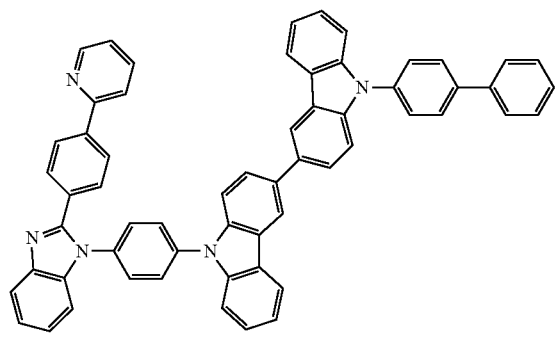
[Chemical Formula B19]
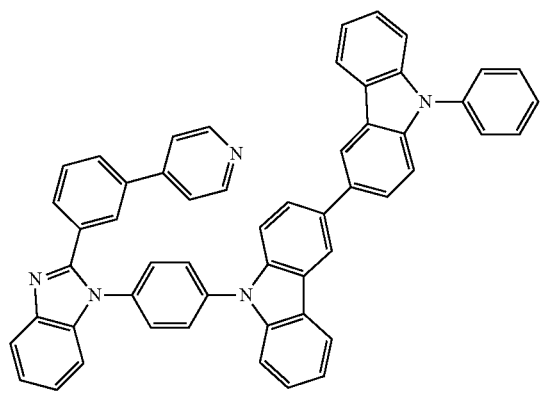
[Chemical Formula B20]
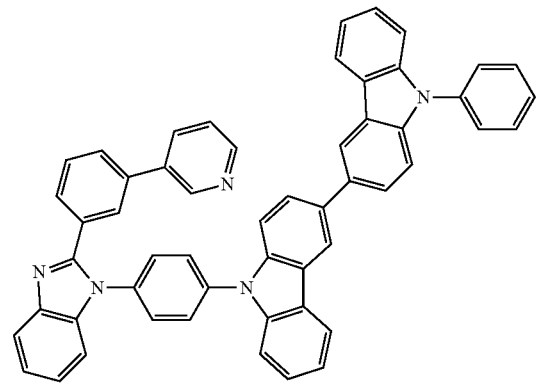
[Chemical Formula B21]
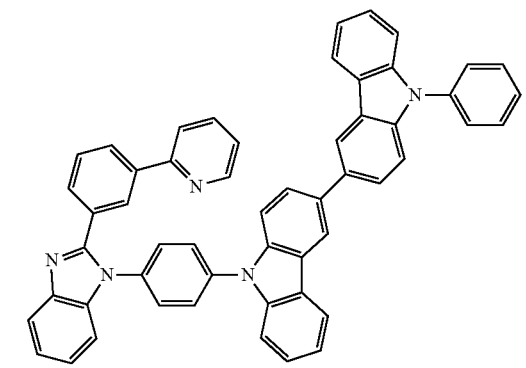
-continued
[Chemical Formula B22]
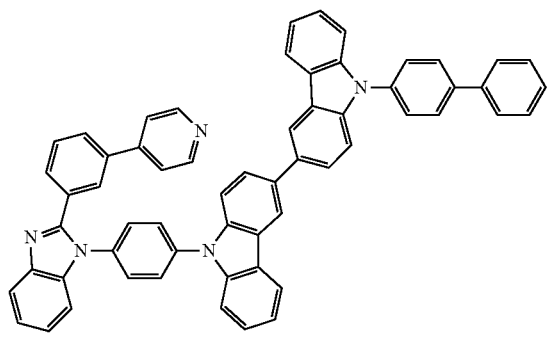
[Chemical Formula B23]
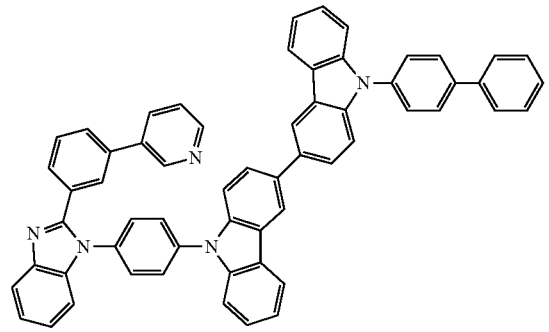
[Chemical Formula B24]
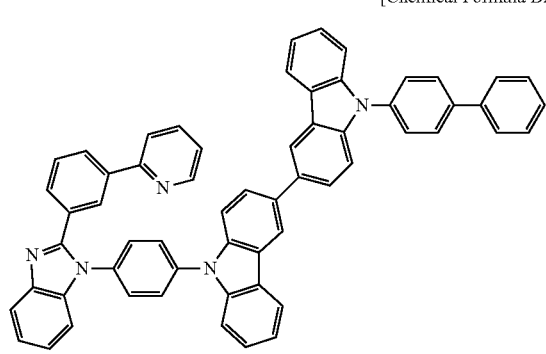
[Chemical Formula B25]
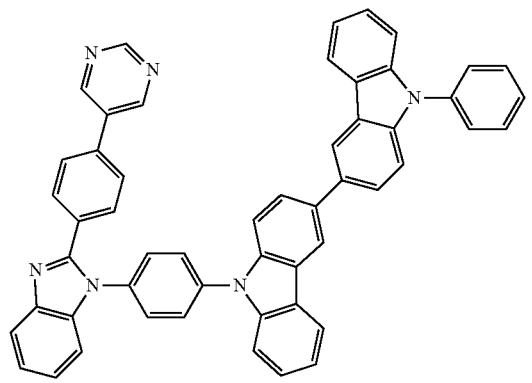

[Chemical Formula B26]
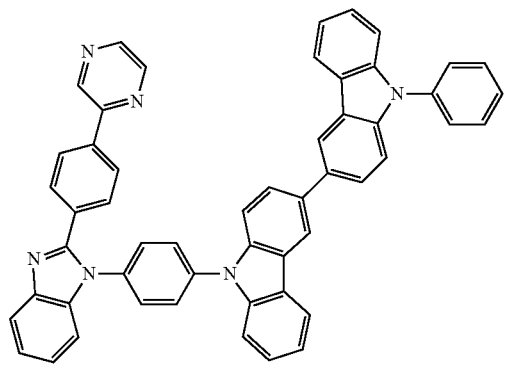
[Chemical Formula B27]
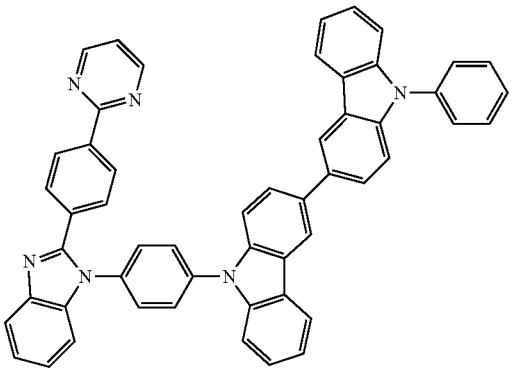
[Chemical Formula B28]
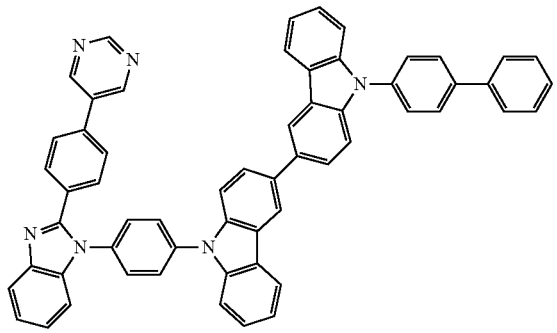
[Chemical Formula B29]
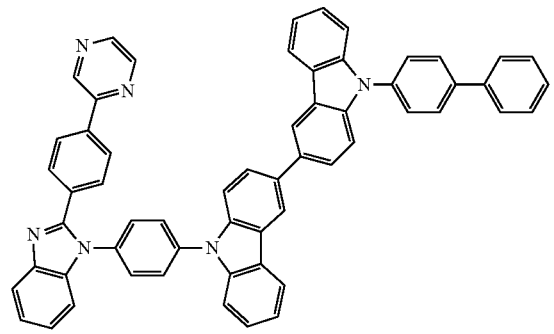
[Chemical Formula B30]
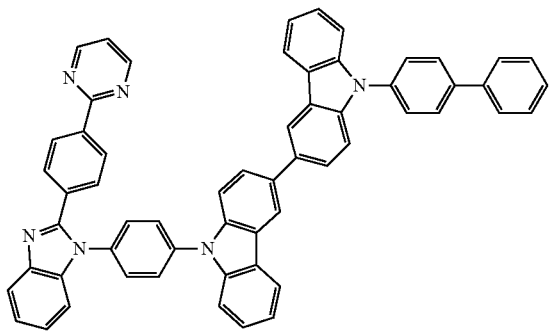
[Chemical Formula B31]
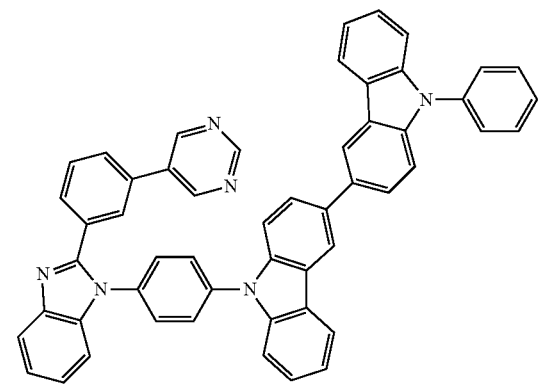
[Chemical Formula B32]
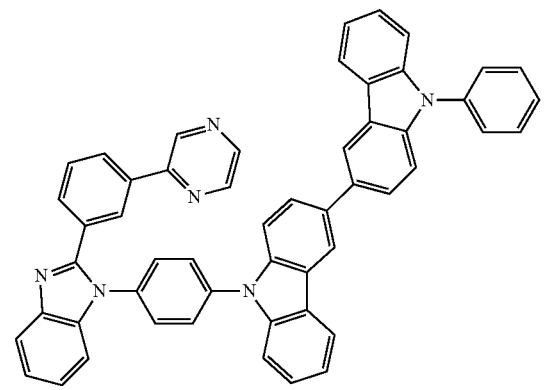
[Chemical Formula B33]
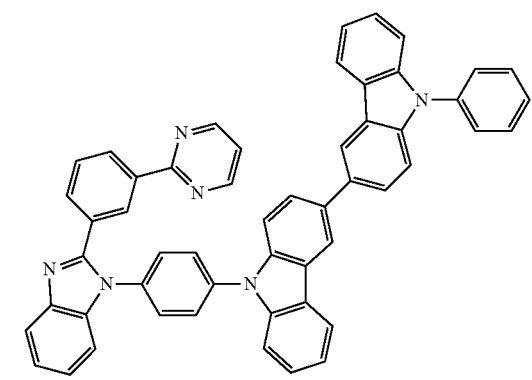

[Chemical Formula B34]
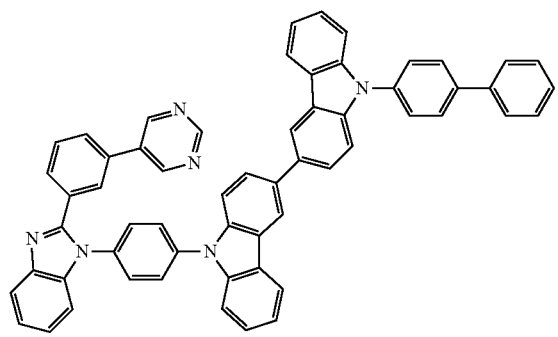
[Chemical Formula B35]
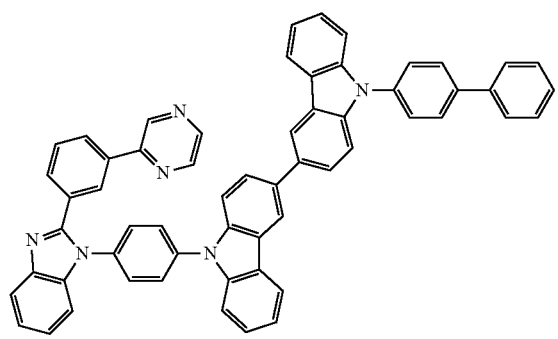
[Chemical Formula B36]
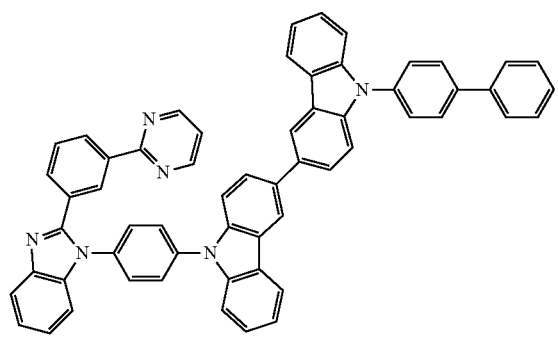
[Chemial Formula B37]
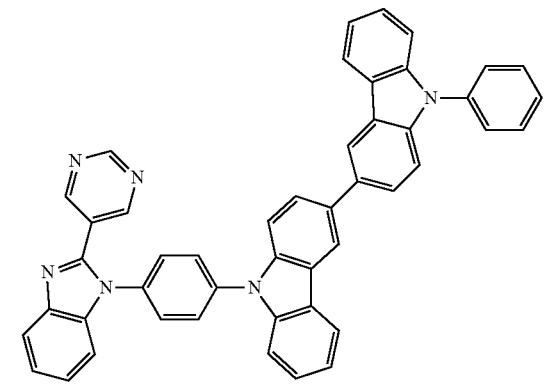
[Chemical Formula B38]
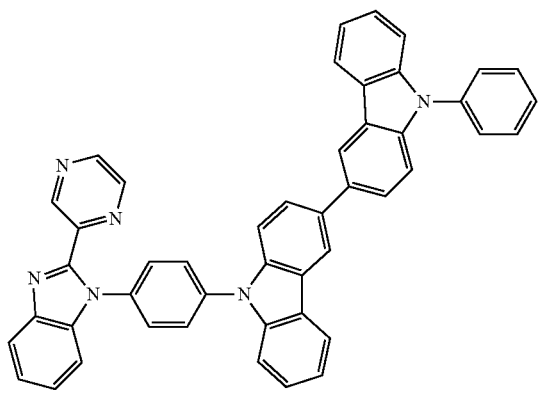
[Chemical Formula B39]
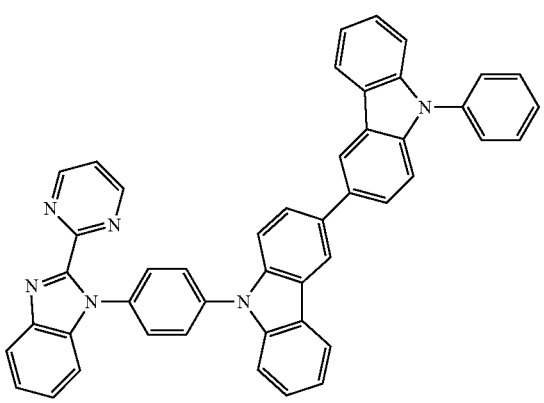
[Chemical Formula B40]
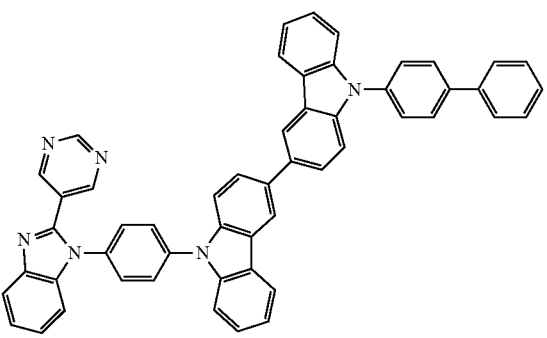
[Chemical Formula B41]
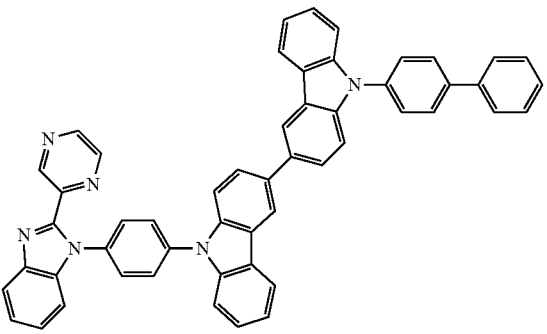

[Chemical Formula B42]
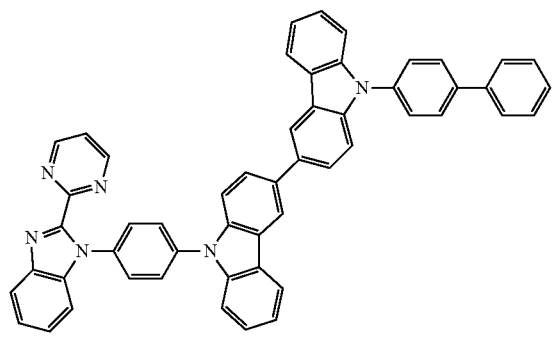
According to an example embodiment, the compound for an organic optoelectronic device may be represented by, e.g., the following Chemical Formulae C1 to C42.
[Chemical Formula C1]
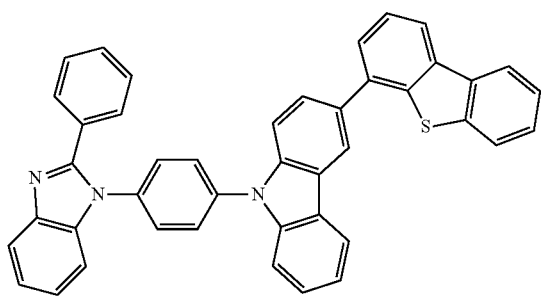
[Chemical Formula C2]
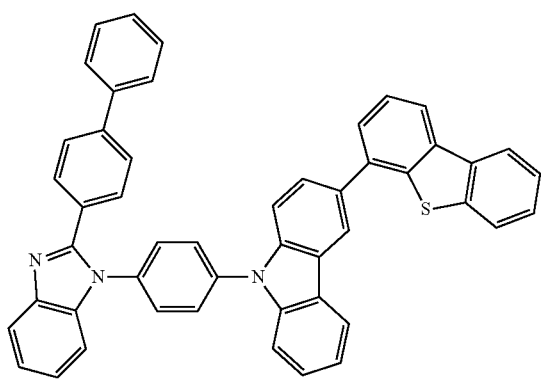
[Chemical Formula C3]
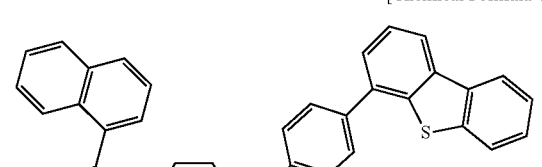
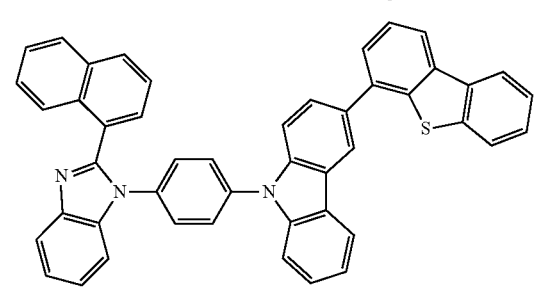
[Chemical Formula C4]
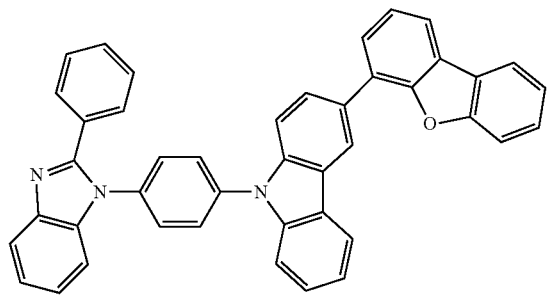
[Chemical Formula C5]
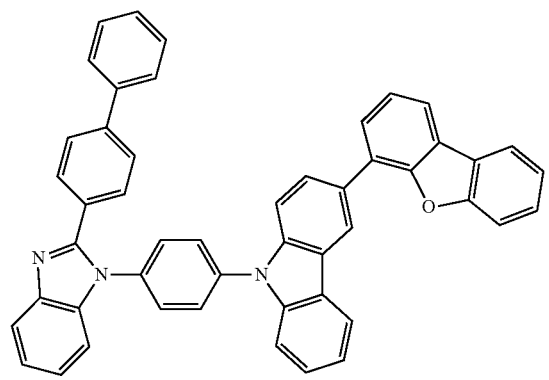
[Chemical Formula C6]
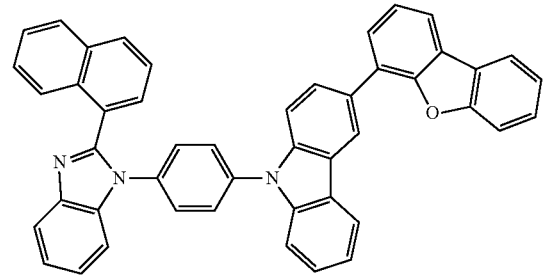
[Chemical Formula C7]
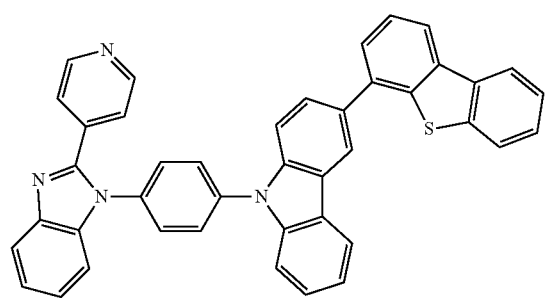
[Chemical Formula C8]
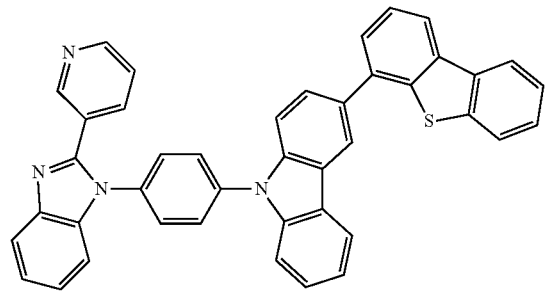

[Chemical Formula C9]
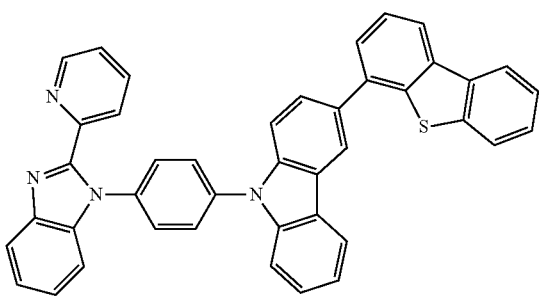
[Chemical Formula C10]
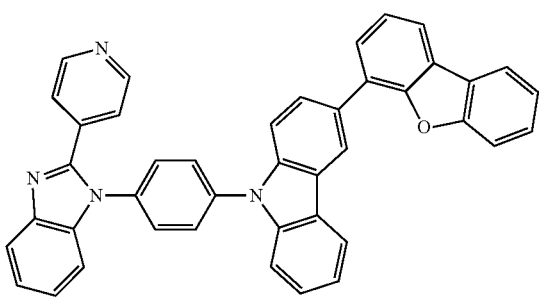
[Chemical Formula C11]
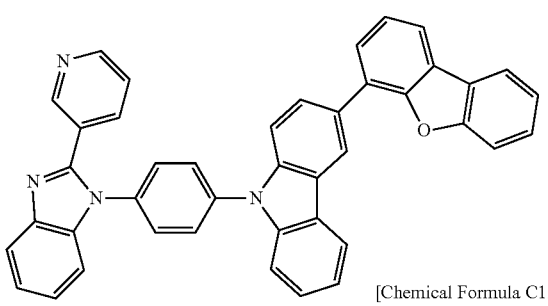
[Chemical Formula C12]
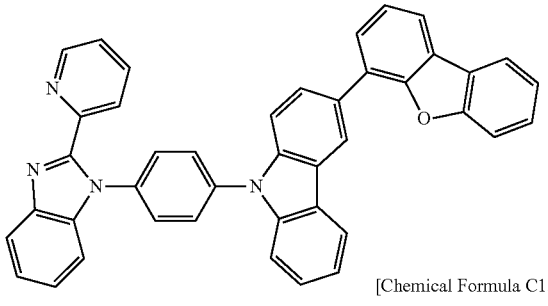
[Chemical Formula C13]
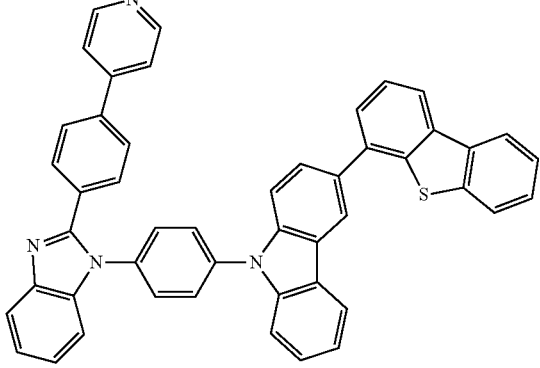
[Chemical Formula C14]
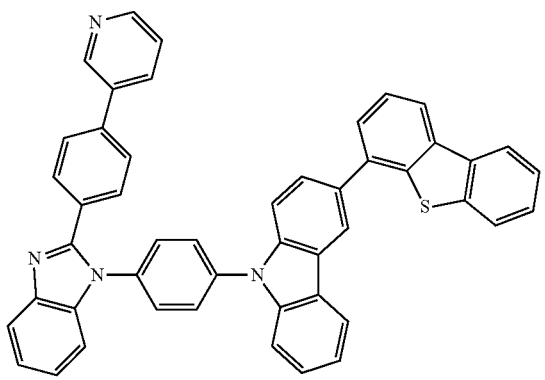
[Chemical Formula C15]
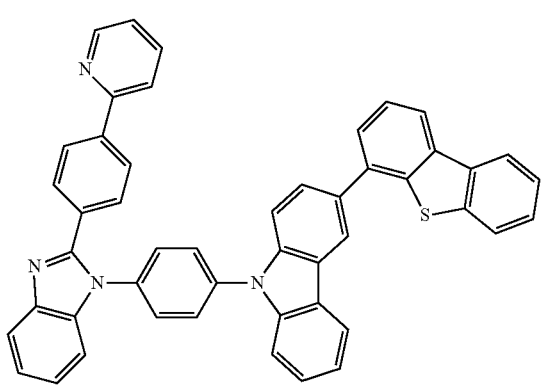
[Chemical Formula C16]
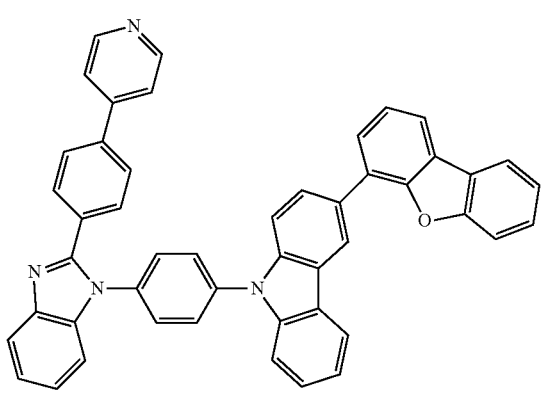
[Chemical Formula C17]
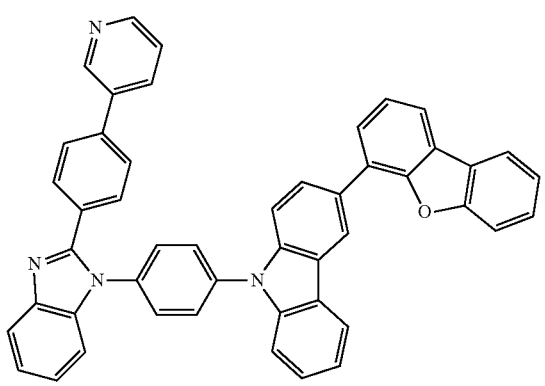

[Chemical Formula C18]
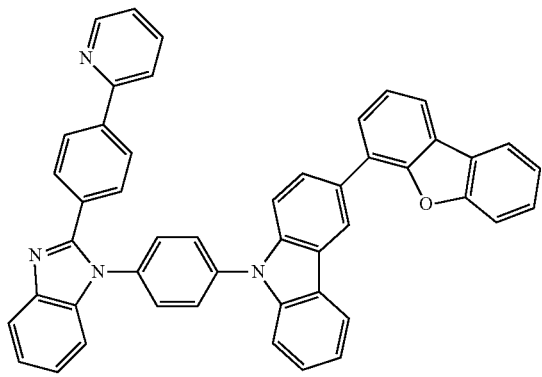
[Chemical Formula C19]
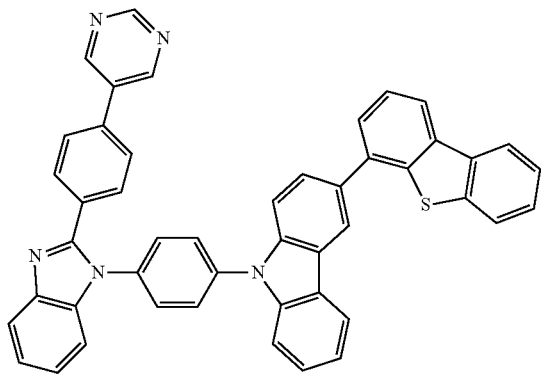
[Chemical Formula C20]
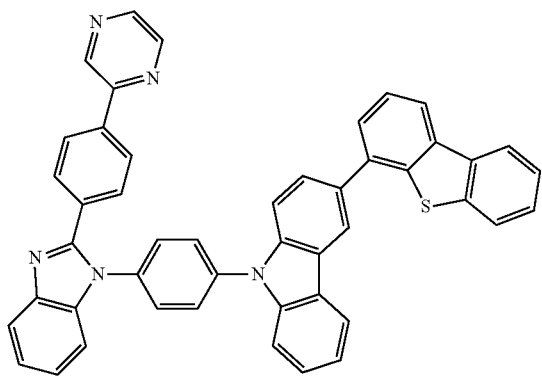
[Chemical Formula C21]
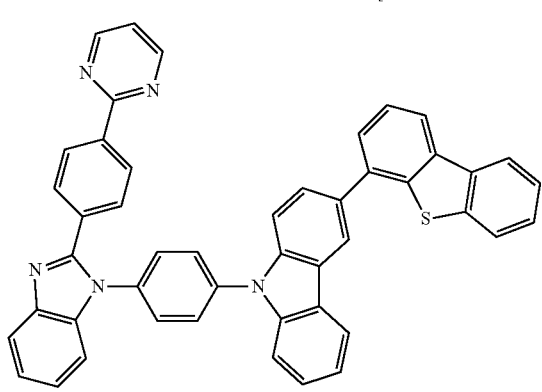
[Chemical Formula C22]
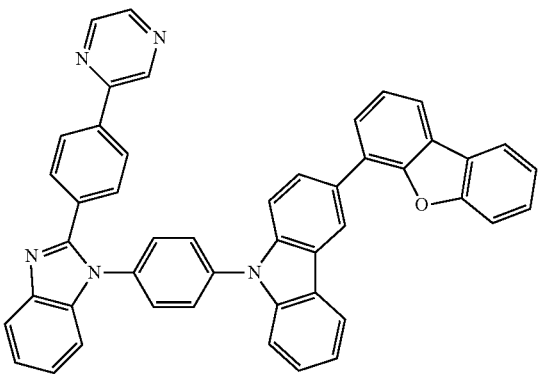
[Chemical Formula C23]
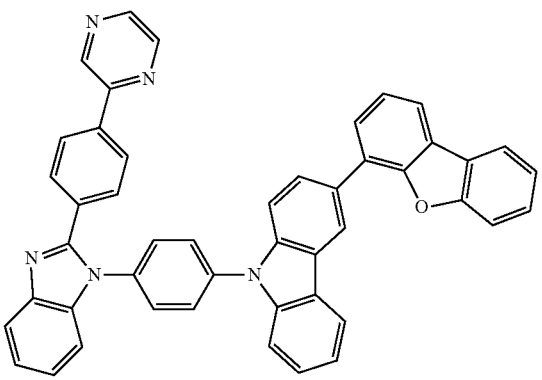
[Chemical Formula C24]
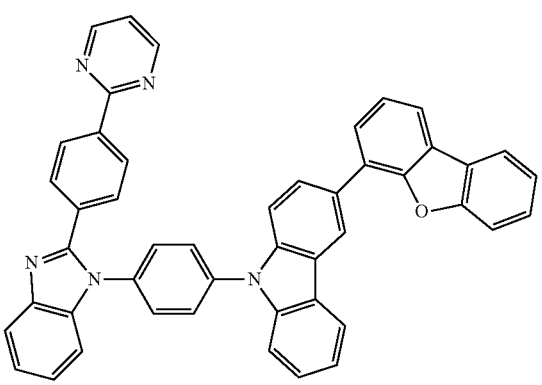
[Chemical Formula C25]
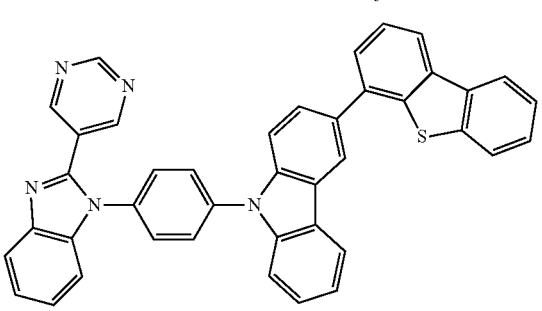

[Chemical Formula C26]
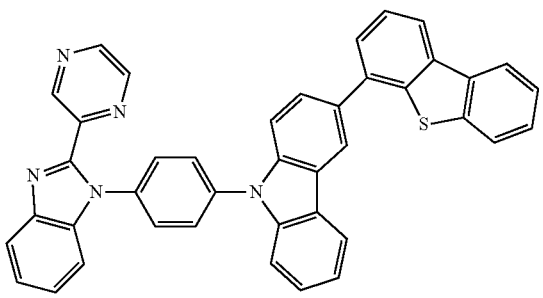
[Chemical Formula C27]
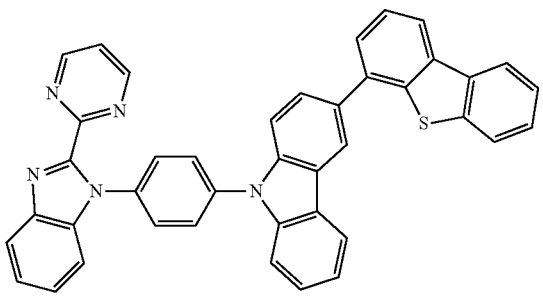
[Chemical Formula C28]
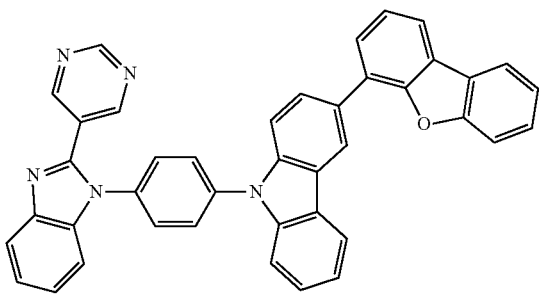
[Chemical Formula C29]
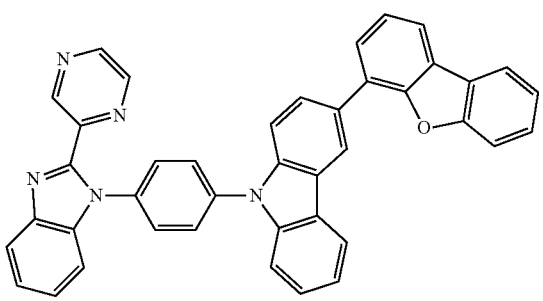
[Chemical Formula C30]
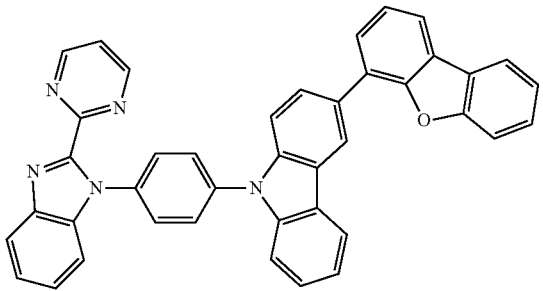
[Chemical Formula C31]
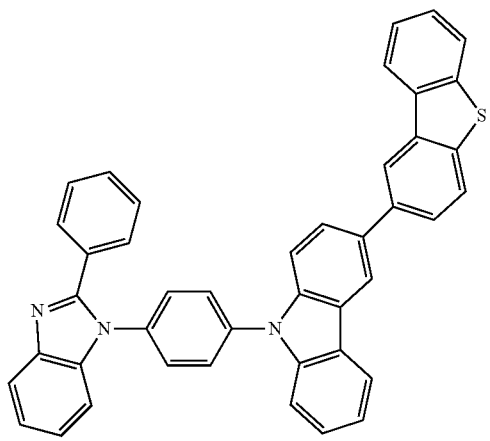
[Chemical Formula C32]
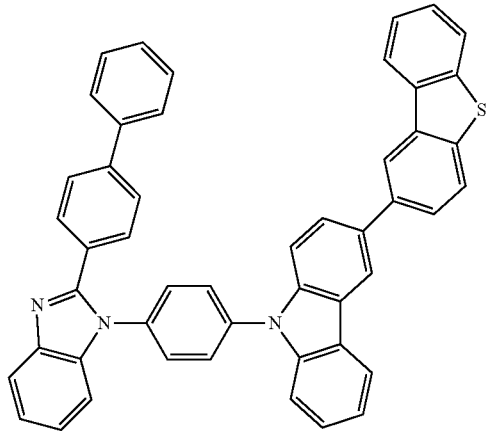
[Chemical Formula C33]
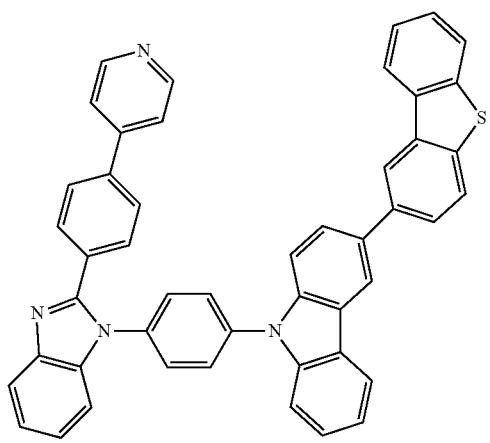

[Chemical Formula C34]
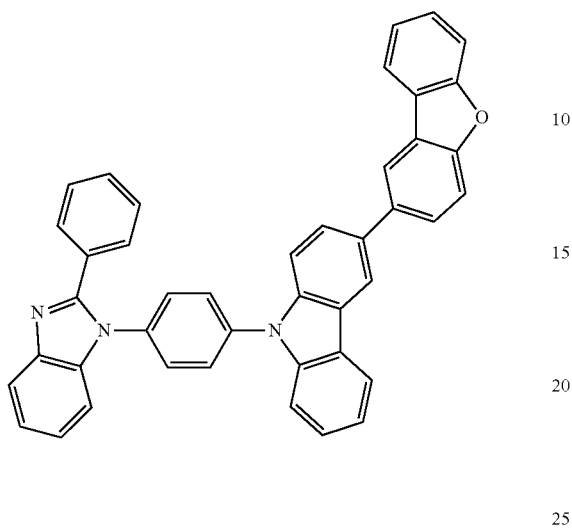
[Chemical Formula C35]
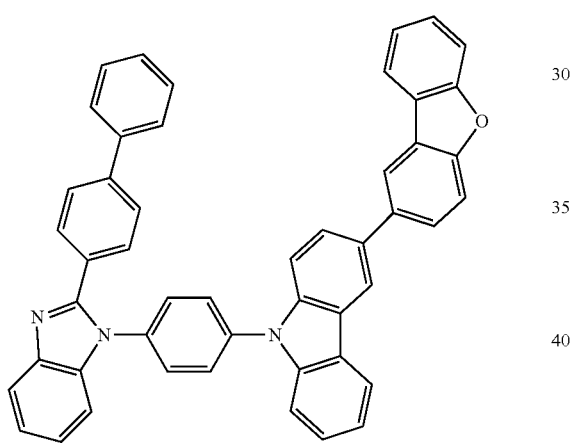
[Chemical Formula C36]
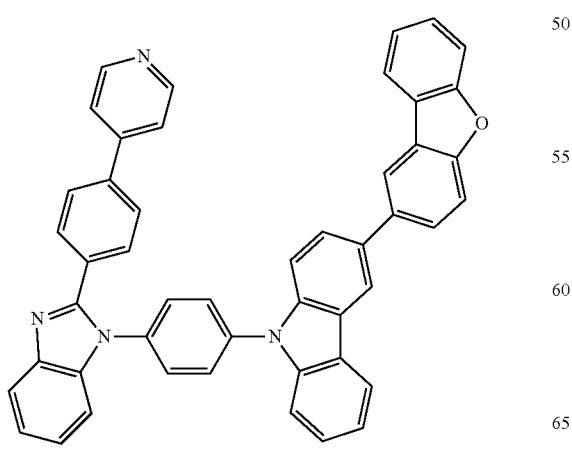
[Chemical Formula C37]
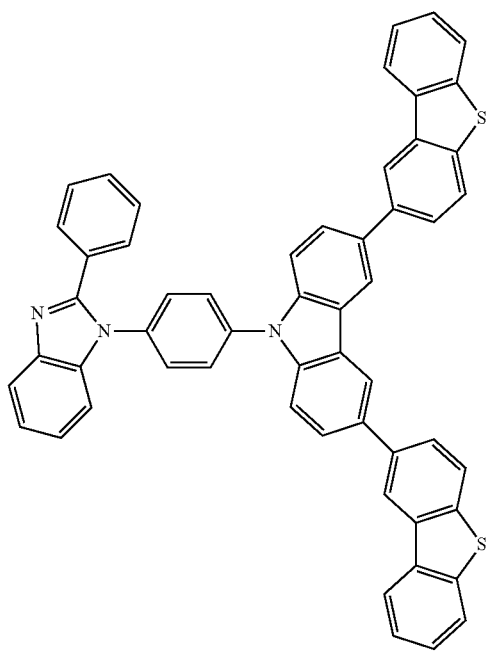
[Chemical Formula C38]
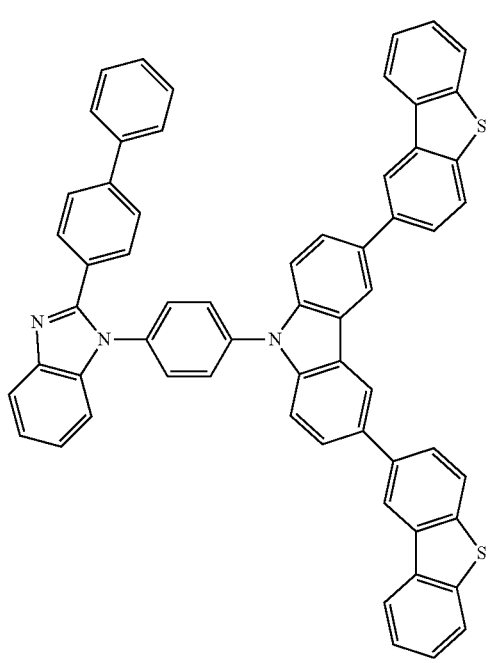

[Chemical Formula C39]

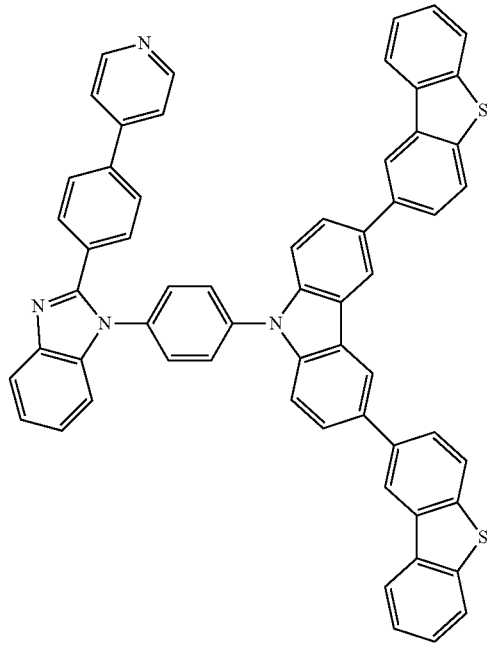

[Chemical Formula C40]

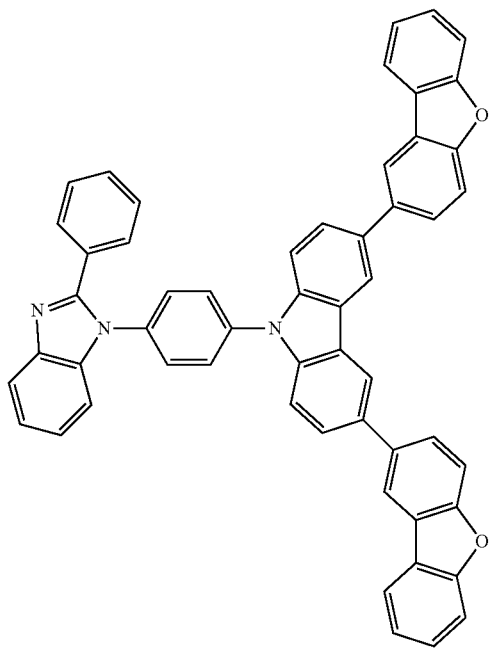

[Chemical Formula C41]

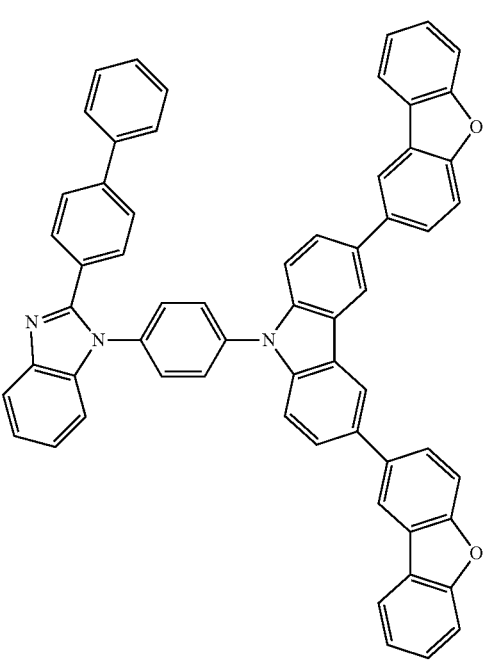

[Chemical Formula C42]

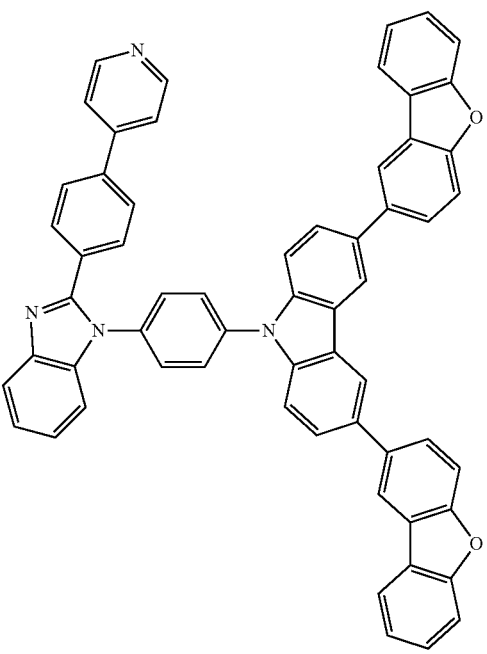

According to an example embodiment, a functional group having the electron characteristics may be introduced to improve life-span of an organic light emitting diode and decrease its driving voltage, and the compound may provide both electron and hole characteristics.

The compound according to the above-described example embodiment may have a maximum light emitting wavelength ranging from about 320 to 500 nm and triplet exciton energy (T1) of greater than or equal to 2.0 eV, e.g., from 2.0 to 4.0 eV.

A host material having high triplet exciton energy may well transport a charge to a dopant and increase luminous efficiency. Thus, the compound according to an example embodiment may be applied as a host material or a charge transport material, and may provide a decrease in driving voltage by adjusting HOMO and LUMO energy levels.

The compound for an organic optoelectronic device including the above compounds may have a glass transition temperature of greater than or equal to 110° C. and a thermal decomposition temperature of greater than or equal to 400° C., which may provide improved thermal stability, and an organic optoelectronic device having a high efficiency may be provided.

The compound for an organic optoelectronic device including the above compounds may play a role for emitting light or injecting and/or transporting electrons, and also act as a light emitting host with an appropriate dopant. The compound for an organic optoelectronic device may be used as, e.g., a phosphorescent or fluorescent host material, a blue light emitting dopant material, or an electron transport material.

The compound for an organic optoelectronic device according to an example embodiment may be used for an organic thin layer, and it may improve the life-span characteristics, efficiency characteristics, electrochemical stability, and thermal stability of an organic optoelectronic device and decrease the driving voltage.

According to another example embodiment, an organic optoelectronic device that includes the compound for an organic optoelectronic device is provided. The organic optoelectronic device may include an organic photoelectric device, an organic light emitting diode, an organic solar cell, an organic transistor, an organic photo-conductor drum, an organic memory device, or the like. For example, the compound for an organic optoelectronic device according to an example embodiment may be included in an electrode or an electrode buffer layer in the organic solar cell, which may improve the quantum efficiency, and it may be used as an electrode material for a gate, a source-drain electrode, or the like in the organic transistor.

According to another example embodiment, an anode, a cathode, and one or more organic thin layers between the anode and the cathode may be provided, and at least one of the organic thin layers may include the compound for an organic optoelectronic device according to an example embodiment.

The organic thin layer including the compound for an organic optoelectronic device may include a layer selected from an emission layer, a hole transport layer, a hole injection layer, an electron transport layer, an electron injection layer, a hole blocking layer, or a combination thereof. At least one of the organic thin layers may include the compound for an organic optoelectronic device according to an example embodiment. For example, the compound for an organic optoelectronic device according to an example embodiment may be included in an electron transport layer or electron injection layer. The compound for an organic optoelectronic device may be included in the emission layer, and the compound for an organic optoelectronic device may be included as a phosphorescent or fluorescent host, or as a fluorescent blue dopant material.

FIGS. 1 to 5 illustrate cross-sectional views showing organic light emitting diodes according to example embodiments including a compound for an organic optoelectronic device according to an embodiment.

Referring to FIGS. 1 to 5, organic light emitting diodes 100, 200, 300, 400, and 500 according to example embodiments include at least one organic thin layer 105 interposed between an anode 120 and a cathode 110.

According to the present example embodiment, the anode 120 includes an anode material having a large work function to help hole injection into an organic thin layer. The anode material includes: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combination of metal and oxide such as $ZnO:Al$ or $SnO_2:Sb$; or a conductive polymer such as poly(3-methylthiophene), poly[3,4-(ethylene-1,2-dioxy)thiophene] (PEDT), polypyrrole, and polyaniline, etc. For example, a transparent electrode including indium tin oxide (ITO) may be included as an anode.

The cathode 110 includes a cathode material having a small work function to help electron injection into an organic thin layer. The cathode material includes: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2/Al$, LiF/Ca, LiF/Al, and $BaF_2/Ca$, etc. A metal electrode including aluminum may be included as a cathode.

In the example embodiment shown in FIG. 1, the organic light emitting diode 100 includes an organic thin layer 105 including only an emission layer 130.

Figure 2:
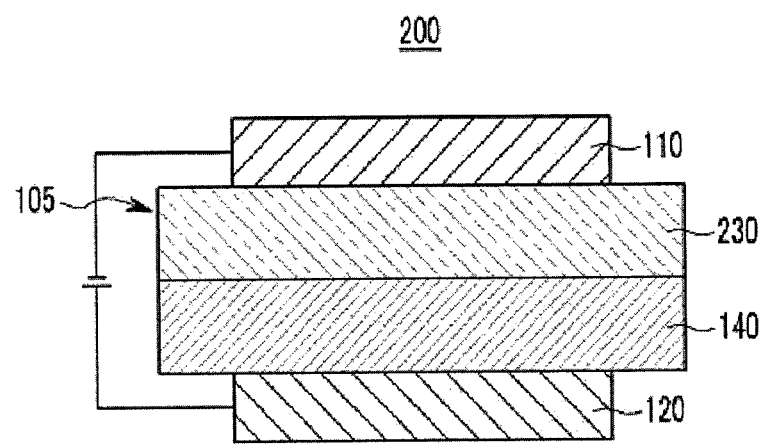

In the example embodiment shown in FIG. 2, a double-layered organic light emitting diode 200 includes an organic thin layer 105 including an emission layer 230 including an electron transport layer, and a hole transport layer 140. As shown in FIG. 2, the organic thin layer 105 includes a double layer of the emission layer 230 and hole transport layer 140. The emission layer 130 also functions as an electron transport layer, and the hole transport layer 140 layer may have an excellent binding property with a transparent electrode such as ITO or an excellent hole transport capability.

Figure 3:
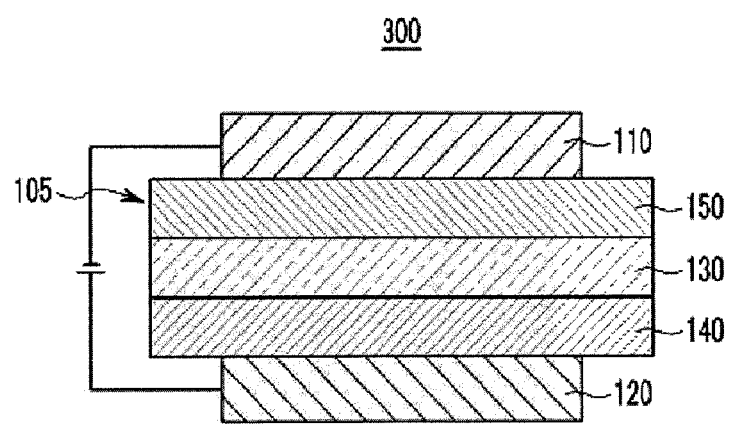

In the example embodiment shown in FIG. 3, a three-layered organic light emitting diode 300 includes an organic thin layer 105 including an electron transport layer 150, an emission layer 130, and a hole transport layer 140. The emission layer 130 is independently installed, and layers having an excellent electron transport capability or an excellent hole transport capability may be separately stacked.

Figure 4:
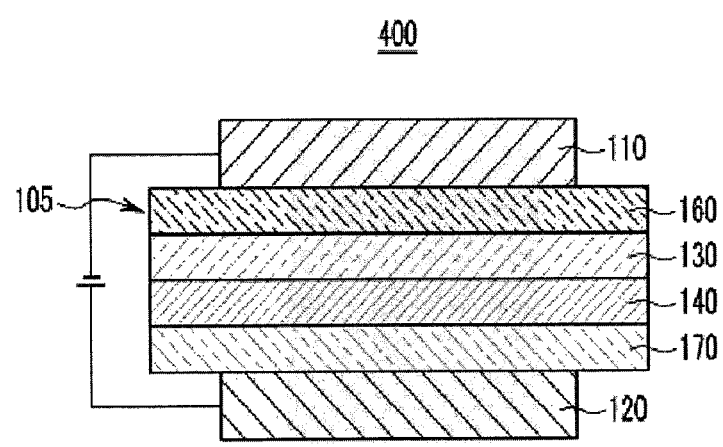

In the example embodiment shown in FIG. 4, a four-layered organic light emitting diode 400 includes an organic thin layer 105 including an electron injection layer 160, an emission layer 130, a hole transport layer 140, and a hole injection layer 170, which may enhance adherence with the cathode of ITO.

Figure 5:
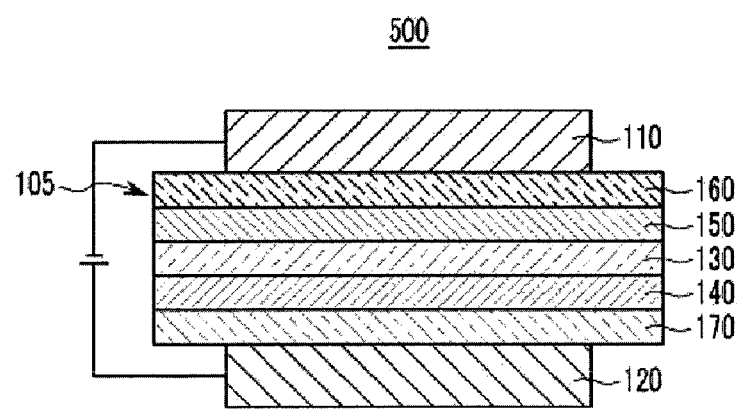

In the example embodiment shown in FIG. 5, a five-layered organic light emitting diode 500 includes an organic thin layer 105 including an electron transport layer 150, an emission layer 130, a hole transport layer 140, and a hole injection layer 170, and further includes an electron injection layer 160, which may help achieve a low voltage.

In FIGS. 1 to 5, the organic thin layer 105 including at least one selected from an electron transport layer 150, an electron injection layer 160, emission layers 130 and 230, a hole transport layer 140, a hole injection layer 170, or a combination thereof includes a compound for an organic optoelectronic device according to an embodiment. The compound for an organic optoelectronic device may be used for an electron transport layer 150 including the electron transport layer 150 or electron injection layer 160. When it is used for the electron transport layer, it may be possible to provide an organic optoelectronic device having a simpler structure by omitting an additional hole blocking layer (not shown).

Furthermore, when the compound for an organic optoelectronic device is included in the emission layers 130 and 230, the compound for the organic optoelectronic device may be included as a phosphorescent or fluorescent host or a fluorescent blue dopant.

The organic light emitting diode may be manufactured by: forming an anode on a substrate; forming an organic thin layer in accordance with a dry coating method such as evaporation, sputtering, plasma plating, and ion plating or a wet coating method such as spin coating, dipping, and flow coating; and providing a cathode thereon.

Another example embodiment provides a display device including the organic light emitting diode according to the above embodiment.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Preparation of Compound for Organic Optoelectronic Device

EXAMPLE 1

Synthesis of Compound Represented by Chemical Formula B2

A compound represented by Chemical Formula B2 as a specific example of a compound for an organic optoelectronic device according to an example embodiment was synthesized according to the following Reaction Scheme 1.

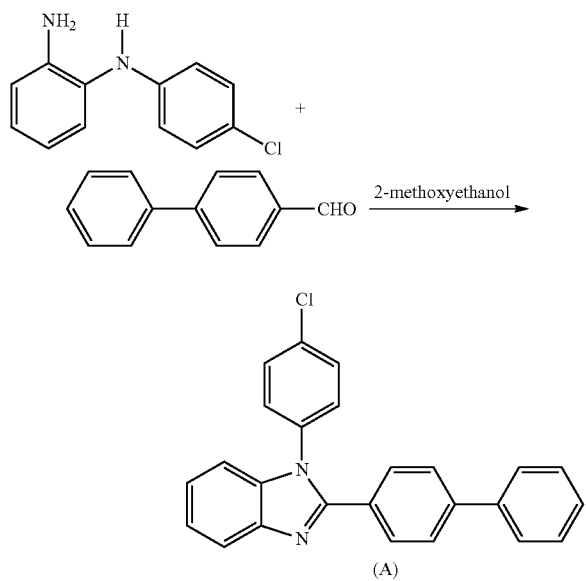

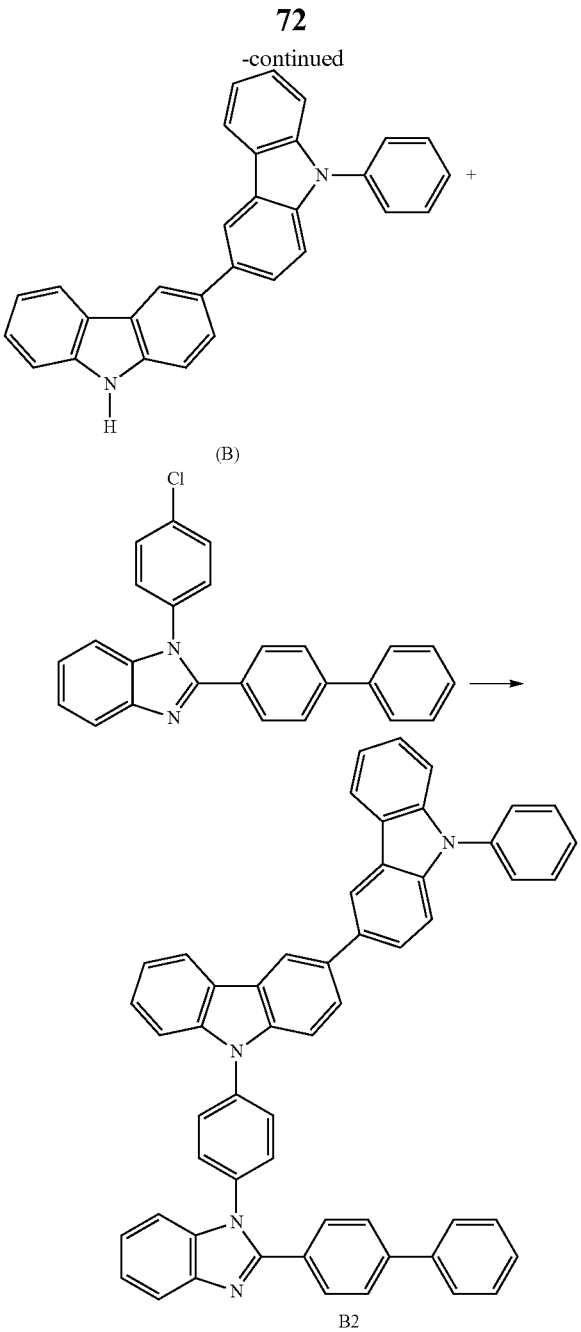

First Step: Synthesis of Compound A 41.6 g (160 mmol) of N-(4-chlorophenyl)-1,2-phenylene diamine and 33 g (180 mmol) of biphenyl-4-carboxaldehyde was agitated with 300 mL of 2-methoxy ethanol in a 2000 mL round flask, and the agitated mixture was agitated for 24 hours after increasing the temperature of the reaction vessel to a reflux temperature. The reaction solution was treated with methylene chloride to obtain an organic layer, and anhydrous magnesium sulfate was used to remove moisture from the organic layer. 30 g of a compound (A) (40% yield) was obtained by columnizing the reactant after removing the solvent therefrom.

The compound (A) was atomically analyzed, and the results are provided.

calcd. C25H17ClN2: C, 78.84; H, 4.50; N, 7.36. found: C, 78.80; H, 4.52; N, 7.40.

Second Step: Synthesis of Compound B2

16 g (40 mmol) of the compound (A), 15 g (40 mmol) of 9-phenyl-9H,9'H-[3,3']bicarbazol-yl (B), and 7.6 g (55 mmol) of potassium carbonate were suspended in 250 mL of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 mL of MeOH to obtain a crystallized solid, the crystallized solid was filtered and dissolved in monochlorobenzene, and the solution was filtered with silica gel/Celite. The appropriate amount of the organic solvent in the filtered solution was removed, and the remnant was recrystallized in MeOH, obtaining 15 g of a compound B2 (56% yield).

The compound B2 was atomically analyzed, and the results are provided as follows.

calcd. C55H36N4: C, 87.74; H, 4.82; N, 7.44. found: C, 87.76; H, 4.81; N, 7.39.

EXAMPLE 2

Synthesis of Compound Represented by Chemical Formula B3

A compound represented by Chemical Formula B3 as a specific example for an organic optoelectronic device according to an example embodiment was synthesized according to a method of the following Reaction Scheme 2.

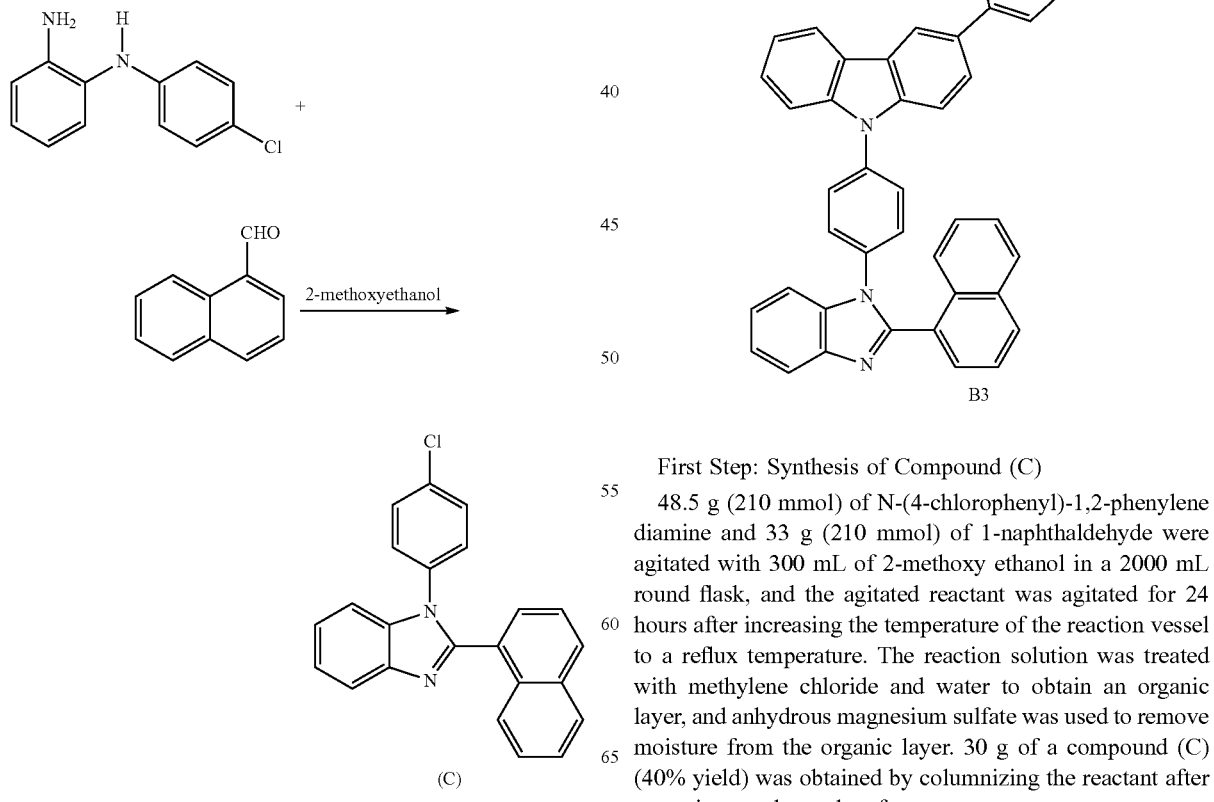

First Step: Synthesis of Compound (C)

48.5 g (210 mmol) of N-(4-chlorophenyl)-1,2-phenylene diamine and 33 g (210 mmol) of 1-naphthaldehyde were agitated with 300 mL of 2-methoxy ethanol in a 2000 mL round flask, and the agitated reactant was agitated for 24 hours after increasing the temperature of the reaction vessel to a reflux temperature. The reaction solution was treated with methylene chloride and water to obtain an organic layer, and anhydrous magnesium sulfate was used to remove moisture from the organic layer. 30 g of a compound (C) (40% yield) was obtained by columnizing the reactant after removing a solvent therefrom.

Atomic analysis of the obtained compound (C) was performed, and the results are provided as follows.

calcd. C23H25ClN2: C, 77.85; H, 4.26; N, 7.89. found: C, 77.79; H, 4.21; N, 7.79.

The obtained compound (C) was analyzed with a Nuclear Magnetic Resonance analyzer (NMR), and the results are provided as follows.

300 MHz (CDCl3, ppm): 8.05 (1H, t), 7.95 (1H, d), 7.82 (2H, m), 7.35 (7H, m), 7.18 (d, 2H), 7.05 (d, 2H)

Second Step: Synthesis of Compound B3

14.5 g (40 mmol) of the compound (C), 14.5 g (40 mmol) of 9-phenyl-9H,9'H-[3,3']bicarbazol-yl (B), and 7.5 g (53 mmol) of potassium carbonate were suspended in 250 mL of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 mL of MeOH to obtain a crystallized solid, then the crystallized solid was filtered and dissolved in monochlorobenzene, and the solution was filtered with silica gel/Celite. The appropriate amount of an organic solvent therein was removed, and the remnant was recrystallized in MeOH, obtaining 16.5 g of a compound B3 (65% yield).

Atomic analysis of the compound B3 was performed, and the results are provided as follows.

calcd. C53H34N4: C, 87.58; H, 4.71; N, 7.71. found: C, 87.60; H, 4.68; N, 7.65.

EXAMPLE 3

Synthesis of Compound Represented by Chemical Formula B16

The compound represented by Chemical Formula B16 as a specific example of a compound for an organic optoelectronic device according to an example embodiment was synthesized according to the following Reaction Scheme 3.

[Reaction Scheme 3]

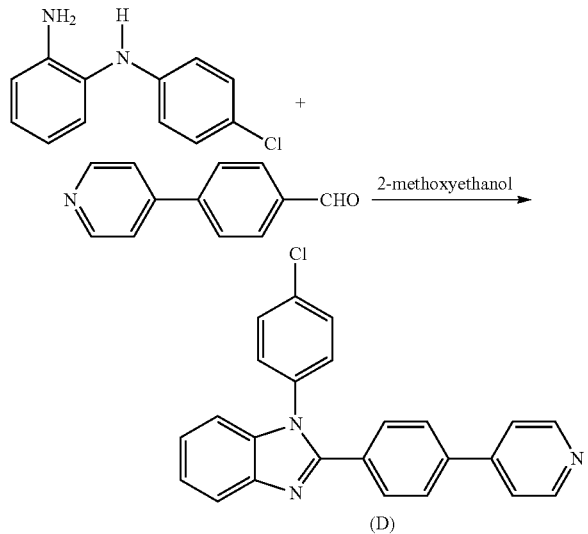

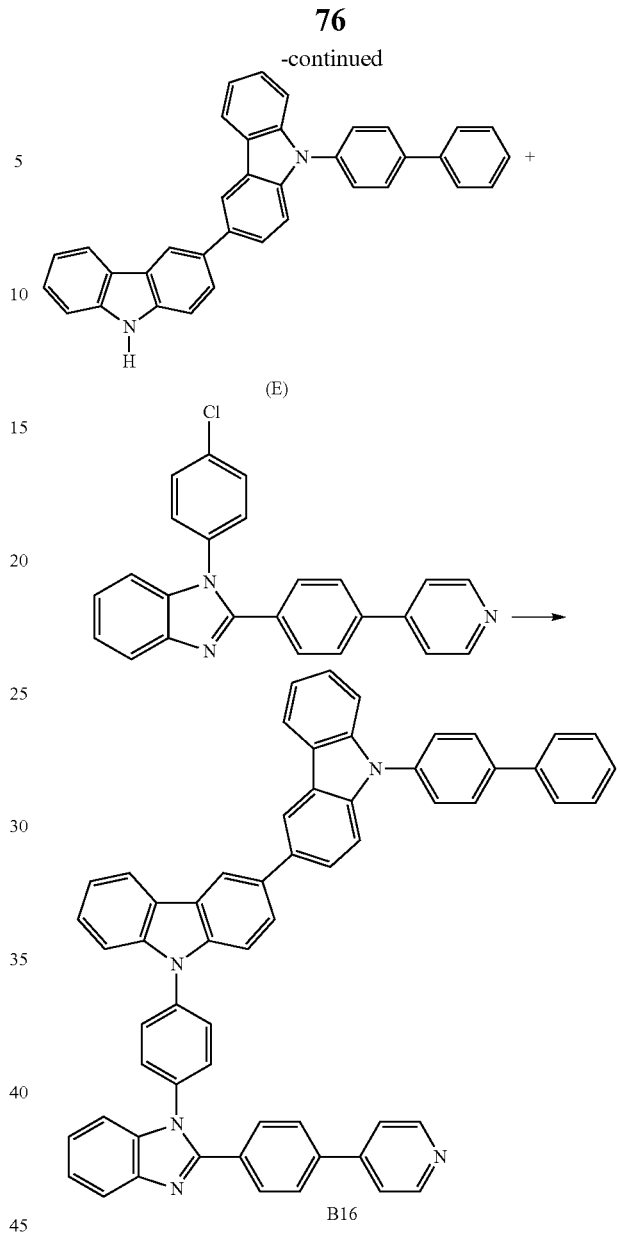

First Step: Synthesis of Compound (D)

25 g (110 mmol) of N-(4-chlorophenyl)-1,2-phenylene diamine and 20 g (110 mmol) of biphenyl-4-carboxaldehyde were agitated with 300 mL of 2-methoxy ethanol in a 2000 mL round flask, the temperature of the reaction vessel was increased up to a reflux temperature, and the resultant was agitated for 24 hours. The reaction solution was treated with methylene chloride and water to obtain an organic layer, and anhydrous magnesium sulfate was used to remove moisture from the organic layer. 12 g of a compound (D) (28% yield) was obtained by columnizing the resultant after removing a solvent therefrom.

Atomic analysis of the compound (D) was performed, and the results are provided as follows.

calcd. C24H16ClN3: C, 75.49; H, 4.22; N, 11. found: C, 75.79; H, 4.11; N, 11.8.

Second step: Synthesis of Compound B16

12 g (31 mmol) of the compound (D), 15 g (31 mmol) of 9-biphenyl-9H,9'H-[3,3']bicarbazol-yl (E), and 6.5 g (47 mmol) of potassium carbonate were suspended in 250 mL of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 mL of MeOH to crystallize a solid, the solid was dissolved in monochlorobenzene and then filtered with silica gel/Celite. 15.6 g of a compound B16 (60% yield) was obtained by conducting recrystallization with MeOH after removing the appropriate amount of an organic solvent.

Atomic analysis of the compound B16 was performed, and the results are provided as follows.

calcd. C60H39N5: C, 86.83; H, 4.74; N, 8.44. found: C, 87.01; H, 4.69; N, 8.49.

EXAMPLE 4

Synthesis of Compound Represented by Chemical Formula C32

A compound represented by Chemical Formula C32 as a specific example of a compound for an organic optoelectronic device according to an example embodiment was synthesized according to the following Reaction Scheme 4.

[Reaction Scheme 4]

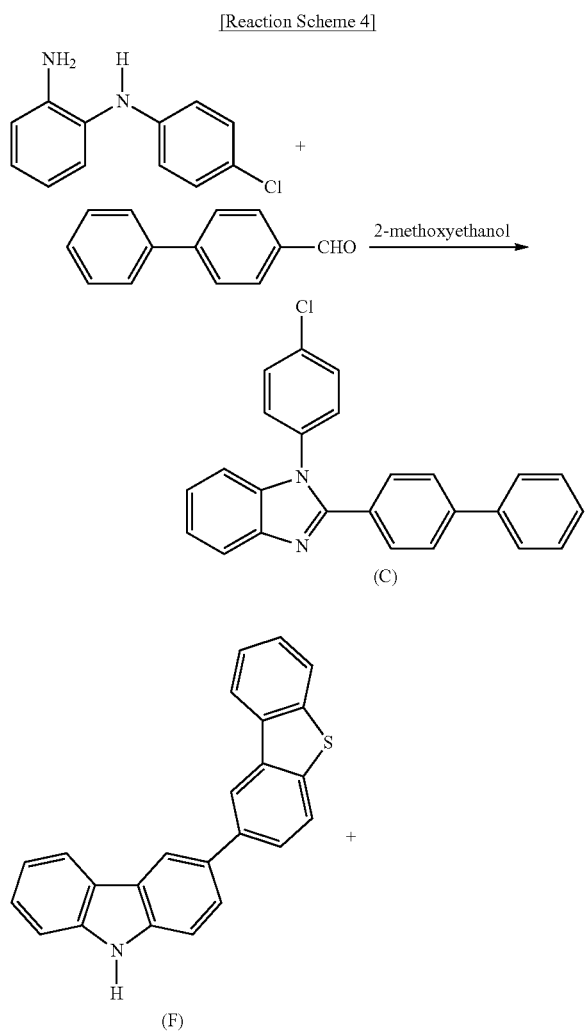

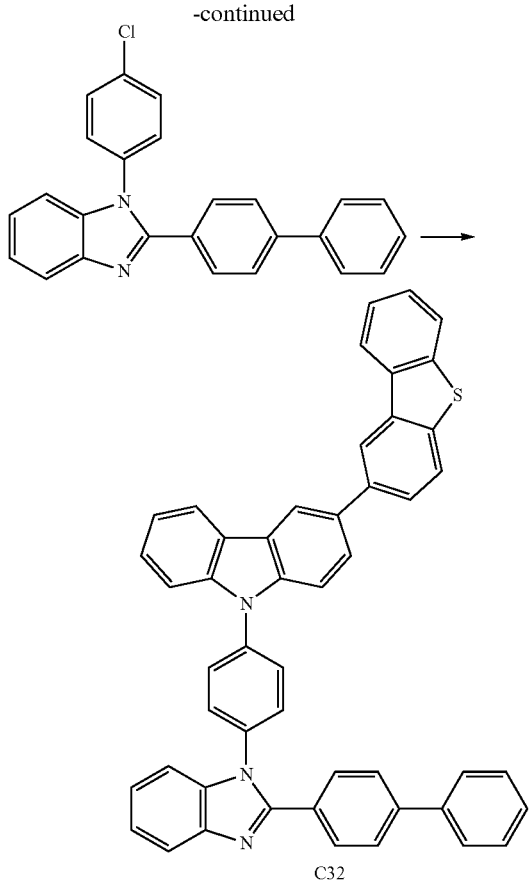

First Step: Synthesis of Compound (C)

While 41.6 g (160 mmol) of N-(4-chlorophenyl)-1,2-phenylene diamine and 33 g (180 mmol) of biphenyl-4-carboxaldehyde were agitated with 300 mL of 2-methoxy ethanol in a 2000 mL round flask, the temperature of the reaction vessel was increased to a reflux temperature, and the resultant was agitated for 24 hours. The reaction solution was treated with methylene chloride and water to obtain an organic layer, and anhydrous magnesium sulfate was used to remove moisture from the organic layer. 30 g of a compound (C) (40% yield) was obtained by columnizing the resultant after removing a solvent therefrom.

Atomic analysis of the compound (C) was performed, and the results are provided as follows.

calcd. C25H17ClN2: C, 78.84; H, 4.50; N, 7.36. found: C, 78.80; H, 4.52; N, 7.40.

Second Step: Synthesis of Compound C32

16 g (40 mmol) of the compound (C), 14 g (40 mmol) of 3-dibenzothiophen-2-yl-9-H-carbazole (F), and 7.6 g (55 mmol) of potassium carbonate were suspended in 250 mL of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 mL of MeOH to crystallize a solid, the solid was filtered and dissolved in monochlorobenzene, and the solution was filtered with silica gel/Celite. 15.5 g of a compound C32 (56% yield) was obtained by conducting recrystallization with MeOH after removing the appropriate amount of an organic solvent therein.

Atomic analysis of the obtained compound C32 was performed, and the results are provided as follows.

calcd. C49H31N3S: C, 84.82; H, 4.50; N, 6.06; S, 4.62.
found: C, 84.79; H, 4.54; N, 6.02.

EXAMPLE 5

Synthesis of Compound Represented by Chemical Formula C33

A compound represented by Chemical Formula C33 as a specific example of a compound for an organic optoelectronic device according to an example embodiment was synthesized according to the following Reaction Scheme 5.

[Reaction Scheme 5]

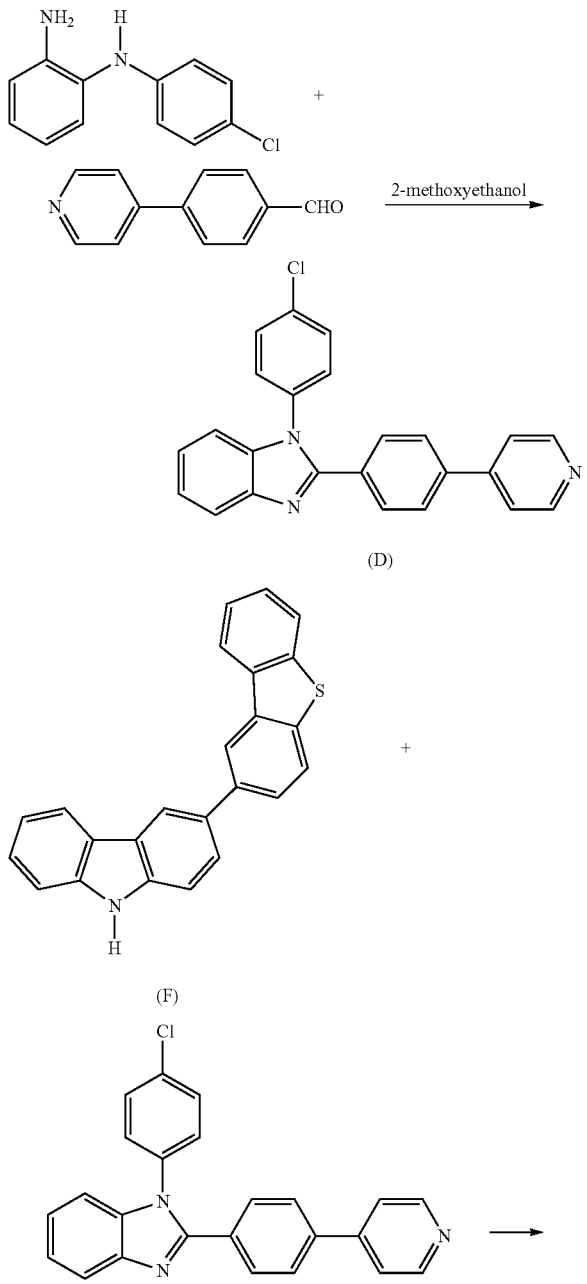

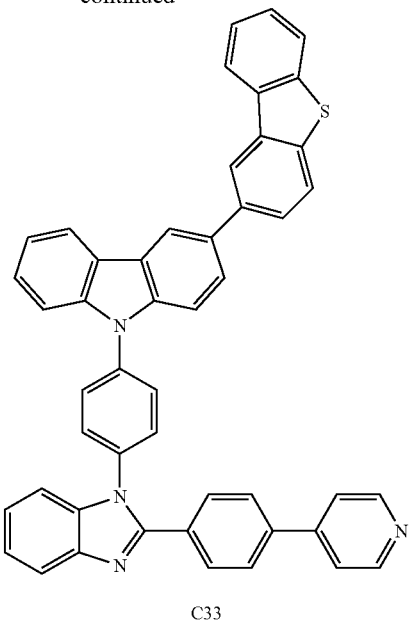

C33

First Step: Synthesis of Compound (D)

While 25 g (110 mmol) of N-(4-chlorophenyl)-1,2-phenylene diamine and 20 g (110 mmol) of biphenyl-4-carboxaldehyde were agitated with 300 mL of 2-methoxy ethanol in a 2000 mL round flask, the temperature of the reaction vessel was increased to a reflux temperature, and the resultant was agitated for 24 hours. The reaction solution was treated with methylene chloride and water to obtain an organic layer, and anhydrous magnesium sulfate was used to remove moisture from the organic layer. 12 g of a compound (D) (28% yield) was obtained by columnizing the resultant after removing a solvent therefrom.

Atomic analysis of the compound (D) was performed, and the results are provided as follows.

calcd. C24H16ClN3: C, 75.49; H, 4.22; N, 11. found: C, 75.79; H, 4.11; N, 11.8.

Second Step: Synthesis of Compound C33

12 g (31 mmol) of the compound (D), 15 g (31 mmol) of 3-dibenzothiophen-2-yl-9-H-carbazole (F), and 6.5 g (47 mmol) of potassium carbonate were suspended in 250 mL of DMSO, 1 g (7 mmol) of 1,10-phenanthroline and 1 g (7 mmol) of copper chloride were added thereto, and the mixture was heated and refluxed under a nitrogen stream for 12 hours. The reaction solution was added to 1000 mL of MeOH to crystallize a solid, the solid was filtered and dissolved in monochlorobenzene, and the solution was filtered with silica gel/Celite. 13 g of a compound C33 (60% yield) was obtained by conducting recrystallization in MeOH after removing the appropriate amount of an organic solvent therefrom.

Atomic analysis of the compound C33 was performed, and the results are provided as follows.

calcd. C48H30N4S: C, 82.97; H, 4.35; N, 8.06; S, 4.61. found: C, 83.01; H, 4.40; N, 8.01.

Manufacture of Organic Light Emitting Diode

EXAMPLE 6

As an example, a method of manufacturing the organic light emitting diode is illustrated as follows: an anode was manufactured by cutting an ITO glass substrate having sheet resistance of 15 Ω/cm² into a size of 50 mm×50 mm×0.7 mm, cleaning the ITO glass substrate with an ultrasonic wave in acetone, isopropyl alcohol, and pure water respectively for 15 minutes, and then with a UV ozone for 30 minutes.

The ITO transparent electrode was used as an anode, and the following HTM compound was vacuum-deposited to form a 1200 Å-thick hole injection layer on the ITO substrate.

[HTM]

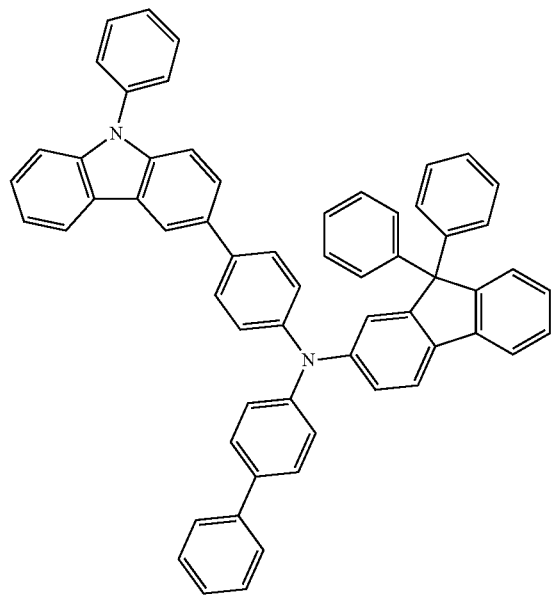

The compound according to Example 1 as a host was doped with 7 wt % of the following PhGD compound as a phosphorescent green dopant, and the doped compound was vacuum-deposited to form a 300 Å-thick emission layer. 1000 Å-thick ITO was used as an anode, and 1000 Å-thick aluminum (Al) was used as a cathode.

[PhGD]

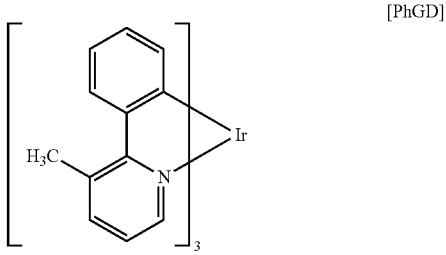

Subsequently, BAlq [bis(2-methyl-8-quinolinolato-N1,O8)-(1,1'-biphenyl-4-olato)aluminum] and Alq3 [tris(8-hydroxyquinolinato)aluminum] were sequentially deposited to be 50 Å thick and 250 Å thick on the emission layer upper to form an electron transport layer. On the electron transport layer upper, LiF and Al were sequentially vacuum-deposited to be 5 Å and 1000 Å thick to form a cathode, manufacturing an organic light emitting diode.

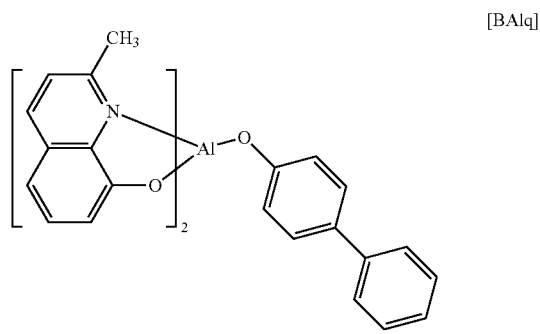

EXAMPLE 7

An organic light emitting diode was manufactured according to the same method as Example 6 except for using the compound according to Example 3 instead of the compound according to Example 6.

EXAMPLE 8

As an example, according to a method of manufacturing the organic light emitting diode, an anode was manufactured by cutting an ITO glass substrate having 15 Ω/cm² of sheet resistance into a size of 50 mm×50 mm×0.7 mm, and then cleaning the ITO glass substrate with an ultrasonic wave in acetone, isopropyl alcohol, and pure water respectively for 15 minutes, and with a UV ozone for 30 minutes.

This ITO transparent electrode was used as an anode, and a 1200 Å-thick hole injection layer was formed on the ITO substrate upper by vacuum-depositing the following HTM compound and the compound according to Example 1.

[HTM]

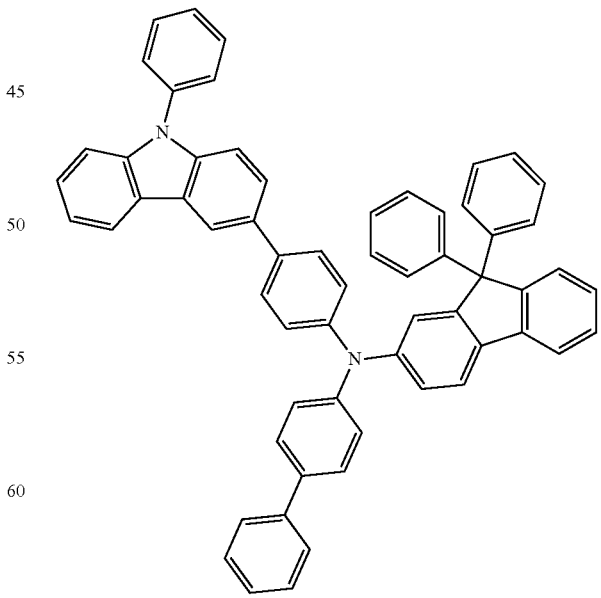

4,4-N,N-dicarbazolebiphenyl (CBP) as a host for an emission layer was doped with 7 wt % of the following PhGD compound as a phosphorescence green dopant and then vacuum-deposited to form a 300 Å-thick emission layer. An anode was 1000 Å-thick ITO, and a cathode was 1000 Å-thick aluminum (Al).

[PhGD]

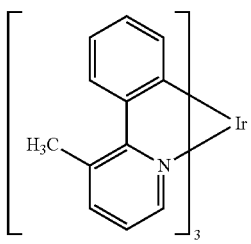

Subsequently, BAlq [bis(2-methyl-8-quinolinolato-N1, O8)-(1,1'-biphenyl-4-olato)aluminum] and Alq3 [tris(8-hydroxyquinolinato)aluminum] were sequentially deposited to be respectively 50 Å and 250 Å thick on the emission layer to form an electron transport layer. On the electron transport layer, LiF and Al were sequentially vacuum-deposited to be respectively 5 Å and 1000 Å thick to form a cathode, manufacturing an organic light emitting diode.

[BAlq]

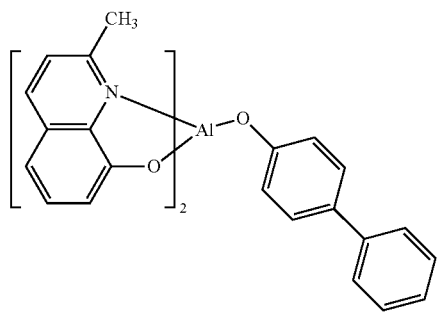

[Alq3]

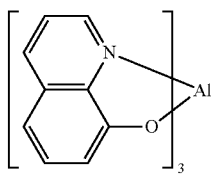

EXAMPLE 9

An organic light emitting diode was manufactured according to the same method as Example 8 except for using the compound according to Example 3 instead of the compound according to Example 1.

Comparative Example 1

An organic light emitting diode was manufactured according to the same method as Example 6 except for using 4,4-N,N-dicarbazolebiphenyl (CBP) as a host for an emission layer instead of the compound according to Example 1.

(Performance Measurement of Organic Light Emitting Diode)

Current density and luminance changes depending on voltage and luminous efficiency of each organic light emitting diode according to Examples 6 to 9 and Comparative Example 1 were measured. The measurements were specifically performed in the following method, and the results were provided in the following Tables 1 and 2.

(1) Measurement of Current density Change Depending on Voltage Change

The manufactured organic light emitting diodes were measured for current value flowing in the unit device, while increasing the voltage from 0 V to 10 V using a current-voltage meter (Keithley 2400), and the measured current value was divided by an area to provide the results.

(2) Measurement of Luminance Change Depending on Voltage Change

The organic light emitting diodes were measured for luminance, while increasing the voltage form 0 V to 10 V using a luminance meter (Minolta Cs-1000A).

(3) Measurement of Luminous Efficiency

Current efficiency (cd/A) and power efficiency (lm/W) at the same current density (10 mA/cm$^2$) were calculated by using the luminance, current density, and voltages from the items (1) and (2).

TABLE 1

|  | Driving voltage (Vd, V) | Current efficiency (cd/A) | Power efficiency (lm/W) | Luminance (cd/m$^2$) | Color coordinate (CIEx) | Color coordinate (CIEy) |
| --- | --- | --- | --- | --- | --- | --- |
| Comparative Example 1 | 4.90 | 44.8 | 28.7 | 3000 | 0.329 | 0.626 |
| Example 6 | 5.07 | 48.8 | 30.2 | 3000 | 0.325 | 0.629 |
| Example 7 | 5.14 | 49.0 | 30.0 | 3000 | 0.330 | 0.625 |

The organic light emitting diodes according to Examples 6 and 7 showed improved efficiency compared with the organic light emitting diodes manufactured by applying CBP as a host for an emission layer according to Comparative Example 1.

TABLE 2

|  | Driving voltage (Vd, V) | Current efficiency (cd/A) | Power efficiency (lm/W) | Luminance (cd/m$^2$) | Color coordinate (CIEx) | Color coordinate (CIEy) |
| --- | --- | --- | --- | --- | --- | --- |
| Comparative Example 1 | 4.90 | 44.8 | 28.7 | 3000 | 0.329 | 0.626 |
| Example 8 | 4.75 | 62.4 | 41.2 | 3000 | 0.295 | 0.674 |
| Example 9 | 5.10 | 68.4 | 42.1 | 3000 | 0.322 | 0.654 |

The organic light emitting diodes including an intermediate layer according to Examples 8 and 9 showed improved efficiency compared with the organic light emitting diode using CBP as a single host for an emission layer according to Comparative Example 1.

By way of summation and review, improved luminous efficiency and life-span may enable a larger display. Luminous efficiency benefits from smooth combination between holes and electrons in an emission layer. If an organic material in general has slower electron mobility than hole mobility, it may provide relatively inefficient combination between holes and electrons. Accordingly, increasing electron injection and mobility from a cathode, and simultaneously preventing movement of holes is desired.

Preventing a material crystallization caused by Joule heats generated during device operating may improve life-span. An organic compound having excellent electron injection and mobility, and high electrochemical stability is desirable.

As described above, embodiments relate to a compound for an organic optoelectronic device, which may provide an organic optoelectronic device having excellent life-span, efficiency, electrochemical stability, and thermal stability. Embodiments also relate to an organic light emitting diode including the compound, and a display device including the organic light emitting diode.

Embodiments may provide a compound for an organic optoelectronic device that may act as a hole injection and transport material or an electron injection and transport material, and also act as a light emitting host along with an appropriate dopant.

Embodiments may provide an organic light emitting diode having excellent life-span, efficiency, driving voltage, electrochemical stability, and thermal stability, and a display device including the same.

Embodiments may provide a compound having high hole or electron transport properties, film stability, thermal stability, and high triplet exciton energy. Such a compound may be used as a hole injection/transport material, host material, or electron injection/transport material of an emission layer.

An organic optoelectronic device using the same may use the compounds singularly or in a mixture thereof, and may have high luminous efficiency at a low driving voltage along with excellent electrochemical and thermal stability.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims.

What is claimed is:

1. A compound for an organic optoelectronic device represented by the following Chemical Formula 1:

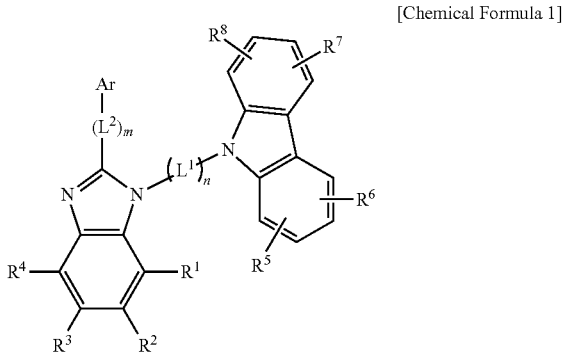

[Chemical Formula 1]

wherein, in the above Chemical Formula 1, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^8$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and at least one of $R^5$ to $R^8$ is a substituted or unsubstituted C3 to C30 heteroaryl group having hole characteristics, a substituted or unsubstituted C6 to C30 aryl group having hole transporting characteristics, a substituted or unsubstituted arylamine group having hole characteristics, or a combination thereof.

2. The compound for an organic optoelectronic device as claimed in claim 1, wherein at least one of the $R^5$ to $R^8$ is the substituted or unsubstituted C6 to C30 aryl group having hole transporting characteristics, the substituted or unsubstituted C6 to C30 aryl group having hole characteristics being a substituted or unsubstituted triphenylenyl group.

3. The compound for an organic optoelectronic device as claimed in claim 1, wherein the compound for an organic optoelectronic device is represented by the following Chemical Formula 2:

[Chemical Formula 2]

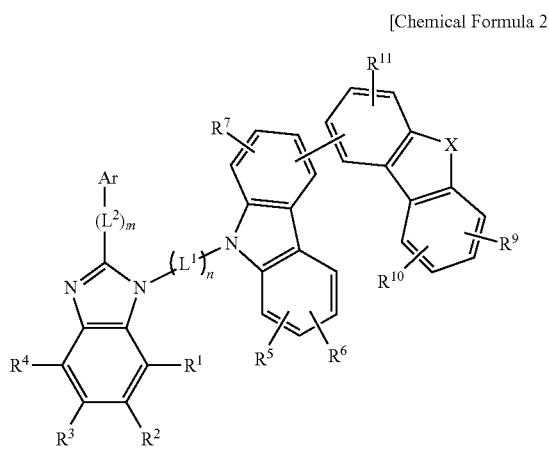

wherein, in the above Chemical Formula 2, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^7$ and $R^9$ to $R^{11}$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X is NR', O, or S, wherein the R' is hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

4. The compound for an organic optoelectronic device as claimed in claim 1, wherein the compound for an organic optoelectronic device is represented by the following Chemical Formula 3:

[Chemical Formula 3]

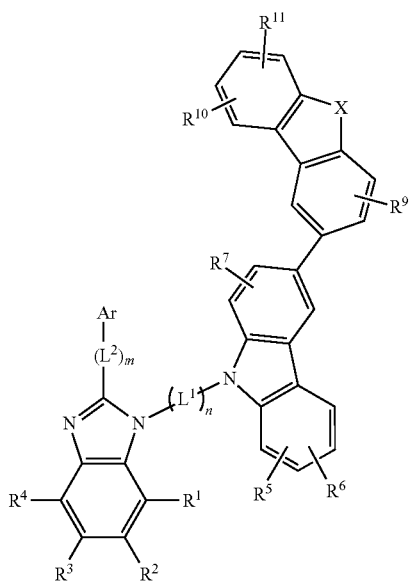

wherein, in the above Chemical Formula 3, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^7$ and $R^9$ to $R^{11}$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X is NR', O, or S, wherein the R' is hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

5. The compound for an organic optoelectronic device as claimed in claim 1, wherein the compound for an organic optoelectronic device is represented by the following Chemical Formula 4:

[Chemical Formula 4]

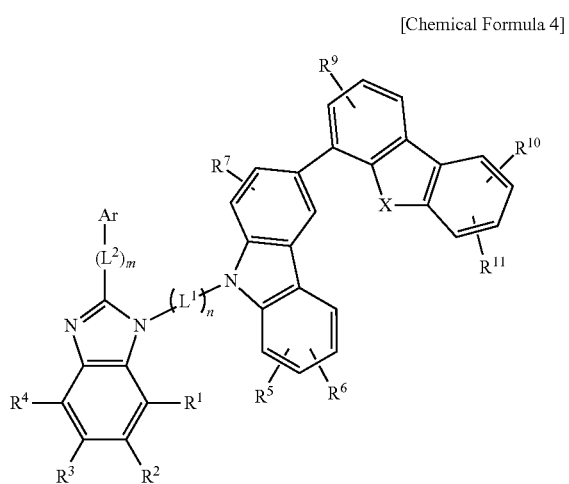

wherein, in the above Chemical Formula 4, $L^1$ and $L^2$ are each independently a single bond, a substituted or unsubstituted C2 to C6 alkenylene group, a substituted or unsubstituted C2 to C6 alkynylene group, a substituted or unsubstituted C6 to C30 arylene group, a substituted or unsubstituted C3 to C30 heteroarylene group, or a combination thereof, n and m are each independently integers ranging from 0 to 3, Ar is a substituted or unsubstituted C6 to C30 aryl group, a substituted or unsubstituted C3 to C30 heteroaryl group, or a combination thereof, $R^1$ to $R^7$ and $R^9$ to $R^{11}$ are each independently hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof, and X is NR', O, or S, wherein the R' is hydrogen, deuterium, a substituted or unsubstituted C1 to C20 alkyl group, a substituted or unsubstituted C6 to C30 aryl group, a substituted or unsubstituted C3 to C30 heteroaryl group, or a combination thereof.

6. The compound for an organic optoelectronic device as claimed in claim 1, wherein the Ar is a substituted or unsubstituted biphenyl group, a substituted or unsubstituted pyridinyl group, a substituted or unsubstituted pyrimidinyl group, a substituted or unsubstituted triazinyl group, or a combination thereof.

7. The compound for an organic optoelectronic device as claimed in claim 1, wherein the $L^1$ is a substituted or unsubstituted phenylene group.

8. The compound for an organic optoelectronic device as claimed in claim 1, wherein the n is 1, and the m is 0 or 1.

9. The compound for an organic optoelectronic device as claimed in claim 1, wherein the substituted or unsubstituted C3 to C30 heteroaryl group having hole transporting characteristics is a substituted or unsubstituted carbazolyl-based derivative, a substituted or unsubstituted dibenzofuranyl-based derivative, a substituted or unsubstituted dibenzothiophenyl-based derivative, or a combination thereof.

10. The compound for an organic optoelectronic device as claimed in claim 1, wherein the substituted or unsubstituted C6 to C30 aryl group having hole characteristics is a substituted or unsubstituted fluorenyl group, a substituted or unsubstituted Spiro-fluorenyl group, or a combination thereof.

11. The compound for an organic optoelectronic device as claimed in claim 1, wherein the substituted or unsubstituted arylamine group having hole transporting characteristics includes a single aryl group or a plurality of aryl groups, and the single aryl group or a plurality of aryl groups is independently a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, or a combination thereof.

12. A compound for an organic optoelectronic device represented by one of the following Chemical Formulae A1 to A21:

[Chemical Formula A1]

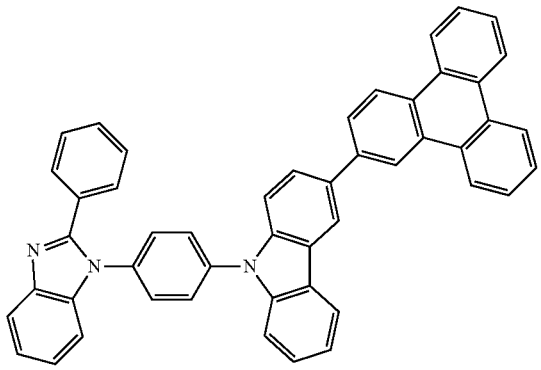

[Chemical Formula A2]

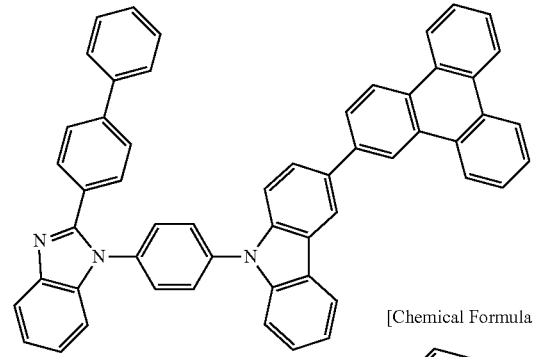

[Chemical Formula A3]

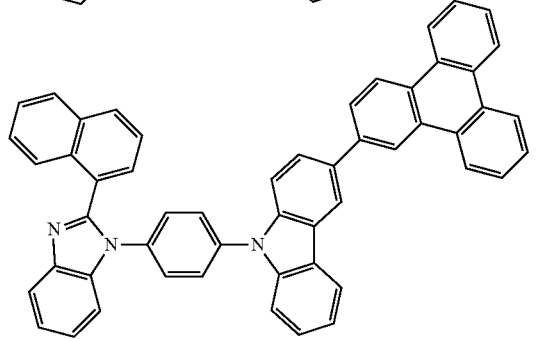

-continued
[Chemical Formula A4]
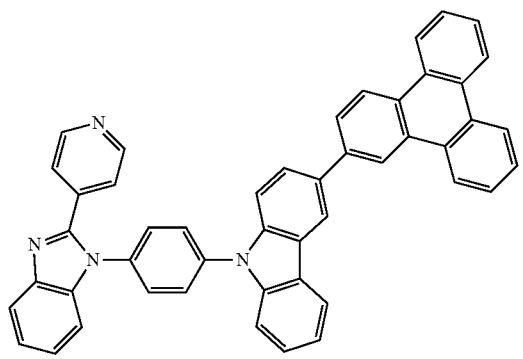
[Chemical Formula A5]
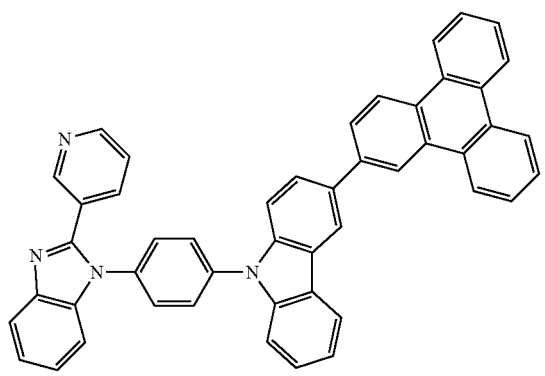
[Chemical Formula A6]
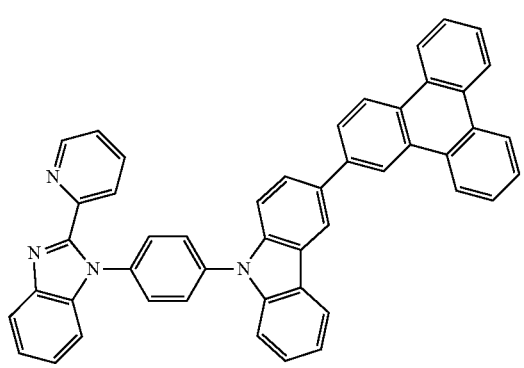
[Chemical Formula A7]
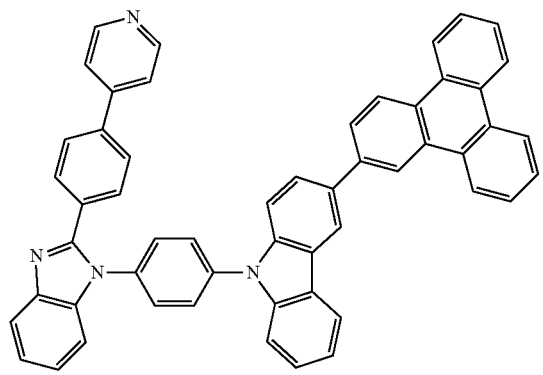
-continued
[Chemical Formula A8]
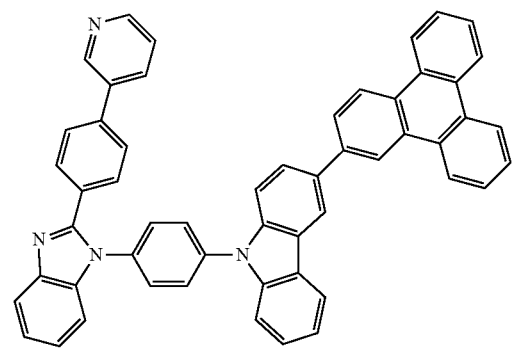
[Chemical Formula A9]
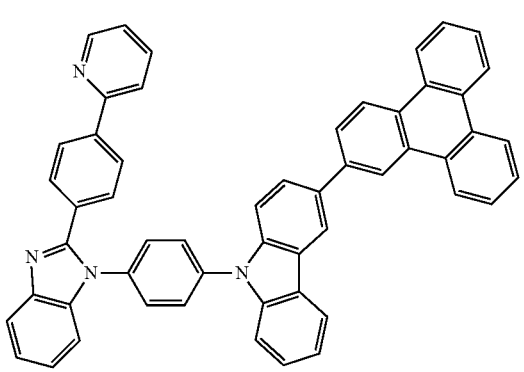
[Chemical Formula A10]
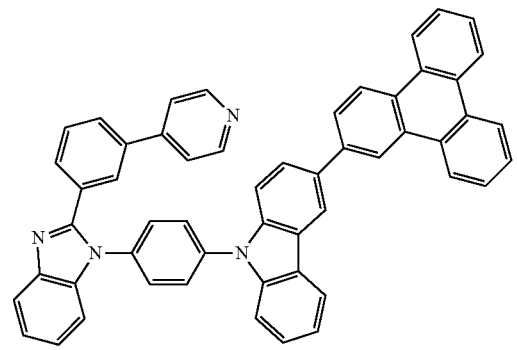
[Chemical Formula A11]
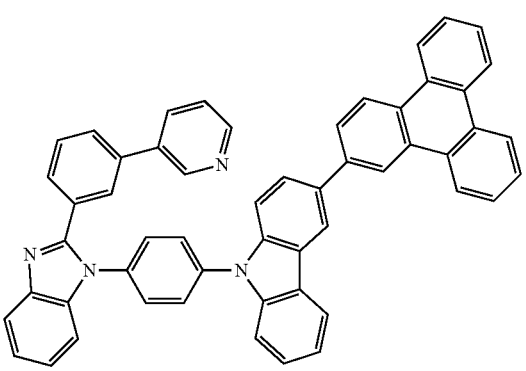

[Chemical Formula A12]
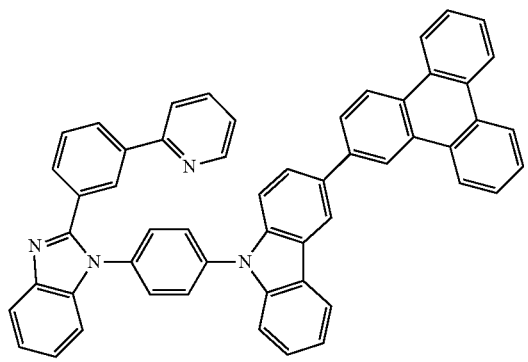
[Chemical Formula A13]
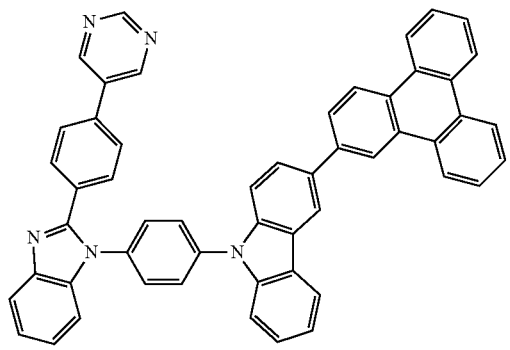
[Chemical Formula A14]
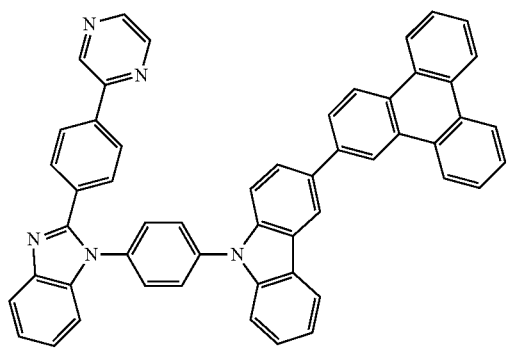
[Chemical Formula A15]
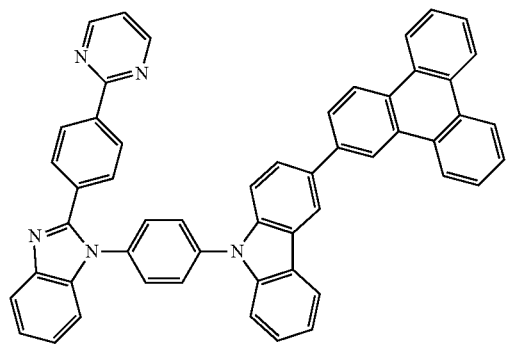
[Chemical Formula A16]
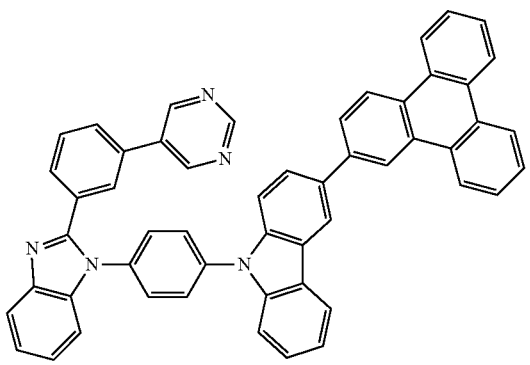
[Chemical Formula A17]
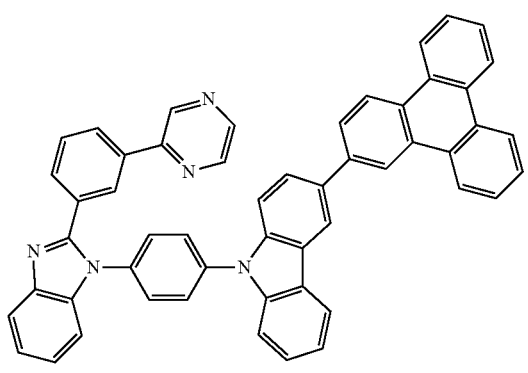
[Chemical Formula A18]
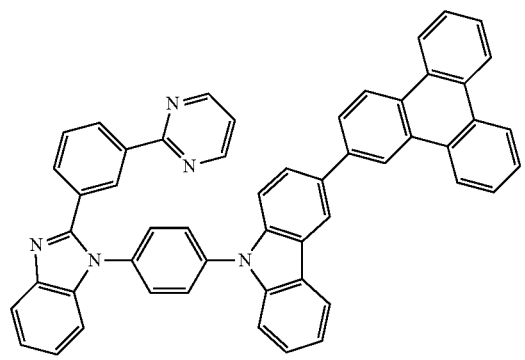
[Chemical Formula A19]
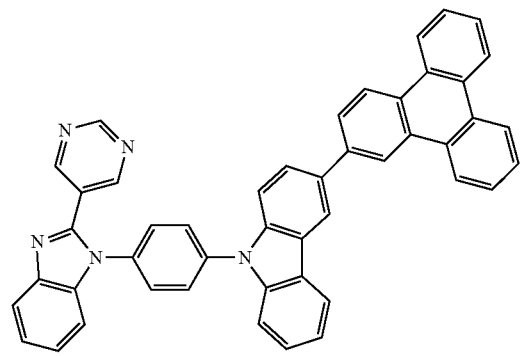

[Chemical Formula A20]
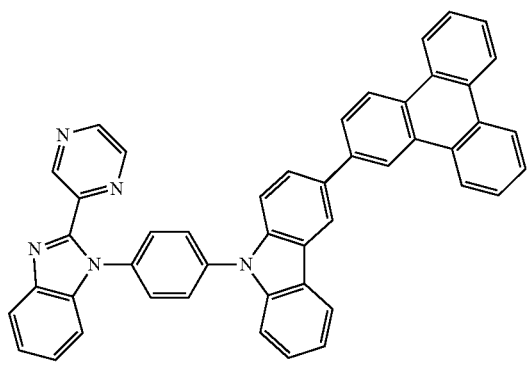
[Chemical Formula A21]
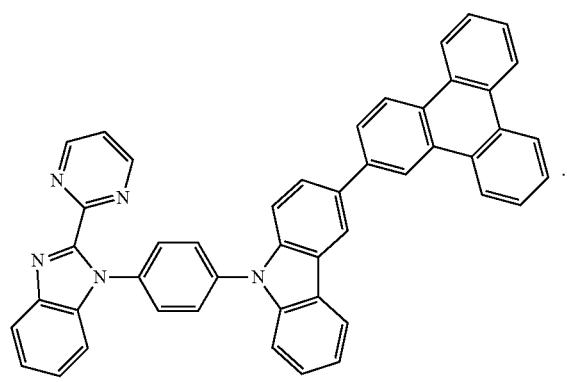
13. A compound for an organic optoelectronic device represented by one of the following Chemical Formulae B1 to B42:
[Chemical Formula B1]
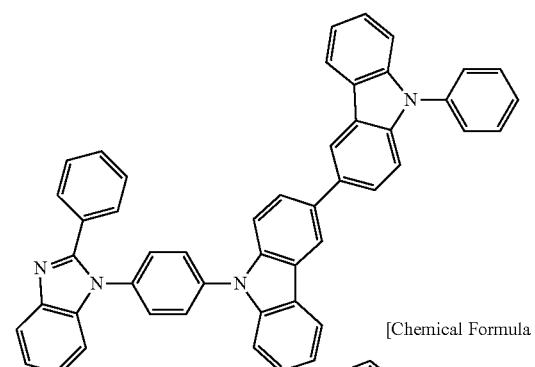
[Chemical Formula B2]
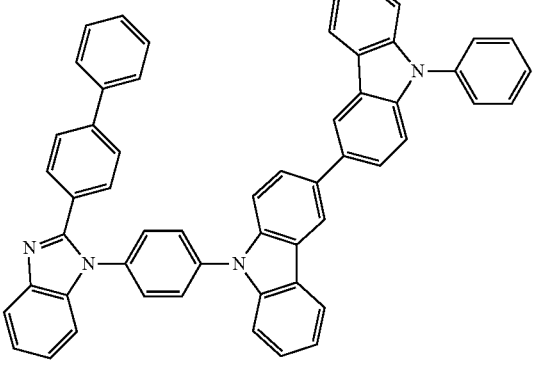
[Chemical Formula B3]
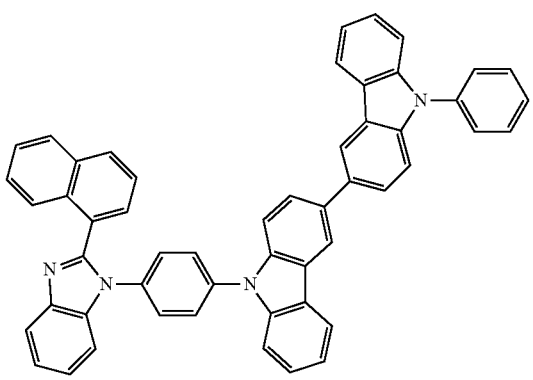
[Chemical Formul B4]
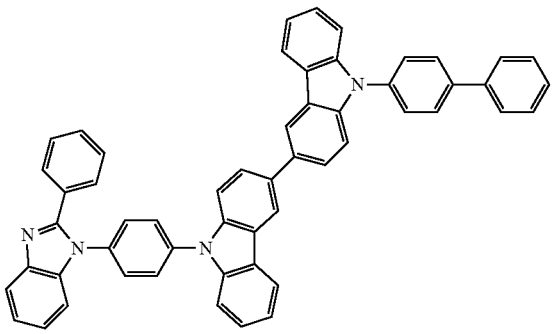
[Chemical Formula B5]
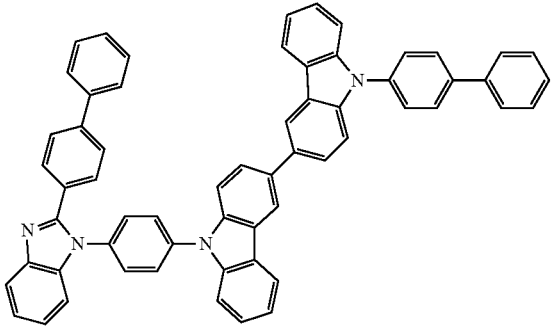
[Chemical Formula B6]
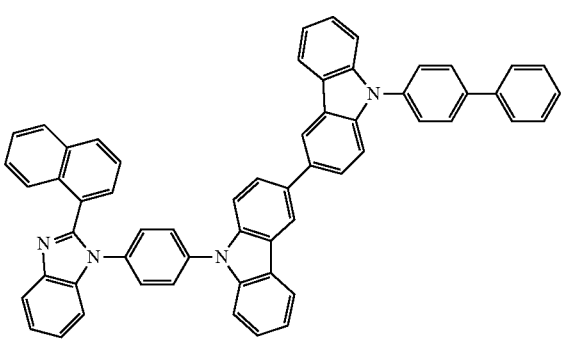

[Chemical Formula B7]
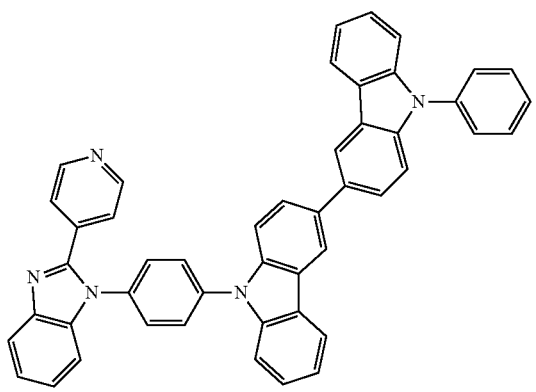
[Chemical Formula B8]
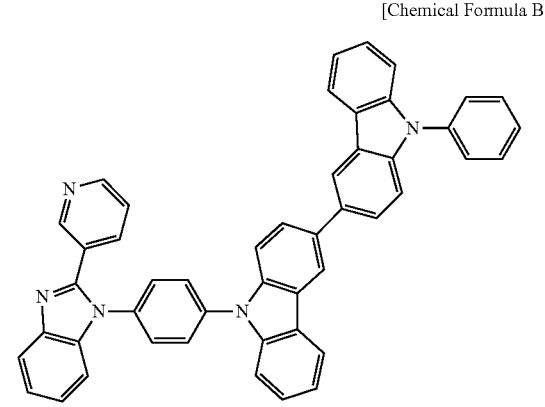
[Chemical Formula B9]
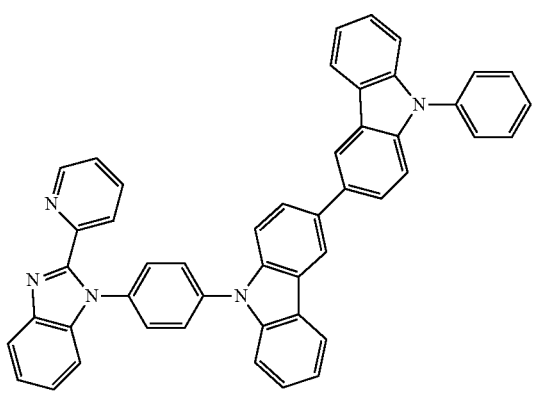
[Chemical Formula B10]
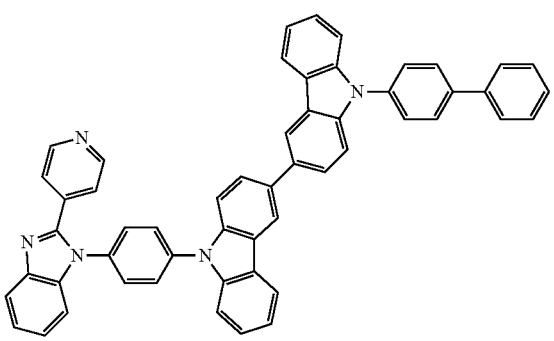
[Chemical Formula B11]
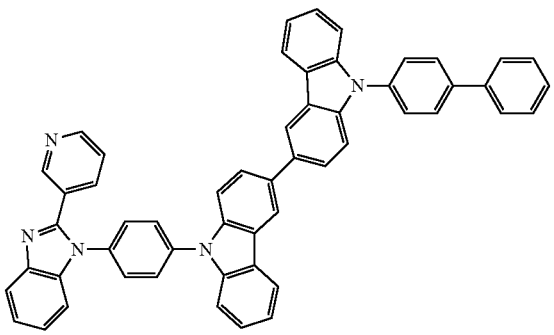
[Chemical Formula B12]
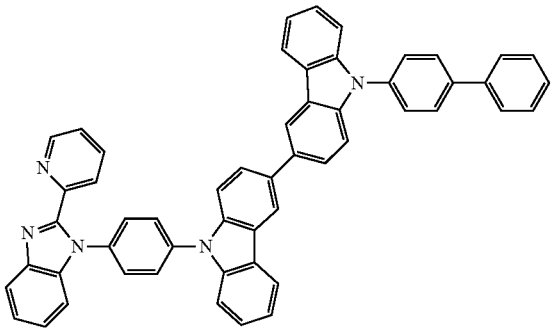
[Chemical Formula B13]
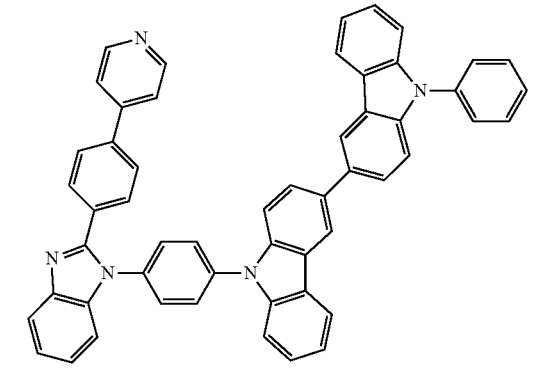
[Chemical Formula B14]
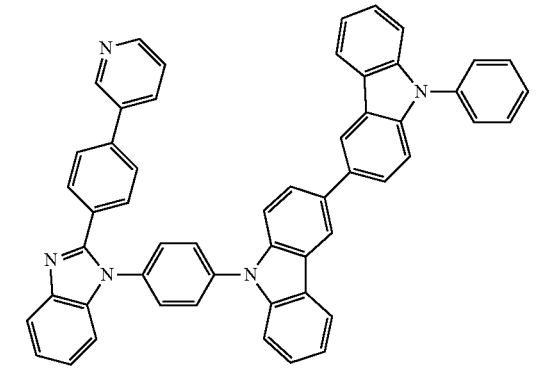

[Chemial Formula B15]
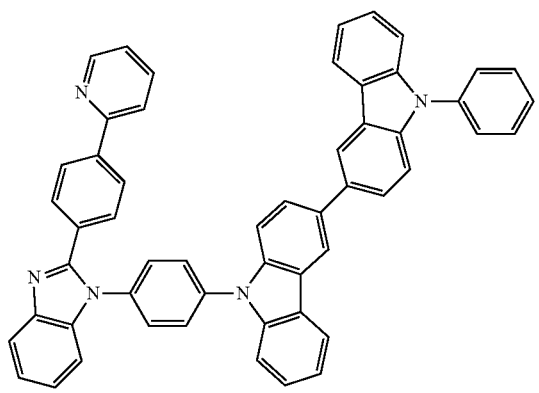
[Chemical Formula B16]
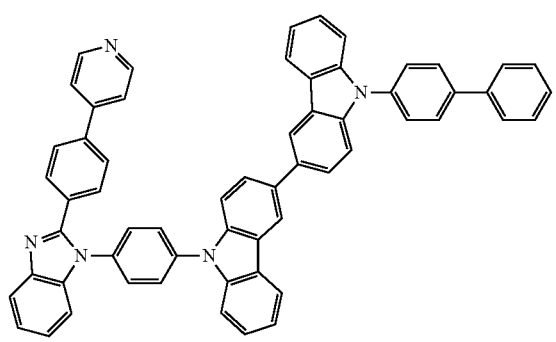
[Chemical Formula B17]
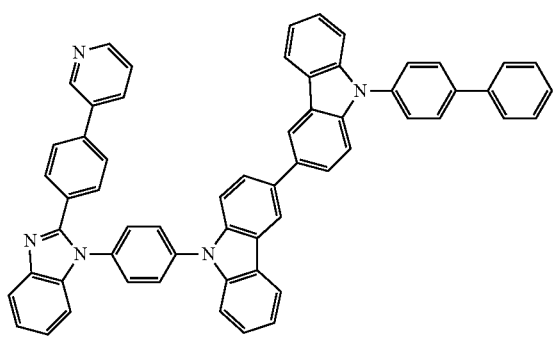
[Chemical Formula B18]
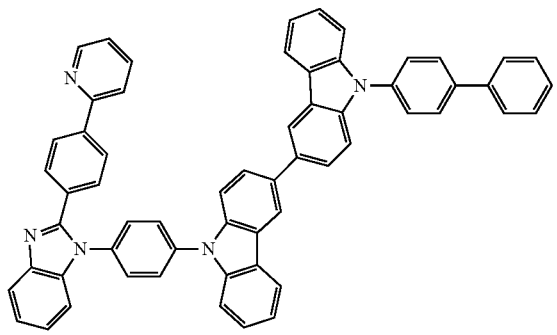
[Chemical Formula B19]
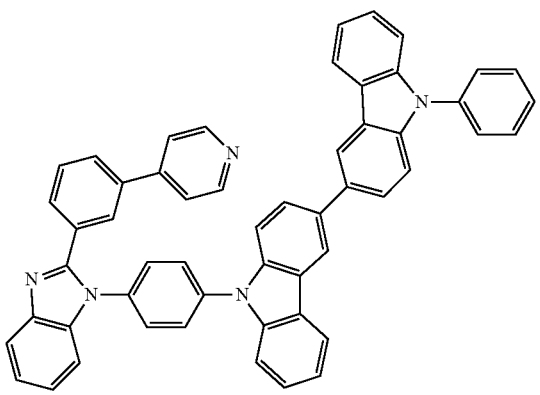
[Chemical Formula B20]
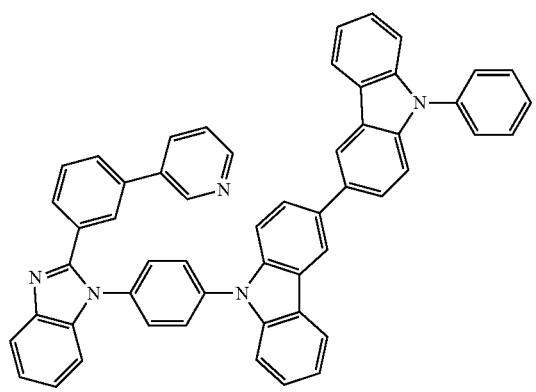
[Chemical Formula B21]
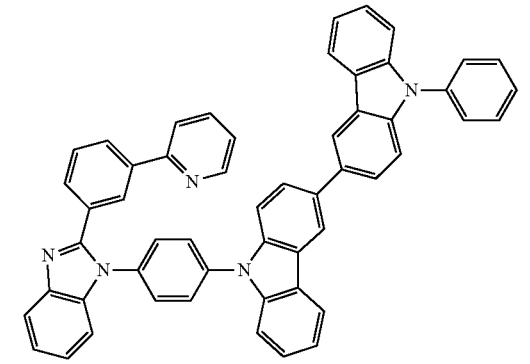
[Chemical Formula B22]
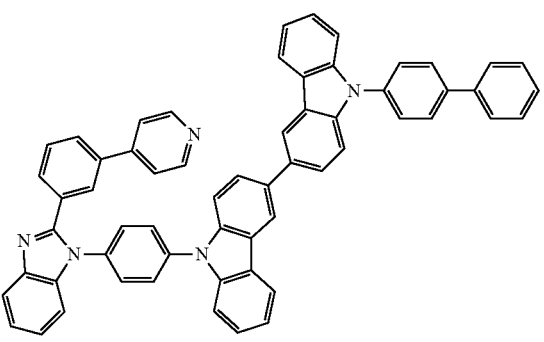

[Chemical Formula B23]
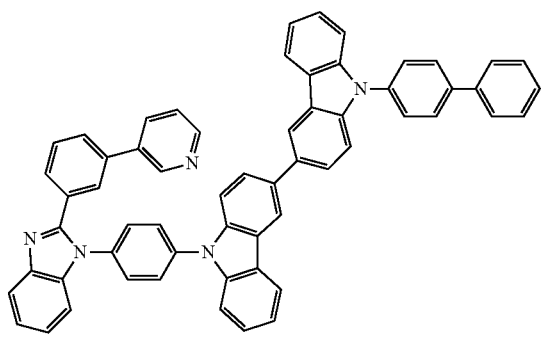
[Chemical Formula B24]
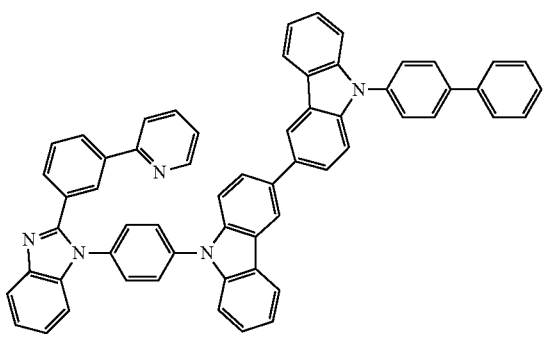
[Chemical Formula B25]
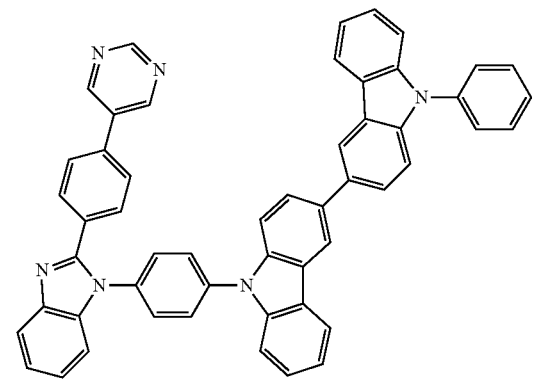
[Chemical Formula B26]
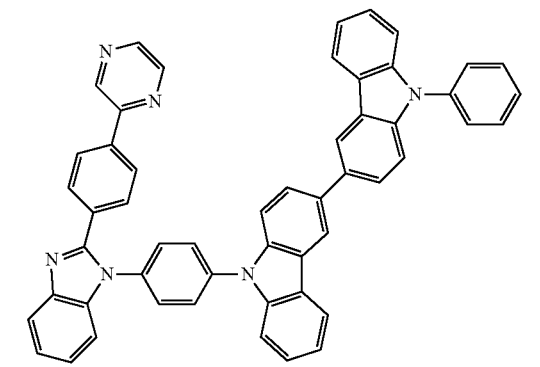
[Chemical Formula B27]
[Chemical Formula B28]
[Chemical Formula B29]
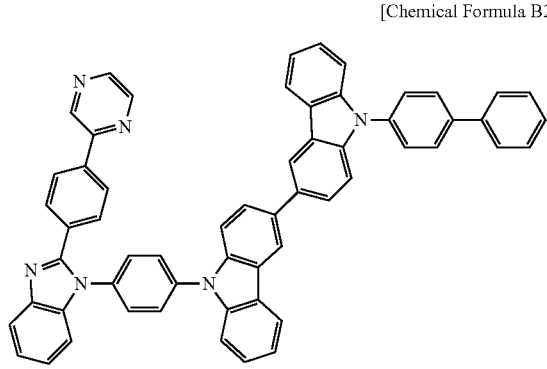
[Chemical Formula B30]
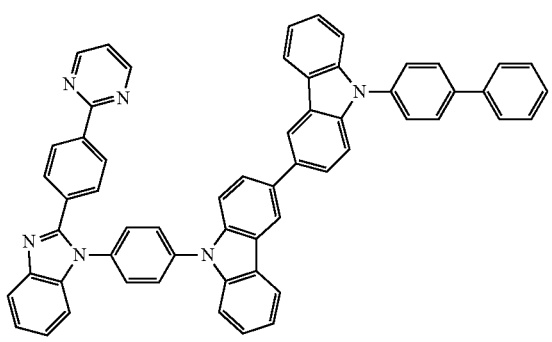

[Chemical Formula B31]
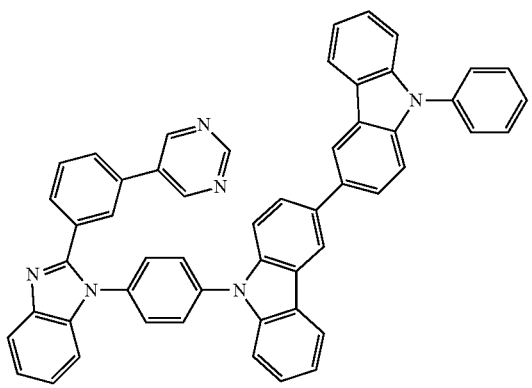
[Chemical Formula B32]
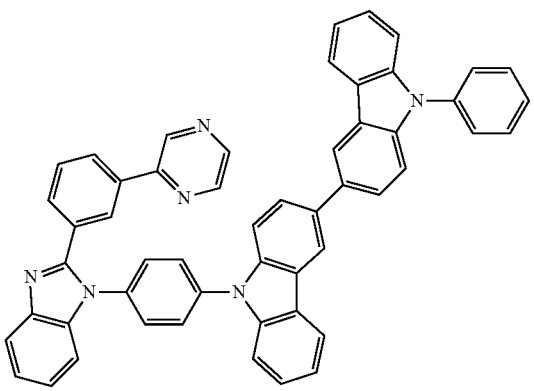
[Chemical Formula B33]
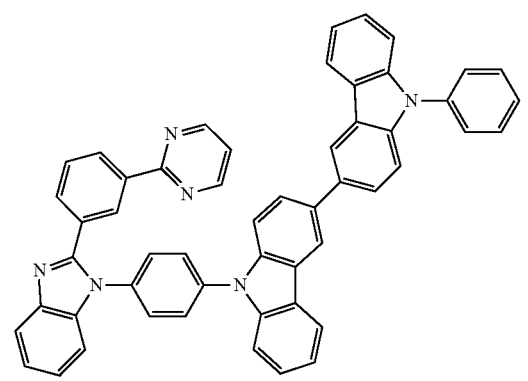
[Chemical Formula B34]
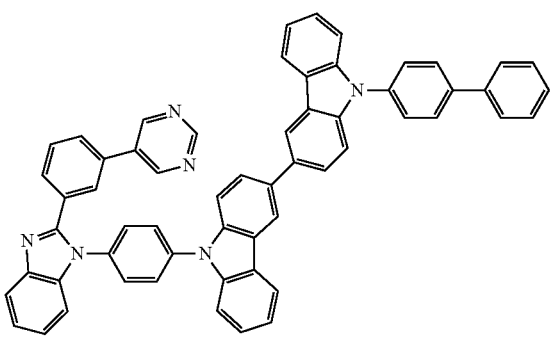
[Chemical Formula B35]
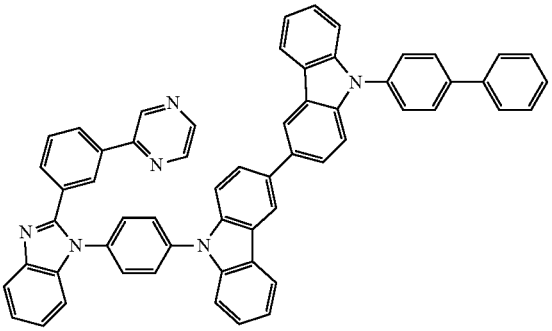
[Chemical Formula B36]
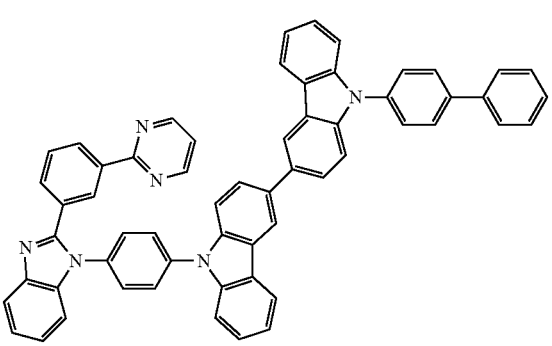
[Chemial Formula B37]
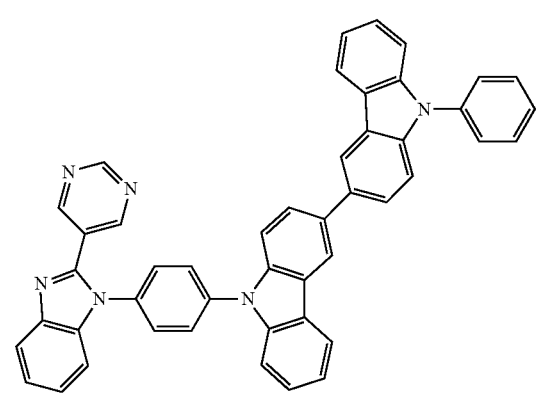
[Chemical Formula B38]
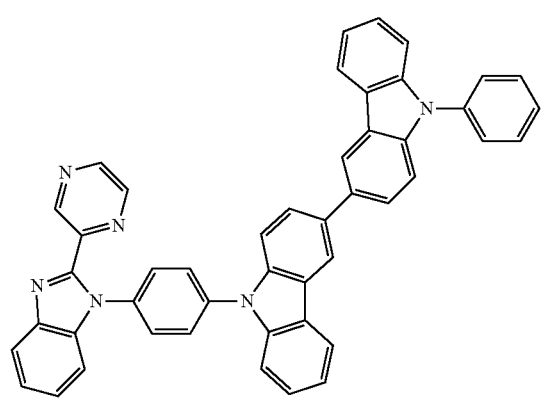

-continued
[Chemical Formula B39]
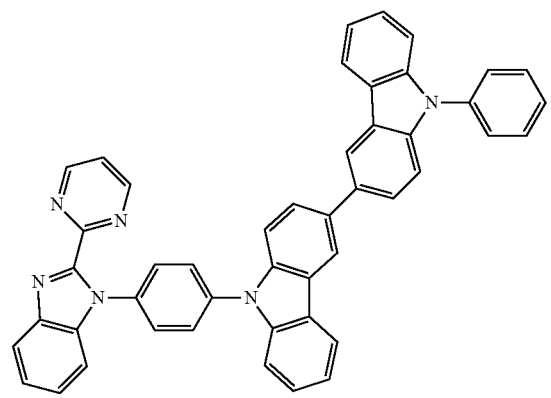
[Chemical Formula B40]
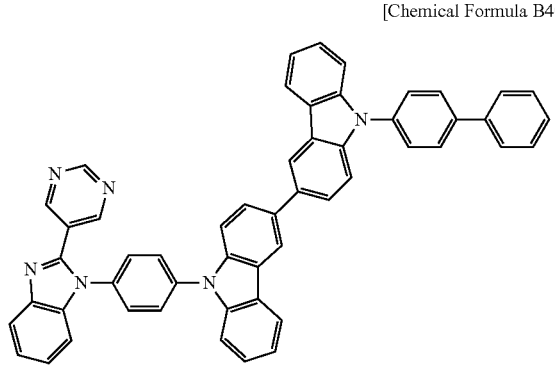
[Chemical Formula B41]
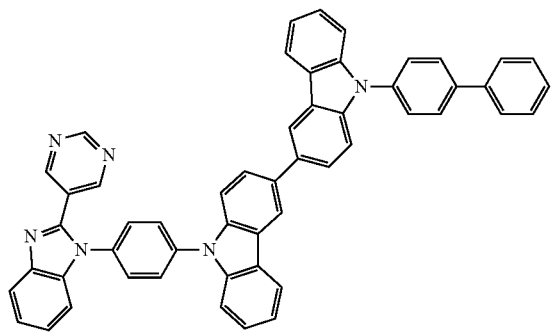
[Chemical Formula B42]
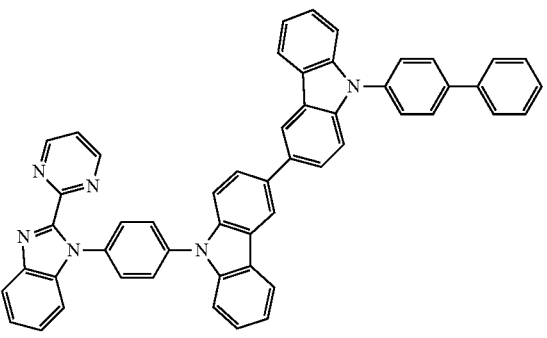
14. A compound for an organic optoelectronic device represented by one of the following Chemical Formulae C1 to C42:
[Chemical Formula C1]
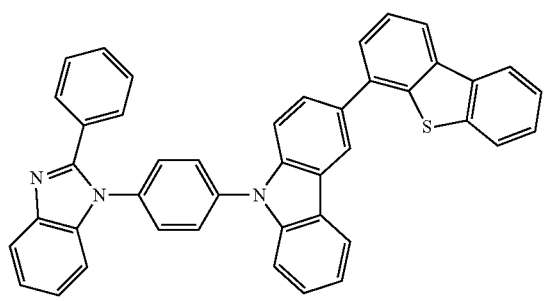
[Chemical Formula C2]
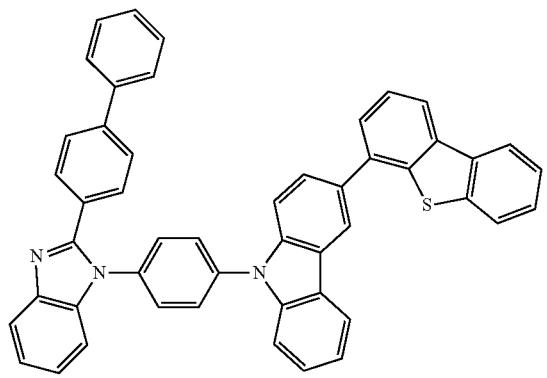
[Chemical Formula C3]
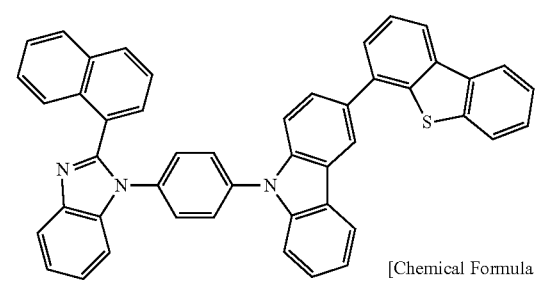
[Chemical Formula C4]
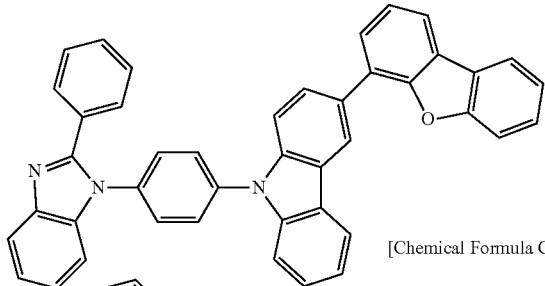
[Chemical Formula C5]
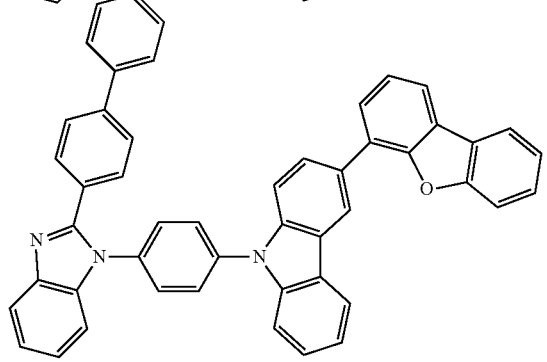

-continued
[Chemical Formula C6]
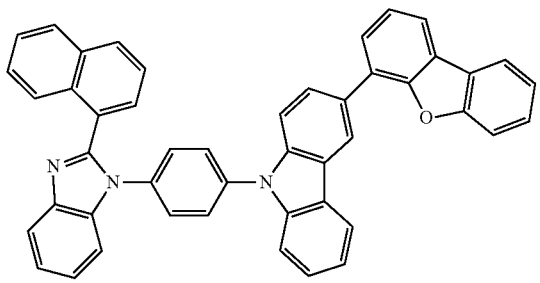
[Chemical Formula C7]
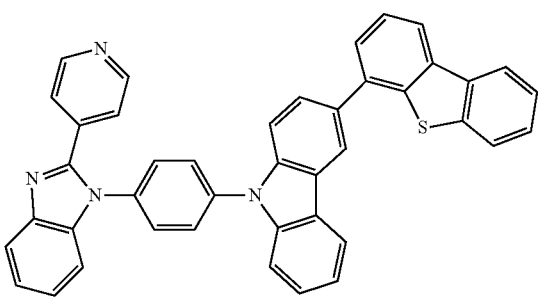
[Chemical Formula C8]
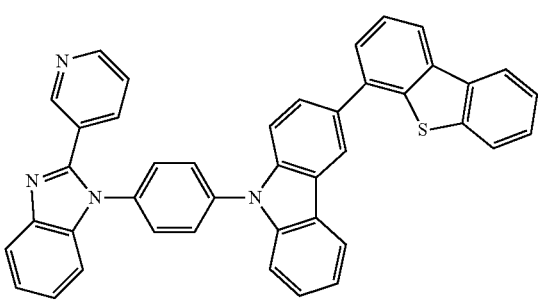
[Chemical Formula C9]
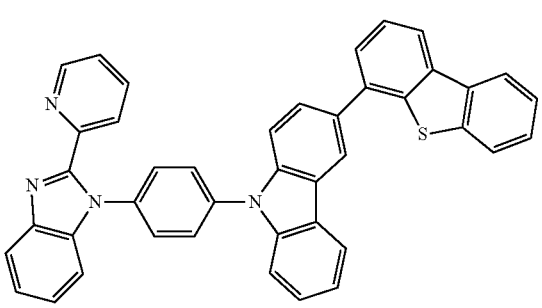
[Chemical Formula C10]
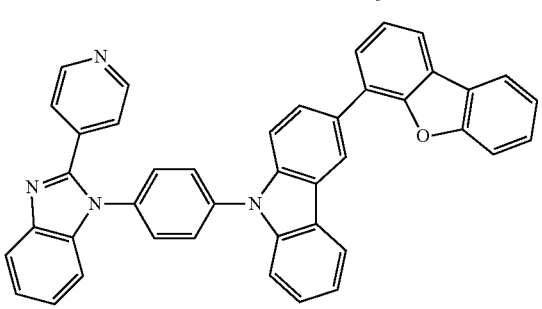
-continued
[Chemical Formula C11]
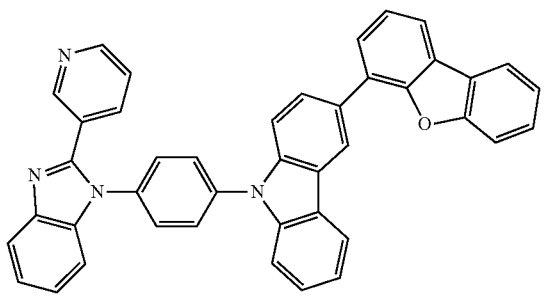
[Chemical Formula C12]
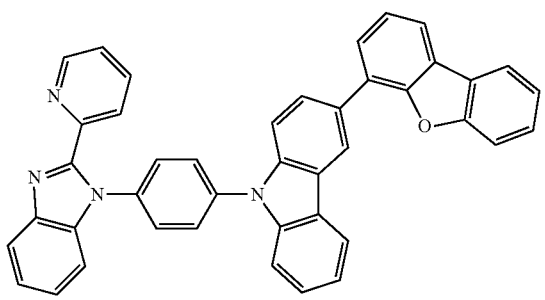
[Chemical Formula C13]
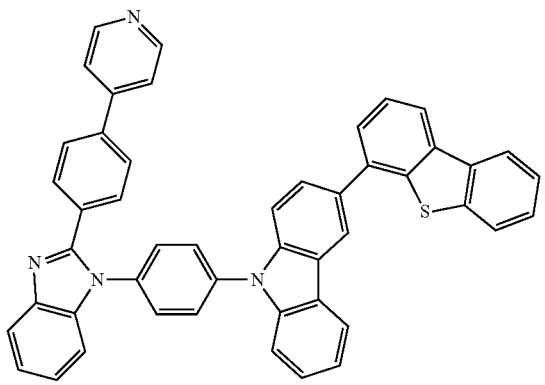
[Chemical Formula C14]
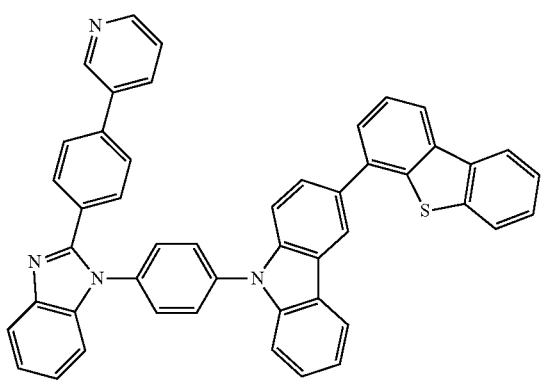

[Chemical Formula C15]
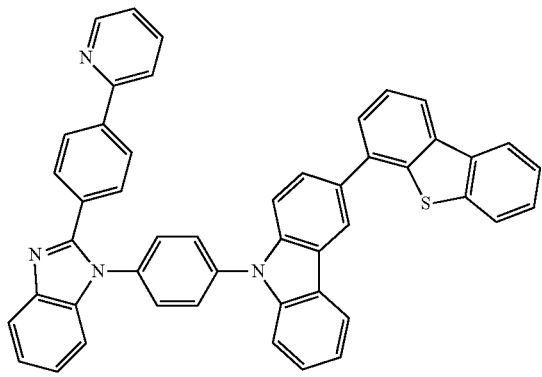
[Chemical Formula C16]
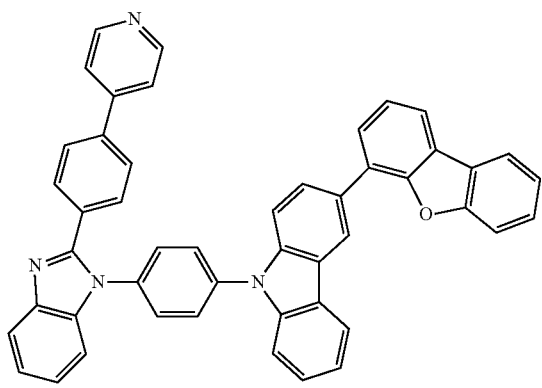
[Chemical Formula C17]
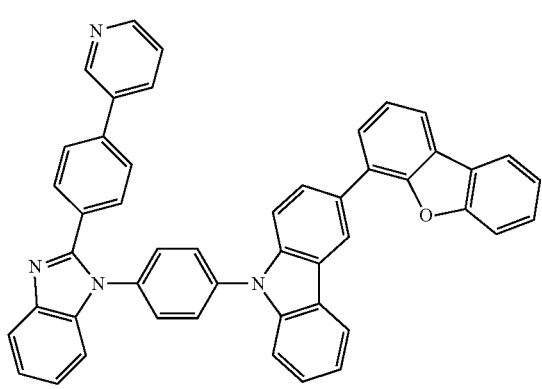
[Chemical Formula C18]
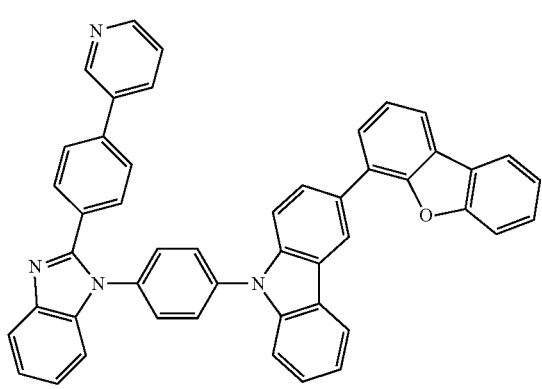
[Chemical Formula C19]
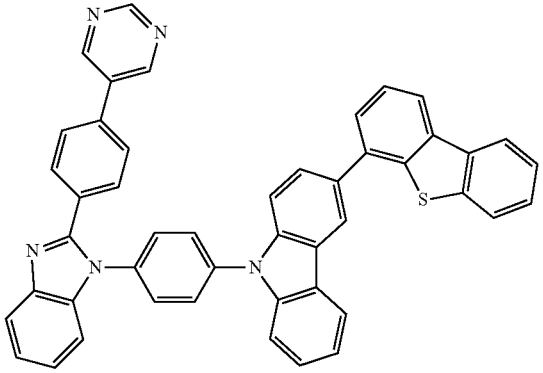
[Chemical Formula C20]
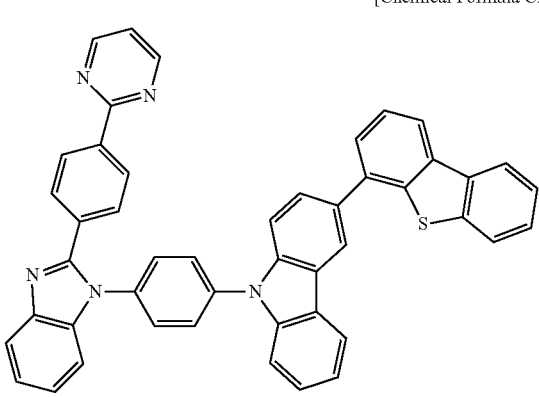
[Chemical Formula C21]
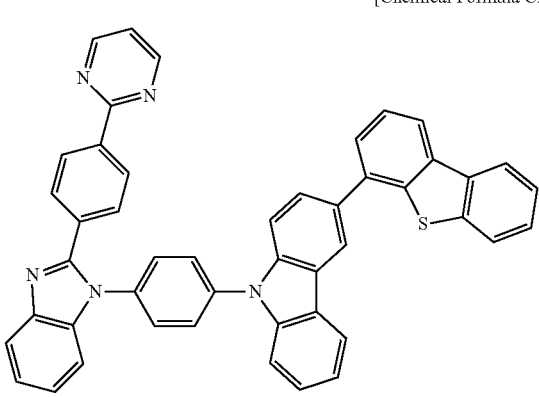
[Chemical Formula C22]
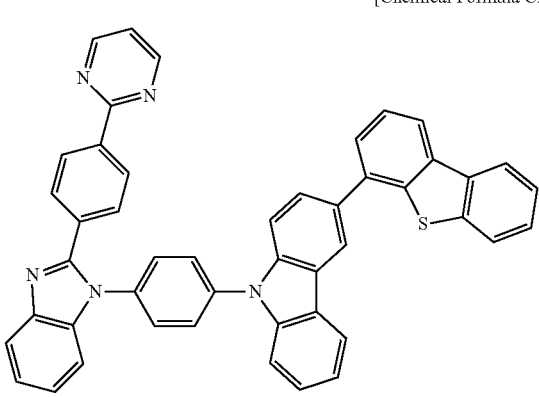

[Chemical Formula C23]
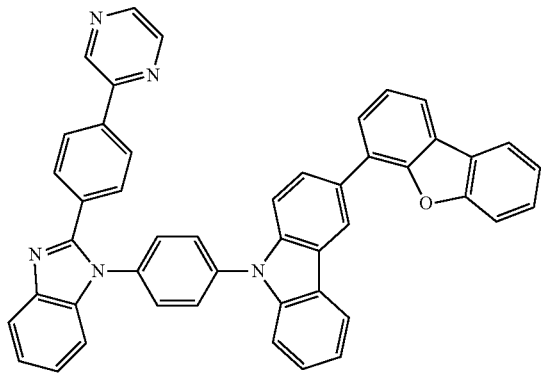
[Chemical Formula C24]
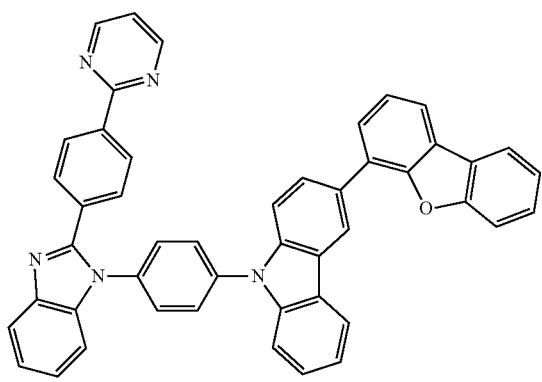
[Chemical Formula C25]
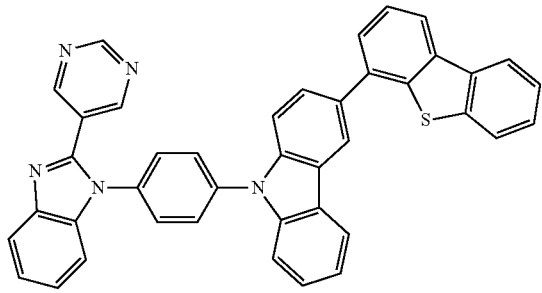
[Chemical Formula C26]
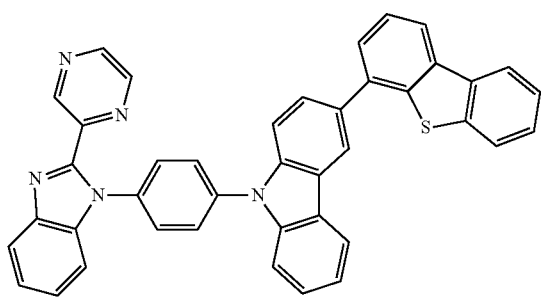
[Chemical Formula C27]
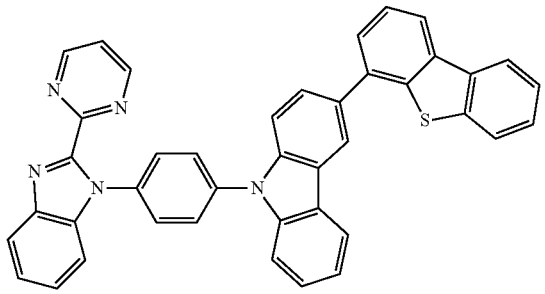
[Chemical Formula C28]
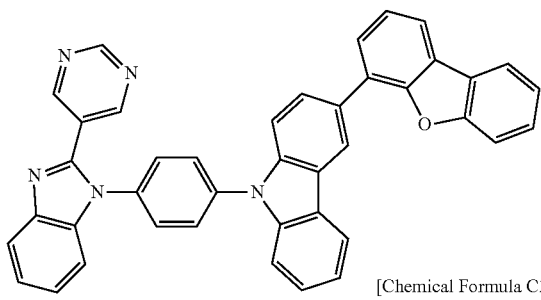
[Chemical Formula C29]
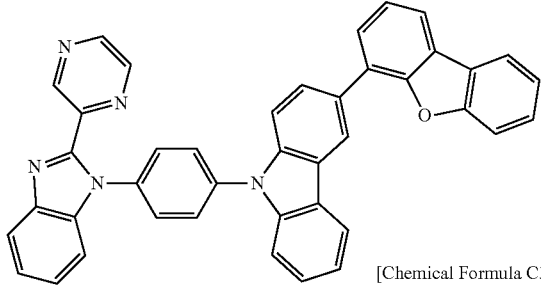
[Chemical Formula C30]
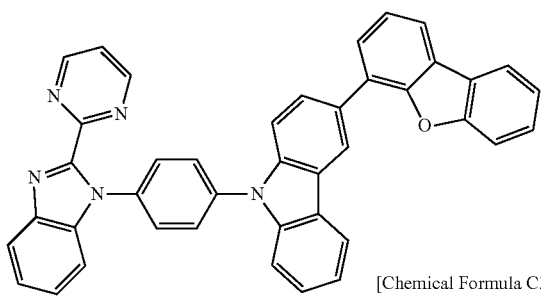
[Chemical Formula C31]
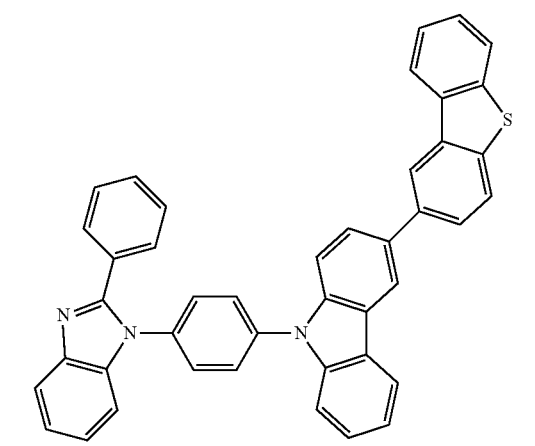

[Chemical Formula C32]
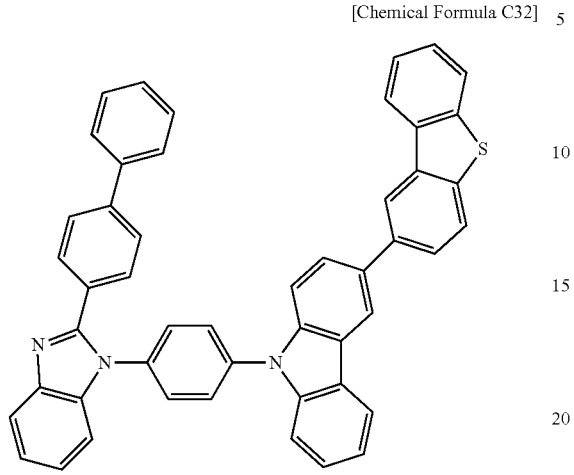
[Chemical Formula C33]
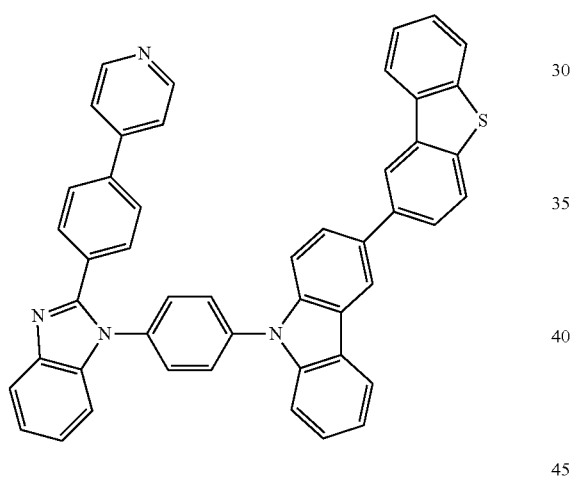
[Chemical Formula C34]
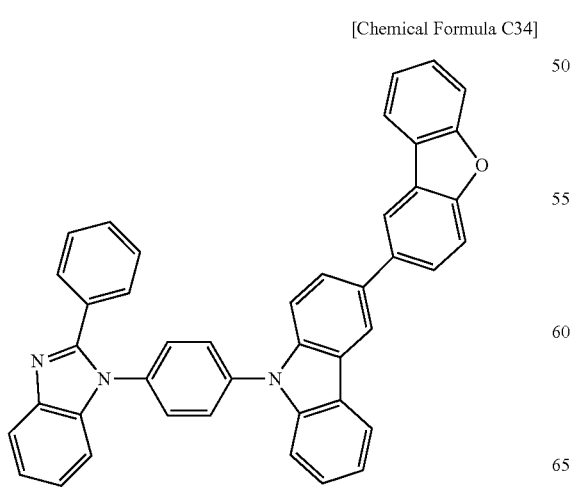
[Chemical Formula C35]
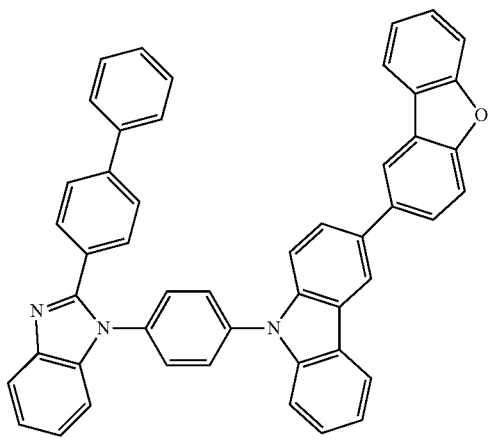
[Chemical Formula C36]
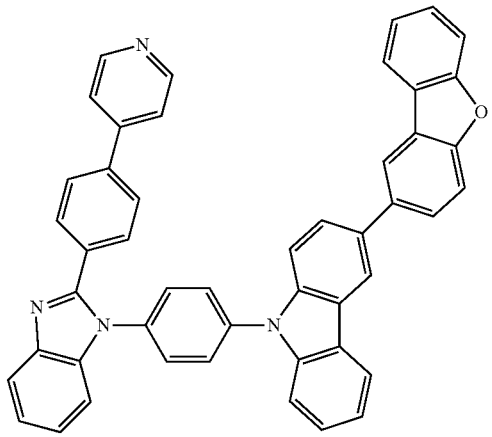
[Chemical Formula C37]
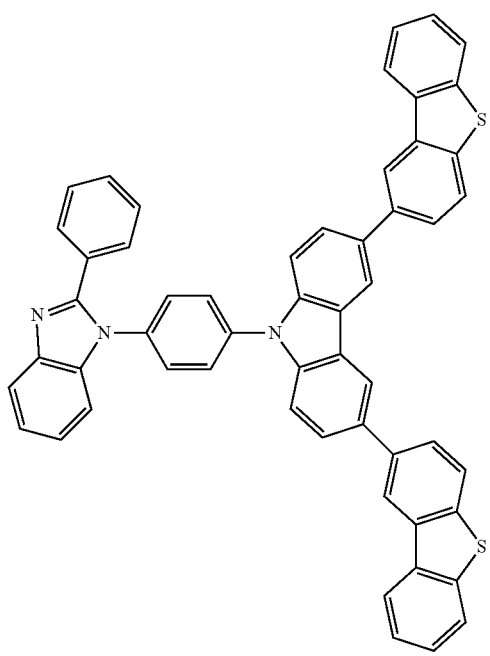

[Chemical Formula C38]
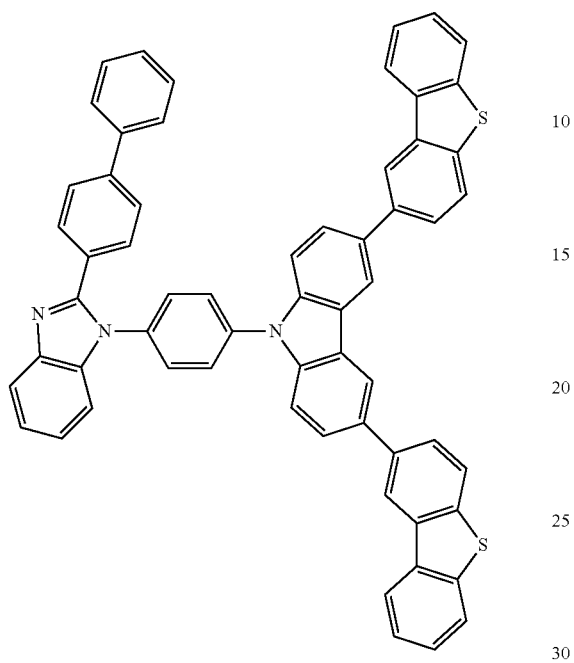
[Chemical Formula C40]
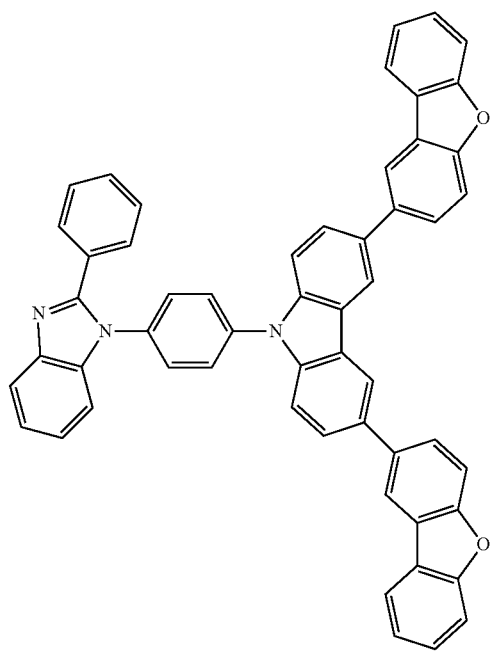
[Chemical Formula C39]
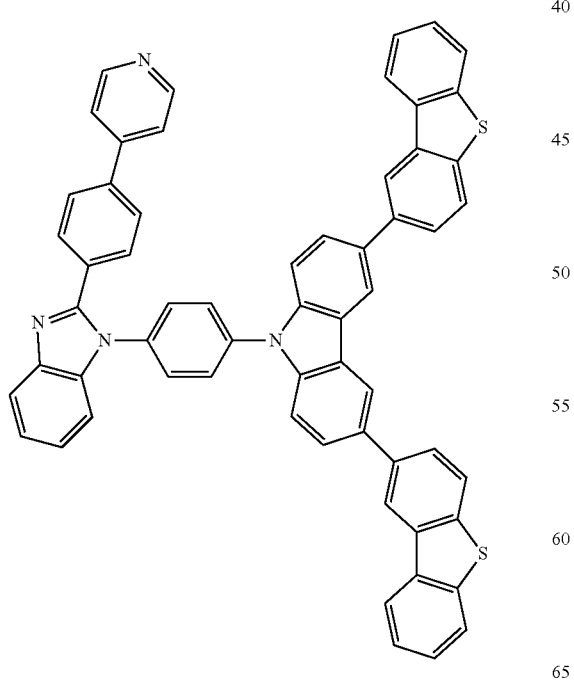
[Chemical Formula C41]
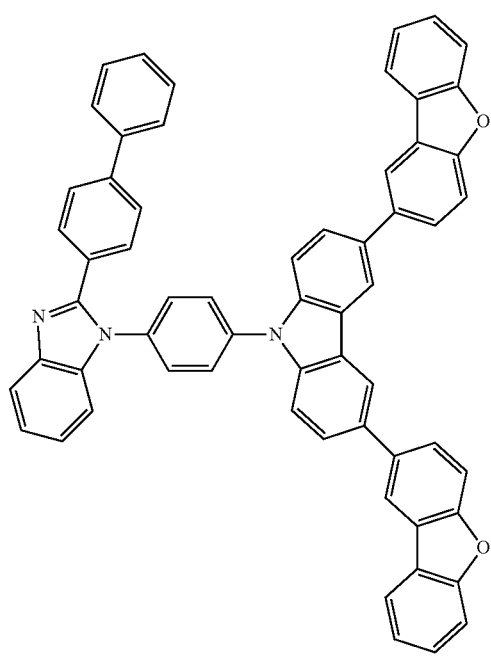

[Chemical Formula C42]

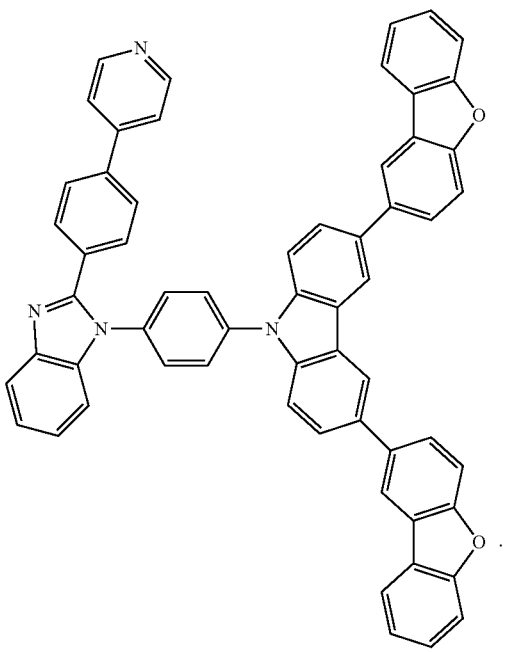

15. The compound for an organic optoelectronic device as claimed in claim 1, wherein the organic optoelectronic device is selected from an organic photoelectric device, an organic light emitting diode, organic solar cell, an organic transistor, an organic photo conductor drum, and an organic memory device.

16. An organic light emitting diode, comprising:
an anode, a cathode, and one or more organic thin layers between the anode and the cathode,
wherein at least one of the organic thin layers includes the compound for an organic optoelectronic device as claimed in claim 1.

17. The organic light emitting diode as claimed in claim 16, wherein the organic thin layer is an emission layer, a hole transport layer, a hole injection layer, an electron transport layer, an electron injection layer, a hole blocking layer, or a combination thereof.

18. The organic light emitting diode as claimed in claim 17, wherein the compound for an organic optoelectronic device is included in an emission layer.

19. The organic light emitting diode as claimed in claim 17, wherein the compound for an organic optoelectronic device is a phosphorescent or fluorescent host material in an emission layer.

20. The organic light emitting diode as claimed in claim 17, wherein the compound for an organic optoelectronic device is a material of a hole transport layer, a hole injection layer, an electron transport layer, an electron injection layer, or a hole blocking layer.

* * * * *